United States Patent
Gurovich et al.

(10) Patent No.: US 12,226,312 B2
(45) Date of Patent: *Feb. 18, 2025

(54) PROSTHETIC HEART VALVE

(71) Applicant: EDWARDS LIFESCIENCES CORPORATION, Irvine, CA (US)

(72) Inventors: Nikolai Gurovich, Hadera (IL); Michael Bukin, Pardes Hanna (IL); Elena Sherman, Pardes Hana (IL); Tamir S. Levi, Zikhron Yaakov (IL); Ziv Yohanan, Kfar Hahoresh (IL); Gil Senesh, Laguna Beach, CA (US); Dikla Kersh, Karkur (IL); Alexey Tsypenyuk, Draper, UT (US); Waina Michelle Chu, Tustin, CA (US); Alexander Barash, Tzoran (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/316,942

(22) Filed: May 12, 2023

(65) Prior Publication Data
US 2023/0277313 A1    Sep. 7, 2023

Related U.S. Application Data

(63) Continuation of application No. 17/316,885, filed on May 11, 2021, which is a continuation of application
(Continued)

(51) Int. Cl.
*A61F 2/24* (2006.01)
*A61F 2/90* (2013.01)

(52) U.S. Cl.
CPC .......... *A61F 2/2418* (2013.01); *A61F 2/2409* (2013.01); *A61F 2/2433* (2013.01);
(Continued)

(58) Field of Classification Search
None
See application file for complete search history.

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 0144167 C | 9/1903 |
| DE | 2246526 A1 | 3/1973 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Leslie A Lopez
(74) *Attorney, Agent, or Firm* — Klarquist Sparkman, LLP; Sean Seung Kyu Kim

(57) ABSTRACT

A prosthetic heart valve can include a radially expandable and compressible frame having an inflow end, an outflow end, and a plurality of struts. The prosthetic valve can further include a valvular structure comprising a plurality of leaflets, each leaflet comprising a coaptation edge portion and a cusp edge portion. The cusp edge portion of each leaflet can be folded toward the outflow end of the frame along a bending axis and a reinforcing member extends along an outflow surface of the cusp edge portion along the bending axis. The prosthetic heart valve can include a plurality of connecting skirts, each disposed between the cusp edge portion of an adjacent leaflet and the frame. First stitching secures the reinforcing member and the connecting skirts to (Continued)

the cusp edge portions and second stitching secures the connecting skirts to selected struts of the frame.

18 Claims, 40 Drawing Sheets

Related U.S. Application Data

No. 15/664,430, filed on Jul. 31, 2017, now Pat. No. 11,096,781.

(60) Provisional application No. 62/369,678, filed on Aug. 1, 2016.

(52) U.S. Cl.
CPC ............... *A61F 2/2412* (2013.01); *A61F 2/90* (2013.01); *A61F 2220/0075* (2013.01); *A61F 2230/0023* (2013.01); *A61F 2230/0052* (2013.01); *A61F 2250/0003* (2013.01); *A61F 2250/0039* (2013.01); *A61F 2250/0069* (2013.01); *A61F 2310/00017* (2013.01); *A61F 2310/00029* (2013.01); *A61F 2310/00059* (2013.01)

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavonik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,640,081 A | 6/1997 | Austin et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |

(56) References Cited

U.S. PATENT DOCUMENTS

| | | | |
|---|---|---|---|
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eldenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribler |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eldenschink et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,291,570 B2 | 10/2012 | Eldenschink et al. |
| 8,449,606 B2 | 5/2013 | Ellasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0186565 A1 | 9/2004 | Schreck |
| 2004/0260389 A1 | 12/2004 | Case et al. |
| 2005/0075724 A1 | 4/2005 | Svanidze et al. |
| 2005/0075728 A1 | 4/2005 | Nguyen et al. |
| 2005/0096736 A1 | 5/2005 | Osse et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259137 A1 | 11/2006 | Artof et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0073387 A1 | 3/2007 | Forster et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2007/0270944 A1 | 11/2007 | Bergheim et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0275537 A1 | 11/2008 | Limon |
| 2009/0125118 A1 | 5/2009 | Gong |
| 2009/0157175 A1* | 6/2009 | Benichou .............. A61F 2/2418 623/2.18 |
| 2009/0276040 A1 | 11/2009 | Rowe et al. |
| 2009/0281619 A1 | 11/2009 | Le et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0168844 A1 | 7/2010 | Toomes et al. |
| 2010/0185277 A1* | 7/2010 | Braido ................. A61F 2/2433 623/2.37 |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0319991 A1 | 12/2011 | Hariton et al. |
| 2012/0123529 A1* | 5/2012 | Levi ..................... A61F 2/2433 623/2.11 |
| 2012/0185038 A1 | 7/2012 | Fish et al. |
| 2012/0197391 A1 | 8/2012 | Alkhatib et al. |
| 2012/0259409 A1 | 10/2012 | Nguyen et al. |
| 2013/0023985 A1 | 1/2013 | Khairkhahan et al. |
| 2013/0150956 A1 | 6/2013 | Yohanan et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0157458 A1 | 6/2015 | Thambar et al. |
| 2015/0209136 A1 | 7/2015 | Braido et al. |
| 2020/0107929 A1 | 4/2020 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 3490501 A1 | 6/2019 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |

(56) References Cited

FOREIGN PATENT DOCUMENTS

| | | |
|---|---|---|
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005062980 A2 | 7/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2010011699 A2 | 1/2010 |
| WO | 2010121076 A2 | 10/2010 |
| WO | 2012032187 A1 | 3/2012 |
| WO | 2012048035 A2 | 4/2012 |
| WO | 2012177942 A2 | 12/2012 |
| WO | 2013106585 A1 | 7/2013 |
| WO | 2014110171 A2 | 7/2014 |
| WO | 2014139545 A1 | 9/2014 |
| WO | 2014210124 A1 | 12/2014 |
| WO | 2015085218 A1 | 6/2015 |
| WO | 2015173794 A1 | 11/2015 |
| WO | 2017035487 A1 | 3/2017 |
| WO | 2018026865 A1 | 2/2018 |

OTHER PUBLICATIONS

Bailey, S. "Percutaneous Expandable Prosthetic Valves," Textbook of Interventional Cardiology vol. 2, 2nd Ed. pp. 1268-1276. 1994.
H.R. Andersen "History of Percutaneous Aortic Valve Prosthesis," Herz No. 34. pp. 343-346. 2009.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Uchida, "Modifications of Gianturco Expandable Wire Stents," American Journal of Roentgenology, vol. 150. pp. 1185-1187. 1986.
Wheatley, "Valve Prostheses," Operative Surgery, 4th ed. pp. 415-424. 1986.

\* cited by examiner

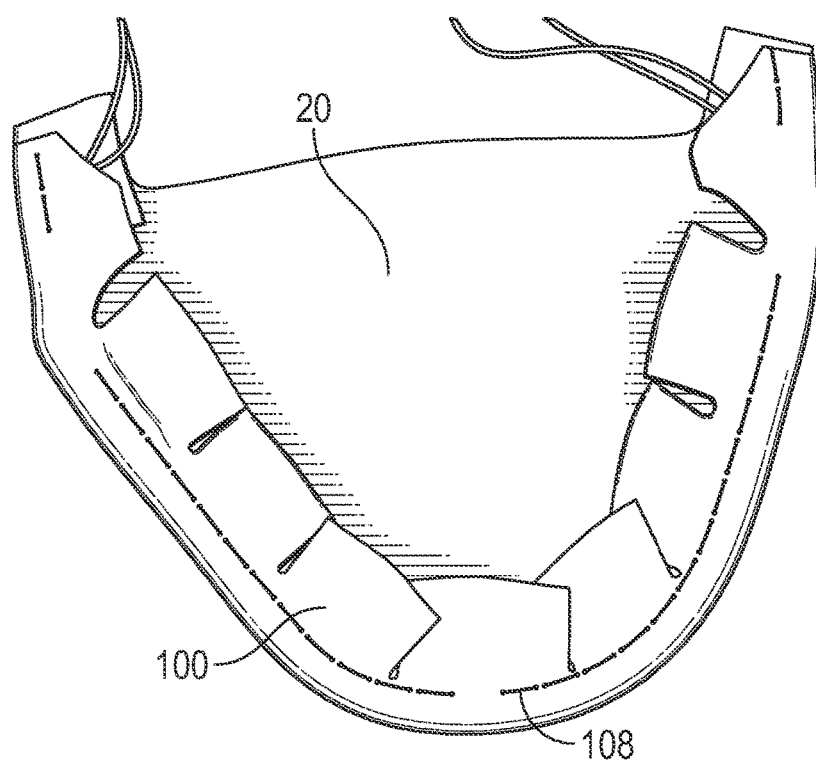
FIG. 11B
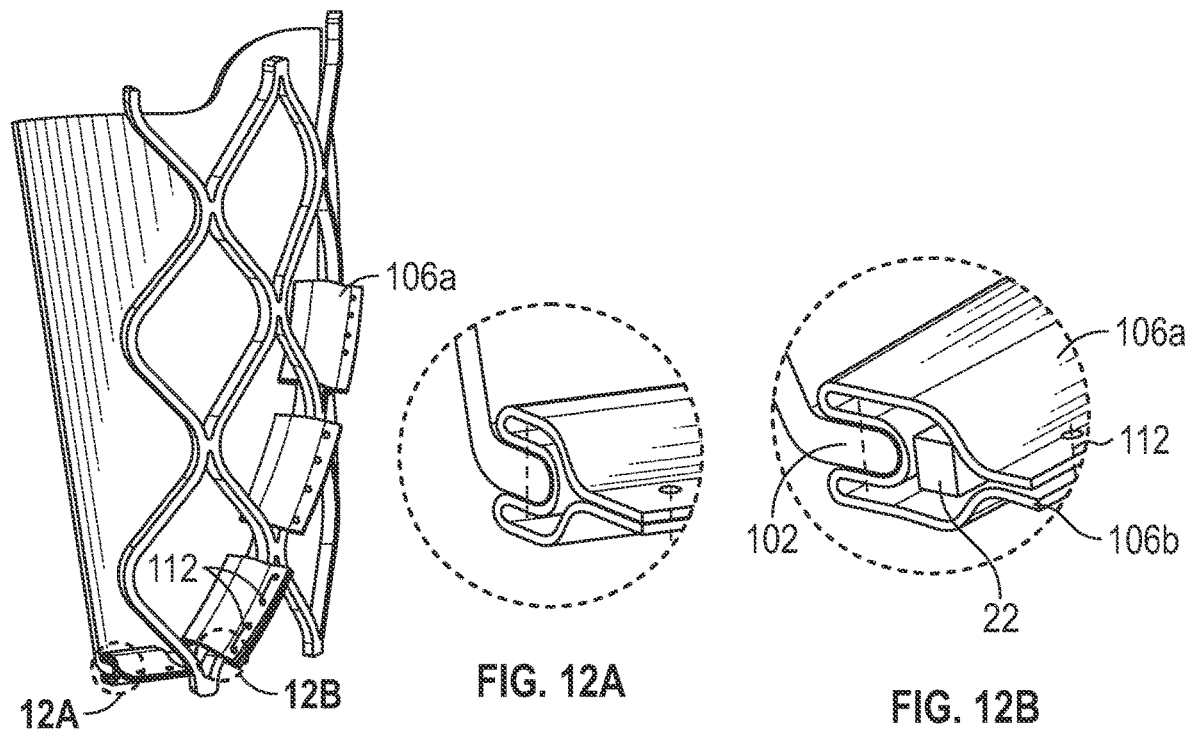
FIG. 12A
FIG. 12B
FIG. 12

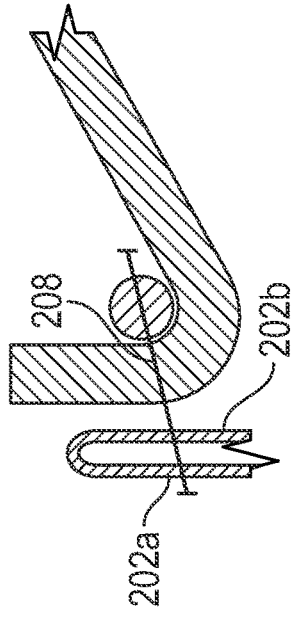
FIG. 28
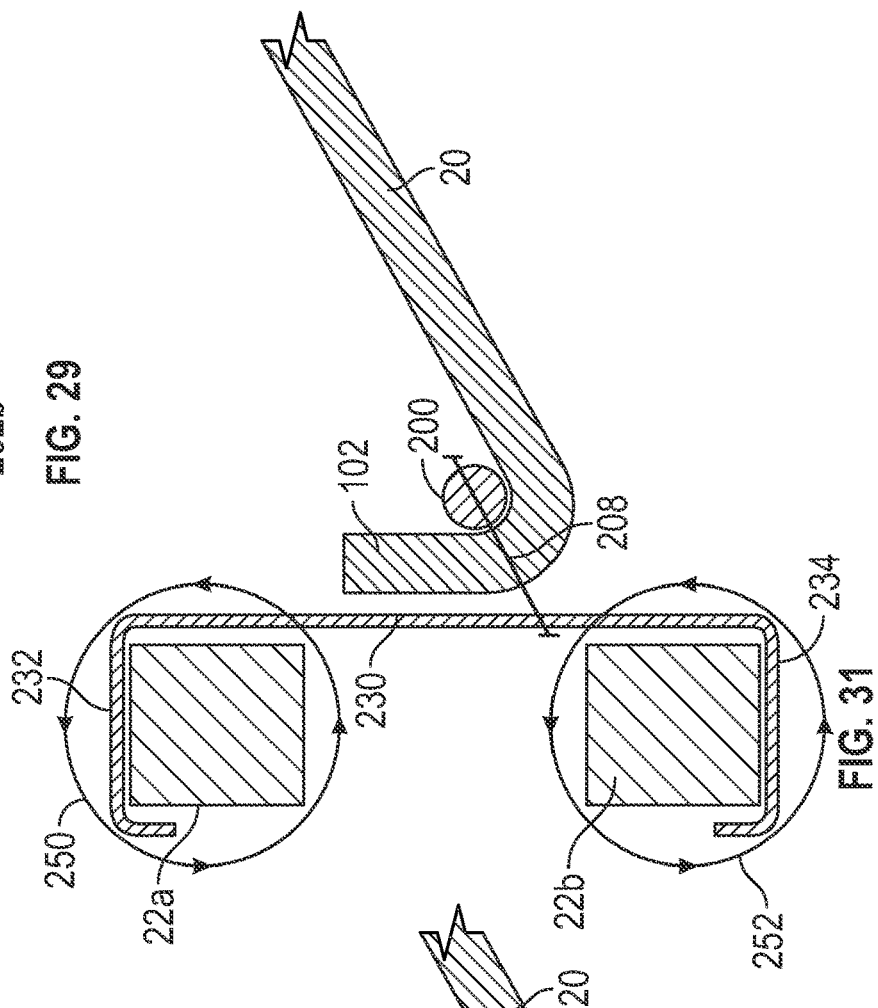
FIG. 29
FIG. 31
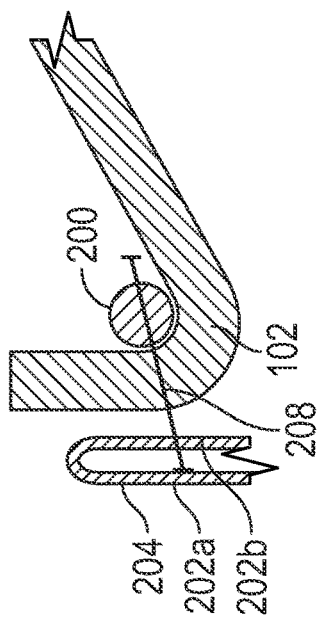
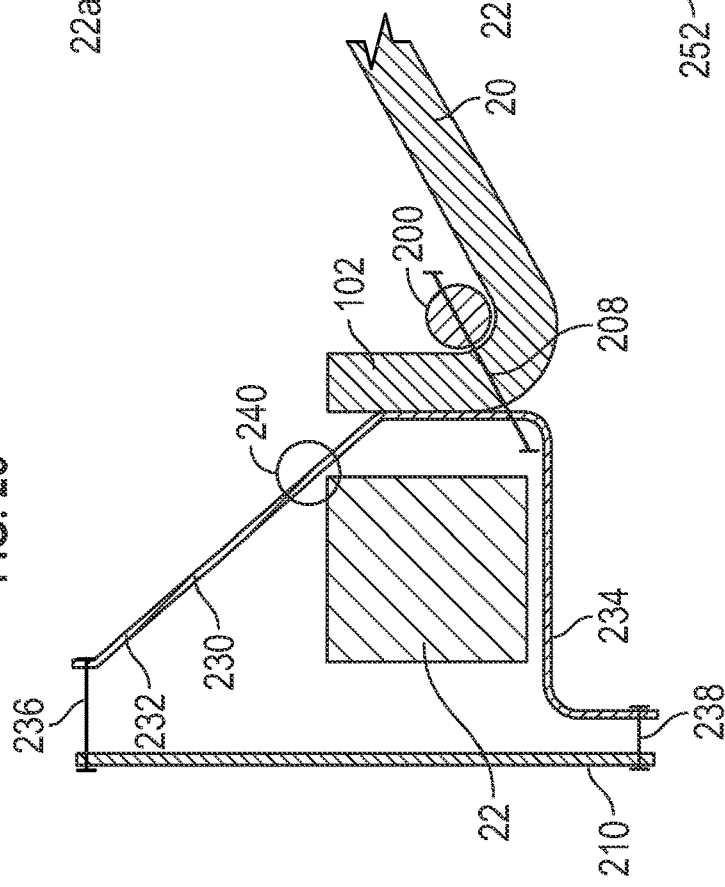
FIG. 30

PROSTHETIC HEART VALVE

CROSS-REFERENCE TO RELATED APPLICATIONS

The present application is a continuation of U.S. patent application Ser. No. 17/316,885, filed May 11, 2021, which is a continuation of U.S. patent application Ser. No. 15/664,430, filed Jul. 31, 2017, now U.S. Pat. No. 11,096,781, which claims the benefit of U.S. Provisional Application No. 62/369,678, filed Aug. 1, 2016, all of which applications are incorporated herein by reference.

FIELD

The present disclosure concerns embodiments of a prosthetic heart valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine". In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the diameter of the folded or crimped profile. The diameter of the crimped profile is important because it directly influences the physician's ability to advance the transcatheter heart valve through the femoral artery or vein. More particularly, a smaller profile allows for treatment of a wider population of patients, with enhanced safety. Another important design parameter is control of perivalvular leakage around the valve, which can occur for a period of time following initial implantation.

SUMMARY

In one representative embodiment, a prosthetic heart valve comprises an annular frame comprising an inflow end and an outflow end and being radially collapsible and expandable between a radially collapsed configuration and a radially expanded configuration, wherein the frame comprises a plurality of struts defining openings. The prosthetic heart valve can further comprise a valvular structure mounted within the frame and comprising a plurality of leaflets that regulate the flow of blood through the frame, wherein each leaflet comprises an inflow surface, an outflow surface, and a cusp edge portion that is fixed relative to the frame. The prosthetic heart valve can also comprise a sealing member mounted on the frame and comprising an inner layer and an outer layer. At least the outer layer is mounted on the outside of the frame, and the inner layer covers at least the openings in the frame between adjacent cusp portions of adjacent leaflets and the inner layer does not cover one or more openings in the frame at locations facing the outflow surfaces of the leaflets to permit retrograde blood to flow through the one or more uncovered openings in the frame and into space between the outer layer and the frame.

In some embodiments, the cusp edge portions of the leaflets have a curved, scalloped shape and the inner layer of the sealing member comprises a plurality of triangular shaped portions that are mounted on the frame at locations between adjacent cusp edge portions of adjacent leaflets.

In some embodiments, the inner layer does not cover any openings in the frame at locations facing the outflow surfaces of the leaflets.

In some embodiments, the inner layer is mounted on the outer surface of the frame.

In some embodiments, the inner layer is mounted on the inner surface of the frame.

In some embodiments, the outer layer is shape set such that it extends radially away from the frame when the frame is in the radially expanded configuration.

In some embodiments, the outer layer comprises a shape set fabric.

In some embodiments, the outer layer comprises a lower tapered wall section that extends outwardly from the frame in a direction from the inlet end to the outlet end, an upper tapered wall section that extends outwardly from the frame in a direction from the outlet end to the inlet end, and a central wall section that extends between the lower and upper tapered wall sections.

In some embodiments, the cusp edge portion of each leaflet is fixed relative to the frame by a connecting skirt that is connected to and disposed between the frame and the cusp edge portion of the leaflet, wherein each connecting skirt is sutured to struts of the frame extending in a diagonal line from the inlet end to the out end of the frame.

In some embodiments, wherein each connecting skirt comprises two layers of material sutured to the cusp edge portion of a leaflet and to struts of the frame.

In some embodiments, each leaflet comprises opposing upper tabs on opposite sides of the leaflet and opposing lower tabs on opposite sides of the leaflets below the upper tabs, wherein each upper tab is paired with an adjacent upper tab of an adjacent leaflet to form a plurality of commissures, and wherein each lower tab is folded to form at least one fold layer along the cusp edge portion of the respective leaflet.

In some embodiments, each leaflet is unattached to the frame at locations between the upper tabs and the lower tabs.

In some embodiments, each leaflet is formed with a gap between the upper tab and the lower tab on each side of the leaflet.

In some embodiments, at least one reinforcing chord extends along the cusp edge portion of each leaflet and underneath each commissure.

In another representative embodiment, a prosthetic heart valve comprises an annular frame comprising an inflow end and an outflow end and being radially collapsible and expandable between a radially collapsed configuration and a radially expanded configuration. The prosthetic heart valve can also comprise a valvular structure mounted within the frame and comprising a plurality of leaflets that regulate the flow of blood through the frame. Each leaflet can comprise opposing upper tabs on opposite sides of the leaflet, opposing lower tabs on opposite sides of the leaflets below the upper tabs, a cusp edge portion extending between the lower tabs, the cusp edge portion being fixed relative to the frame, wherein each upper tab is paired with an adjacent upper tab of an adjacent leaflet to form a plurality of commissures that are fixed relative to the frame, and wherein each lower tab is folded to form at least one fold layer along the cusp edge portion of the respective leaflet.

In some embodiments, opposing side edges of the leaflets between the upper tabs and the lower tabs are unattached to the frame.

In some embodiments, the opposing side edges of the leaflets are formed with gaps between the upper tabs and the lower tabs where the side edges are unattached to the frame.

In some embodiments, the prosthetic heart valve can comprise a sealing member mounted on the frame and comprising an inner layer and an outer layer, wherein at least the outer layer is mounted on the outside of the frame, and the inner layer covers at least openings in the frame between adjacent cusp edge portions of adjacent leaflets and the inner layer has uncovered areas at locations facing the outflow surfaces of the leaflets to permit retrograde blood to flow through the openings in the frame and into space between the outer layer and the frame.

In some embodiments, a reinforcing chord extends along and is secured to the cusp edge portion of each leaflet and the at least one fold layer of each lower tab.

In another representative embodiment, a prosthetic heart valve comprises an annular frame comprising an inflow end and an outflow end and being radially collapsible and expandable between a radially collapsed configuration and a radially expanded configuration. The prosthetic heart valve can further include a valvular structure mounted within the frame and comprising a plurality of leaflets that regulate the flow of blood through the frame. Each leaflet can comprise opposing tabs on opposite sides of the leaflet and a cusp edge portion between the tabs, the cusp edge portion being fixed relative to the frame, wherein each tab is paired with an adjacent tab of an adjacent leaflet to form a plurality of commissures that are fixed relative to the frame, and wherein each leaflet has opposing edges between the tabs and the cusp edge portions that are unattached to the frame, allowing blood to flow between the frame and the unattached edges.

In some embodiments, the unattached edges are spaced radially inwardly of the frame.

In some embodiments, the tabs of each leaflet comprise upper tabs that are paired with adjacent upper tabs of adjacent leaflets to form the commissures, and each leaflet further comprises opposing lower tabs on opposite sides of the leaflets below the upper tabs, the lower tabs being spaced from the upper tabs by the unattached edges, wherein the lower tabs are folded against the cusp edge portion of the leaflet.

In some embodiments, a reinforcing chord extends along and secured to the cusp edge portion of each leaflet and traverses the space underneath each commissure.

In some embodiments, each unattached edge of a leaflet can coapt with an adjacent unattached edge of an adjacent leaflet under the flow of retrograde blood and can separate from the adjacent unattached edge under the flow of antegrade blood.

In another representative embodiment, a prosthetic heart valve comprises an annular frame comprising an inflow end and an outflow end and being radially collapsible and expandable between a radially collapsed configuration and a radially expanded configuration. The prosthetic heart valve can further comprise a valvular structure mounted within the frame and comprising a plurality of leaflets that regulate the flow of blood through the frame, wherein each leaflet comprises opposing tabs on opposite sides of the leaflet and a cusp edge portion between the tabs, wherein each tab is paired with an adjacent tab of an adjacent leaflet to form a plurality of commissures that are connected to the frame. The cusp edge portion of each leaflet can connected to the frame by a connecting skirt that is connected to and disposed between the frame and the cusp edge portion of the leaflet, wherein each connecting skirt is sutured to struts of the frame extending in a diagonal line from the inlet end to the out end of the frame.

In some embodiments, the cusp edge portion of each leaflet is folded toward the outlet end of the frame.

In some embodiments, each connecting skirt is sutured to the cusp edge portion of a leaflet and to the frame.

In some embodiments, a reinforcing chord is secured to each cusp edge portion opposite a respective connecting skirt, the reinforcing chord defining a bending axis for a respective leaflet.

In some embodiments, each connecting skirt prevents the cusp edge portion of a respective leaflet from contacting the inner surface of the frame.

In some embodiments, the cusp edge portions are not supported by any metal components inside the frame.

In some embodiments, each connecting skirt comprises two layers of material sutured to the cusp edge portion of a leaflet and to the frame.

In some embodiments, each connecting skirt supports the cusp edge portion of a leaflet at a location spaced radially inwardly from the inner surface of the frame.

In another representative embodiment, a prosthetic heart valve comprises an annular frame comprising an inflow end and an outflow end and being radially collapsible and expandable between a radially collapsed configuration and a radially expanded configuration, wherein the frame comprises a plurality of struts defining openings. The prosthetic heart valve can include a valvular structure mounted within the frame and comprising a plurality of leaflets that regulate the flow of blood through the frame, wherein each leaflet comprises an inflow surface, an outflow surface, opposing upper tabs on opposite sides of the leaflet, opposing lower tabs on opposite sides of the leaflets below the upper tabs, a cusp edge portion extending between the lower tabs. Each upper tab can be paired with an adjacent upper tab of an adjacent leaflet to form a plurality of commissures that are fixed relative to the frame, and each lower tab can be folded to form at least one fold layer along the cusp edge portion of the respective leaflet. The cusp edge portion of each leaflet can be connected to the frame by a connecting skirt that is connected to and disposed between the frame and the cusp edge portion of the leaflet, wherein each connecting skirt is sutured to struts of the frame extending in a diagonal line from the inlet end to the out end of the frame. Each leaflet can have opposing edges between the upper tabs and the lower tabs that are unattached to the frame, with the unattached edges being spaced radially inwardly of the frame, allowing blood to flow between the frame and the unattached edges. The prosthetic heart valve can also include a sealing member mounted on the frame and comprising an inner layer and an outer layer. At least the outer layer is mounted on the outside of the frame, and the inner layer covers at least the openings in the frame between adjacent cusp portions of adjacent leaflets and the inner layer does not cover one or more openings in the frame at locations facing the outflow surfaces of the leaflets to permit retrograde blood to flow through the one or more uncovered openings in the frame and into space between the outer layer and the frame.

BRIEF DESCRIPTION OF THE DRAWINGS

FIGS. 10, 10A, 11A, and 11B are various views showing the attachment of the connecting skirt and the leaflet of FIG. 9.

FIGS. 12, 12A, and 12B are various views showing the connection of the connecting skirt of FIG. 9 to the frame of the prosthetic valve of FIG. 8.

FIGS. 25A, 25B, 26, 27, 28, 29, 30, 31, and 32 show alternative ways of connecting the cusp edge portion of a leaflet to a frame of a prosthetic heart valve, with and without a connecting skirt.

DETAILED DESCRIPTION

Figure 1A:
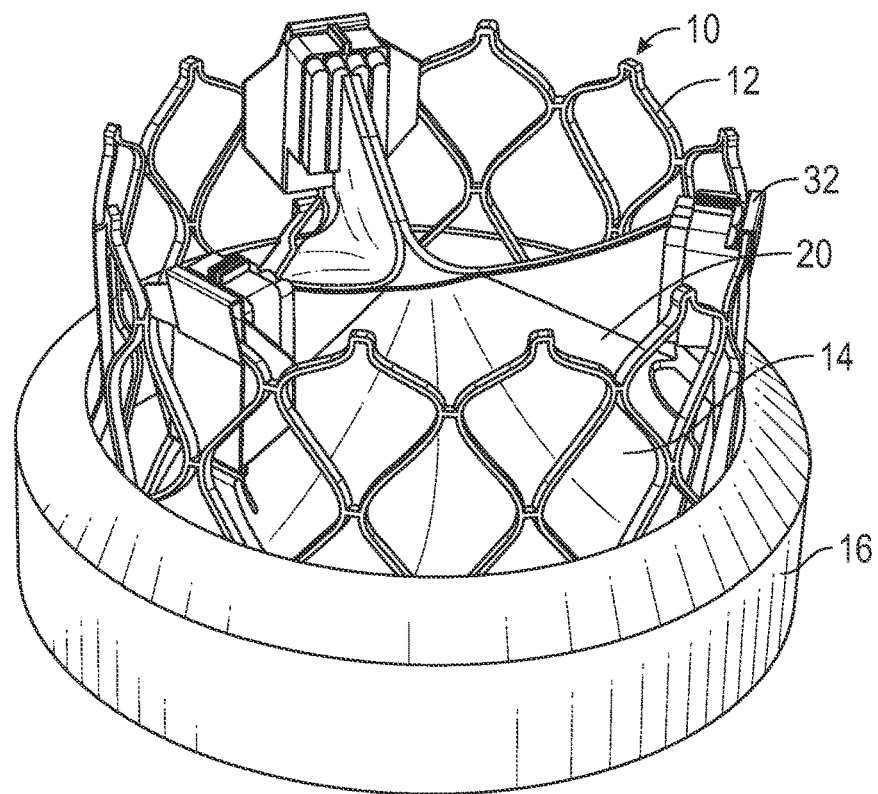
FIGS. 1A-1B are perspective views of a prosthetic heart, according to one embodiment.

The present disclosure concerns embodiments of implantable prosthetic devices and, in particular, implantable prosthetic valves, and methods for making such devices. In particular embodiments, the prosthetic device comprises a prosthetic heart valve, and can be configured to be implanted in any of the native heart valves (aortic, mitral, pulmonary, and tricuspid). In addition, the prosthetic heart valve can be, for example, a transcatheter heart valve, a surgical heart valve, or a minimally-invasive heart valve. The prosthetic valve also can comprise other types of valves implantable within other body lumens outside of the heart or heart valves that are implantable within the heart at locations other than the native valves, such as trans-atrial or trans-ventricle septum valves.

The disclosed prosthetic heart valves are particularly suited for implantation in the native aortic valve. In the context of a prosthetic aortic valve, the terms "lower" and "upper" are used interchangeably with the terms "inflow" and "outflow", respectively, for convenience. Thus, for example, the lower end of the prosthetic valve is its inflow end and the upper end of the prosthetic valve is its outflow end in the orientation shown in the drawings. However, it should be understood that the prosthetic valve can be implanted in the reverse orientation. For example, for implantation at the mitral valve position, the upper end of the prosthetic valve is the inflow end and the lower end of the valve is the outflow end.

Figure 1B:
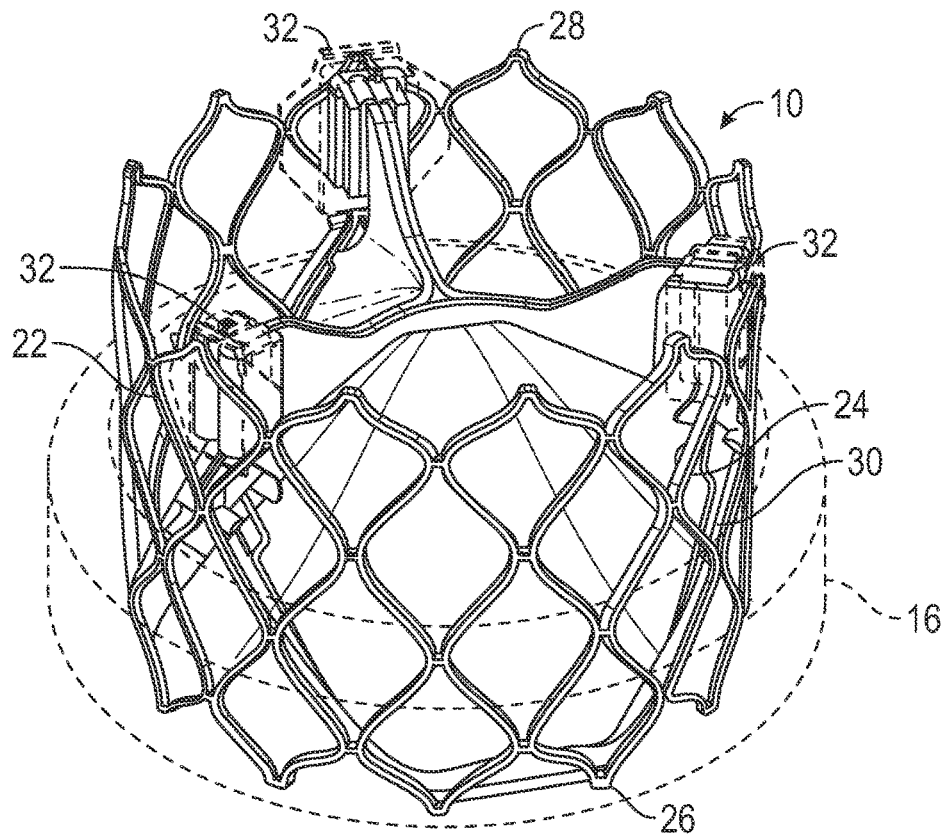

FIG. 1A is a perspective view of a prosthetic heart valve 10, according to one embodiment. The illustrated valve is adapted to be implanted in the native aortic annulus, although in other embodiments it can be adapted to be implanted in the other native annuluses of the heart. The valve 10 can have three main components: a stent, or frame, 12, a valvular structure 14, and a sealing member 16. FIG. 1B is a perspective view of the prosthetic valve 10 with the components on the outside of the frame 12 (including the sealing member 16) shown in transparent lines for purposes of illustration.

The valvular structure 14 can comprise three leaflets 20, collectively forming a leaflet structure, which can be arranged to collapse in a tricuspid arrangement, although in other embodiments there can be greater or fewer number of leaflets (e.g., one or more leaflets 20). The lower edge of leaflet structure 14 desirably has an undulating, curved scalloped shape. By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 20 can be formed of pericardial tissue (e.g., bovine or porcine pericardial tissue), biocompatible synthetic materials, or various other suitable natural or synthetic materials as known in the art and described in U.S. Pat. No. 6,730,118, which is incorporated by reference herein.

Each leaflet 20 can be coupled to the frame 12 along its inflow edge 30 (the lower edge in the figures; also referred to as "cusp edges") and at commissures 32 of the valvular structure 14 where adjacent portions of two leaflets are connected to each other, as further described below.

The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the prosthetic valve 10) can be crimped to a radially compressed state on a delivery catheter and then expanded inside a patient by an inflatable balloon or any suitable expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the prosthetic valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

The frame 12 in the illustrated embodiment comprises a plurality of circumferentially extending rows of angled struts 22 defining rows of cells, or openings, 24 of the frame. The frame 12 can have a cylindrical or substantially cylindrical shape having a constant diameter from an inflow end 26 to an outflow end 28 of the frame as shown, or the frame can vary in diameter along the height of the frame, as disclosed in US Publication No. 2012/0239142, which is incorporated herein by reference.

The sealing member 16 in the illustrated embodiment is mounted on the outside of the frame 12 and functions to create a seal against the surrounding tissue (e.g., the native leaflets and/or native annulus) to prevent or at least minimize paravalvular leakage. The sealing member 16 can comprise an inner layer 34 (which can be in contact with the outer surface of the frame 12) and an outer layer 36. The sealing member 16 can be connected to the frame 12 using suitable techniques or mechanisms. For example, the sealing member 16 can be sutured to the frame 12 via sutures 38 that can extend around the struts 22 and through the inner layer 34. In alternative embodiments, the inner layer 34 can be mounted on the inner surface of the frame 12, while the outer layer 36 is on the outside of the frame.

Figure 3:
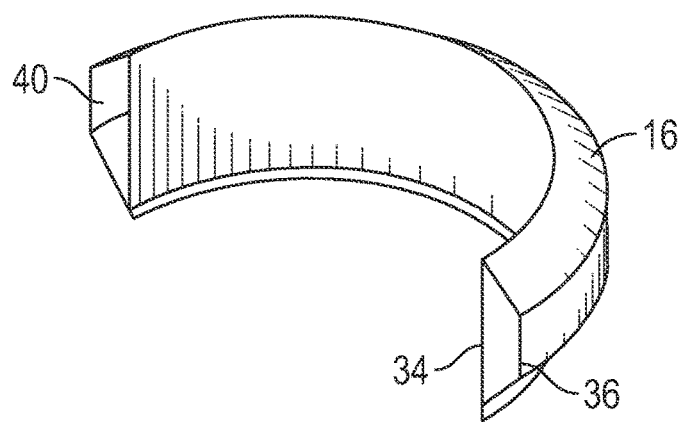
FIG. 3 is a perspective, sectional view of the sealing member of FIG. 1.

The outer layer 36 can be configured or shaped to extend radially outward from the inner layer 34 and the frame 12 when the prosthetic valve 10 is deployed. As best shown in FIG. 3, when the prosthetic valve is fully expanded outside of a patient's body, the outer layer 36 can expand away from the inner layer 34 to create a space 40 between the two layers. Thus, when implanted in the body, this allows the outer layer 36 to expand into contact with the surrounding tissue.

In the illustrated embodiment, the outer layer 36 comprises a lower tapered wall section 36a that extends outwardly from the frame in a direction from the inlet end to the outlet end, an upper tapered wall section 36b that extends outwardly from the frame in a direction from the outlet end to the inlet end, and a central wall section 36c that extends between the lower and upper tapered wall sections. The central wall section 36c can extend parallel to the longitudinal axis of the prosthetic valve as shown. In alternative embodiments, the upper and lower wall sections can extend perpendicularly relative to the longitudinal axis of the prosthetic valve. In alternative embodiments, the outer layer 36 can be formed by connecting together (such as by stitching) separate fabric components (for example, separate pieces of material for each wall section 36a, 36b, 36c) to form a three-dimensional structure without shape setting.

Figure 4:
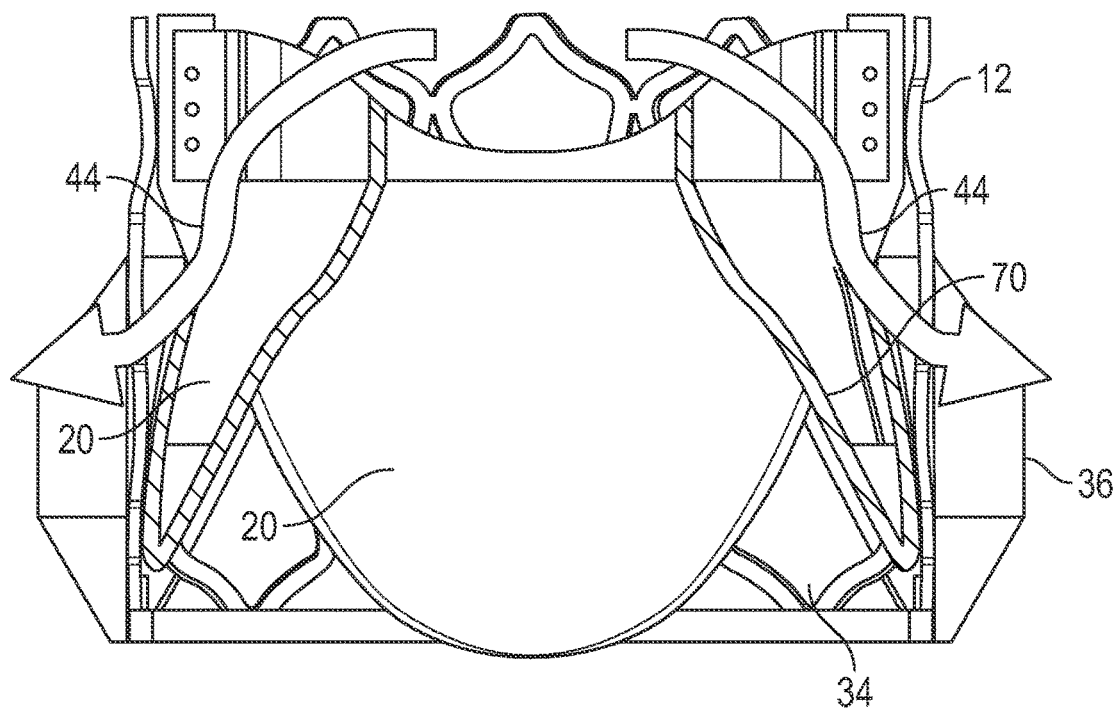
FIG. 4 is a cross-sectional view of the prosthetic heart valve of FIG. 1, showing the flow of retrograde blood through the valve.
Figure 5:
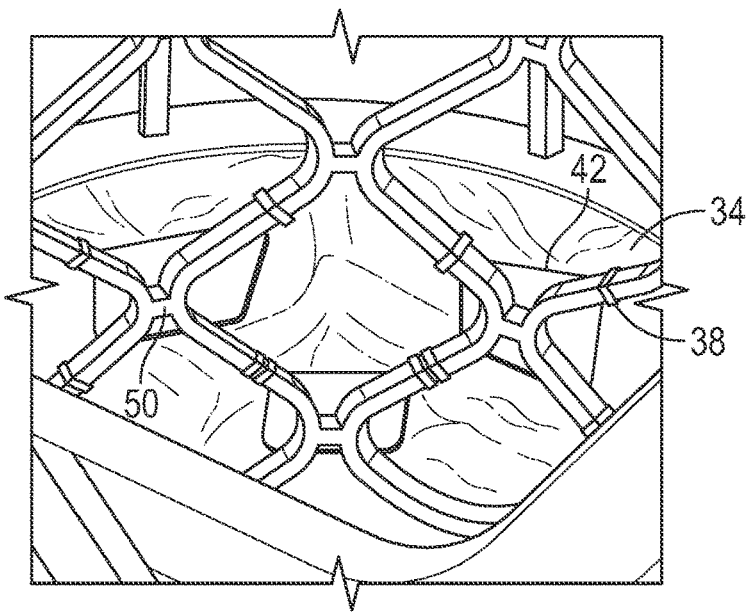
FIG. 5 is an enlarged perspective view showing a portion of the inside of the prosthetic heart valve of FIG. 1.

The inner layer 34 desirably is formed with at least one aperture or opening, and more desirably a plurality of apertures, or openings, 42 (FIG. 5). As best shown in FIG. 4, retrograde blood (indicated by arrows 44) can flow along the outside of the leaflets 20, through the cells 24 of the frame, through the openings 42 in the inner layer 34 and into the space 40 between the inner and outer layers 34, 36, to facilitate expansion of the sealing member 16 and creating a seal against the surrounding tissue. In some embodiments, the outer layer 36 can be formed with a plurality of apertures, or openings, which can allow blood to flow into the sealing member at least during valve deployment.

In the illustrated embodiment, the inner layer 34 is formed with one or more openings 42 along the portions of the inner layer that face the outflow surface 70 of the leaflets (the areas of the frame between the commissures) to allow retrograde blood to flow through the frame at those locations. The portions of the inner layer 34 covering the frame in the areas between the cusp edge portions of the leaflets completely cover the openings in the frame at those locations to prevent antegrade blood from flowing through the frame at those locations. In alternative embodiments, the inner layer can have portions that cover the areas of the frame between the cusp edge portions of the frame and cut-out sections along the portions of the frame facing the outflow surface of the leaflets (see the sealing members 702, 802, described below).

As shown in FIG. 5, the openings 42 can be centered at junctions 50 where the frame struts 22 intersect, which inhibits material of the inner layer 34 surrounding the openings from protruding inwardly through the frame and contacting the leaflets.

The sealing member 16 can be formed from fabric or non-fabric materials such as PET, PTFE, ePTFE, polyurethane, silicone, polyester, wire mesh, natural tissue (e.g., pericardium) and/or other suitable materials configured to restrict and/or prevent blood-flow therethrough. In some embodiments, the sealing member can be formed from a generally flat strip, folded lengthwise to form the inner and outer layers, and then formed into a tube, such as by welding or stitching the ends together. In other embodiments, the sealing member 16 can be formed by weaving, knitting, or braiding the sealing member into a tubular shape. The bulge in the outer layer 36 can be formed, for example, by shape-setting the material to a desired configuration (e.g., as shown in FIGS. 1 and 2). The shape-setting of the outer layer can allow the outer layer to be self-expandable or induce radial expansion of the outer layer. Additionally or alternatively, the outer layer 36 can be self-expandable by including Nitinol threads in the outer layer.

In alternative embodiments, the inner layer 34 does not have any openings 42, but can be formed from a porous material that allows blood to flow through the inner layer. For example, in some embodiments, the inner layer 34 can be formed from a relatively more porous material than the outer layer 36. In further alternative embodiments, the outer layer 36 need not be configured to extend away from the outer surface of the frame and instead can have a shape that conforms to the outer surface of the frame. For example, the outer layer 36 can be generally tubular to correspond to the shape of the frame 12. In some embodiments, the outer layer can be formed from a fabric having a pile layer (e.g., a velour fabric) having fibers or yarns forming looped or cut piles that help seal against the surrounding tissue. Sealing members formed from such fabrics are further described in U.S. Application No. 62/513,348, filed May 31, 2017, which is incorporated herein by reference.

Figure 6:
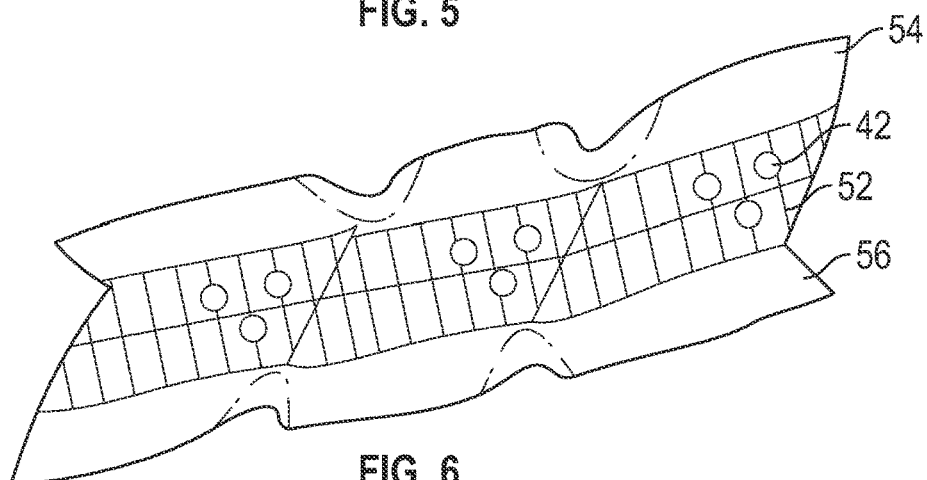
FIG. 6 shows a strip of fabric that can be used to form a sealing member, such as the sealing member of FIG. 3.

FIG. 6 shows a strip of fabric that can be used to form the sealing member 16, according to one embodiment. As shown, a fabric strip can comprise a center section 52 and first and second longitudinal edge portions 54, 56 extending along opposing sides of the center section 52. The center section 52 can include three sets of one or more openings 42 (e.g., three openings in each set in the illustrated embodiment). The openings 42 are positioned to correspond with the position of junctions 50 below the commissures of the prosthetic valve. The first and second longitudinal edge portions 54, 56 can be folded over the center portion 52 and secured to each other, such as with stitching, to form the sealing member. The longitudinal edge portions 54, 56 collectively form the outer layer 36, while the center portion 52 forms the inner layer 34.

Figure 7A:
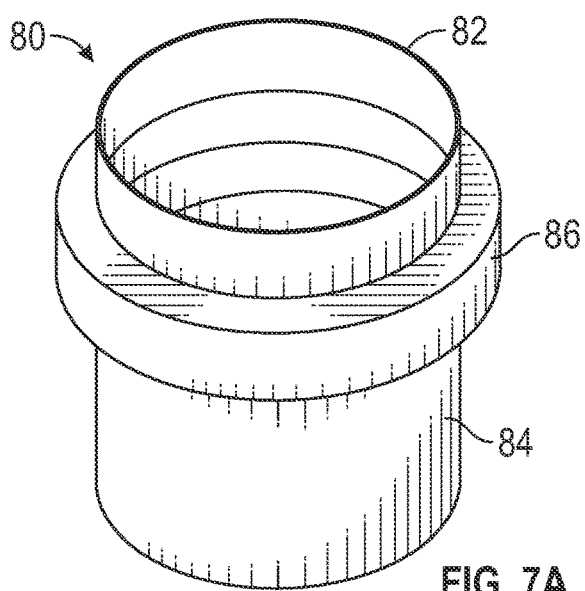
FIGS. 7A-7B are perspective views of exemplary tubular bodies that can be used to form a sealing member for a prosthetic heart valve.
Figure 7B:
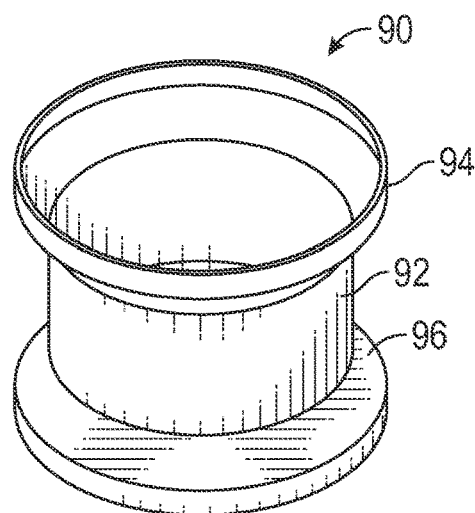

FIGS. 7A and 7B are perspective views of exemplary tubular bodies that can be used to form a sealing member 16. Referring to FIG. 7A, a tubular body 80 can comprise an upper portion 82 and a lower portion 84. The upper portion 82 can include a radial bulge 86. The tubular body 80 can be formed, for example, by three-dimensional weaving, knitting, or braiding. The lower portion 84 can be folded or inverted into the upper portion 82 to form a sealing member having an outer layer formed by the upper portion 82 and an inner layer formed from the lower portion 84.

Referring to FIG. 7B, a tubular body 90 can comprise a cylindrical central portion 92, a flared upper portion 94, and a flared lower portion 96. The tubular body 90 can be formed, for example, by three-dimensional weaving, knitting, or braiding. The upper portion 94 can folded or inverted over the lower portion 94 to form two layers of a sealing member.

Figure 8:
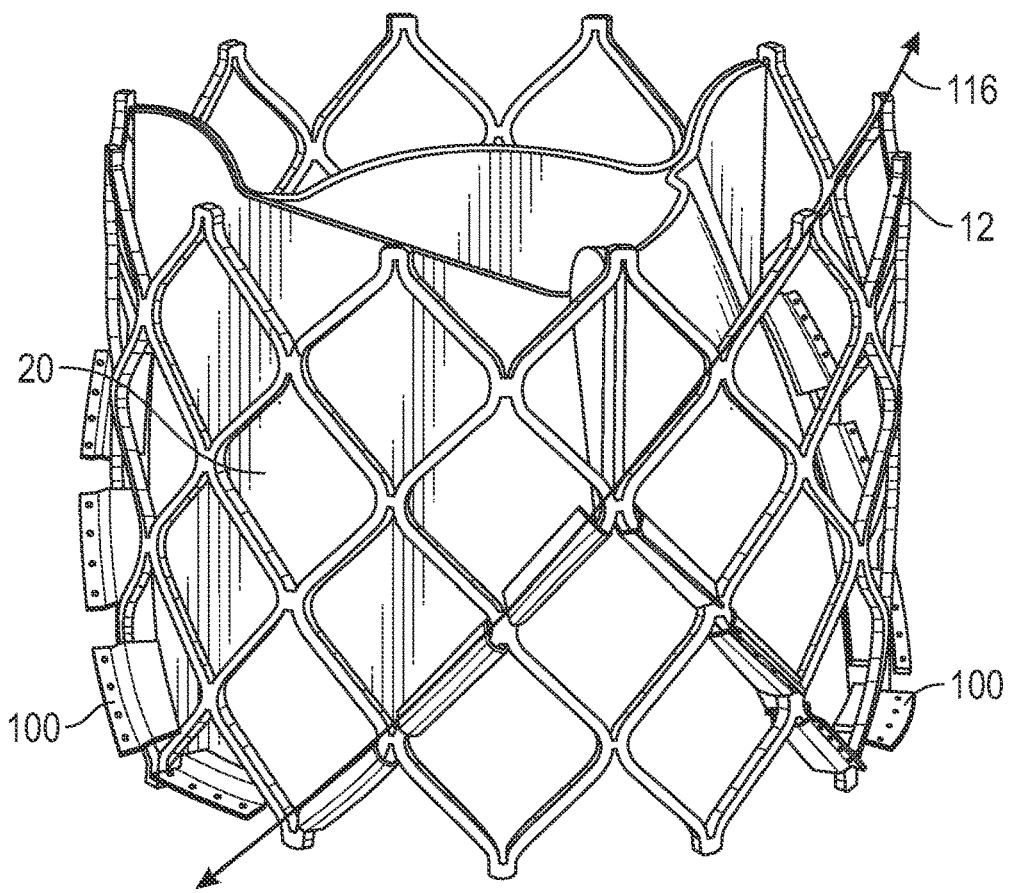
FIG. 8 is a perspective view of a partially assembled prosthetic heart valve showing the attachment of leaflets using connecting skirts, according to one embodiment.
Figure 9:
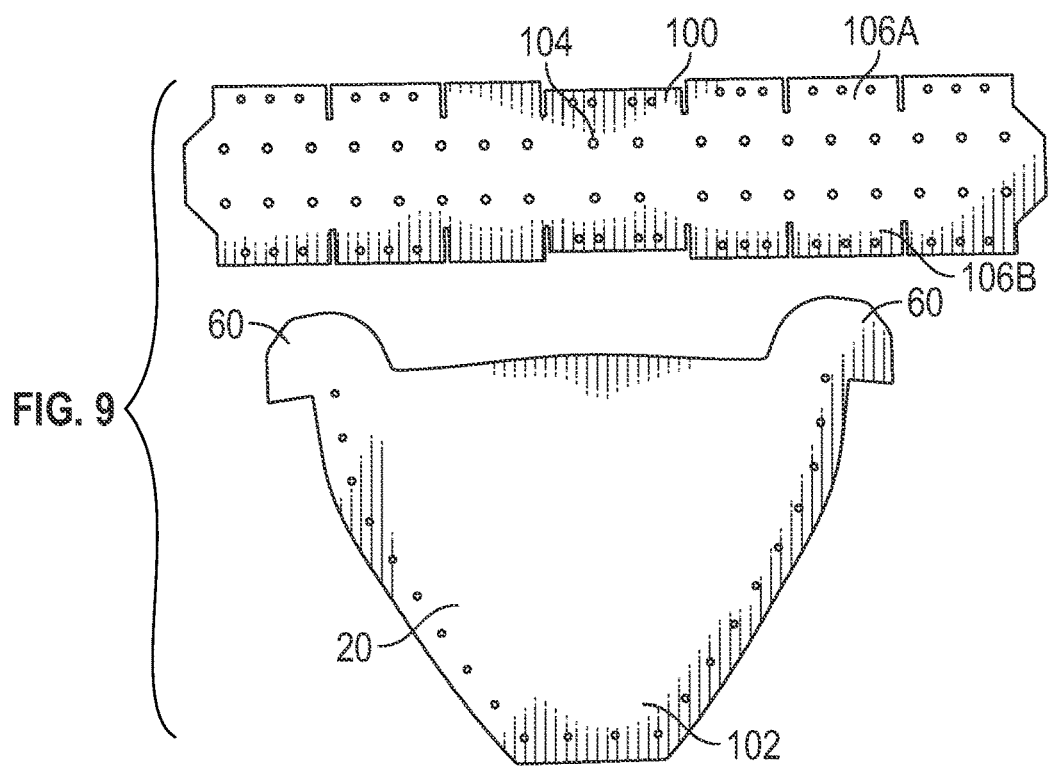
FIG. 9 is a plan view of a leaflet and a connecting skirt used in the prosthetic heart valve of FIG. 8.

FIGS. 8-13 illustrate a technique for mounting the inflow edges 30 of the leaflets 20 to the frame 12, according to one embodiment. In the illustrated embodiment, a connecting skirt 100 is secured to a lower edge portion 102 (also referred to as a cusp edge portion) of each leaflet. As best shown in FIG. 9, each connecting skirt 100 can comprise an elongated, generally rectangular body 104 formed with a plurality of flaps 106a, 106b formed along opposing longitudinal edges of the body 104. The skirt 100 can comprise any suitable synthetic material (e.g., PET) or natural tissue.

Figure 10:
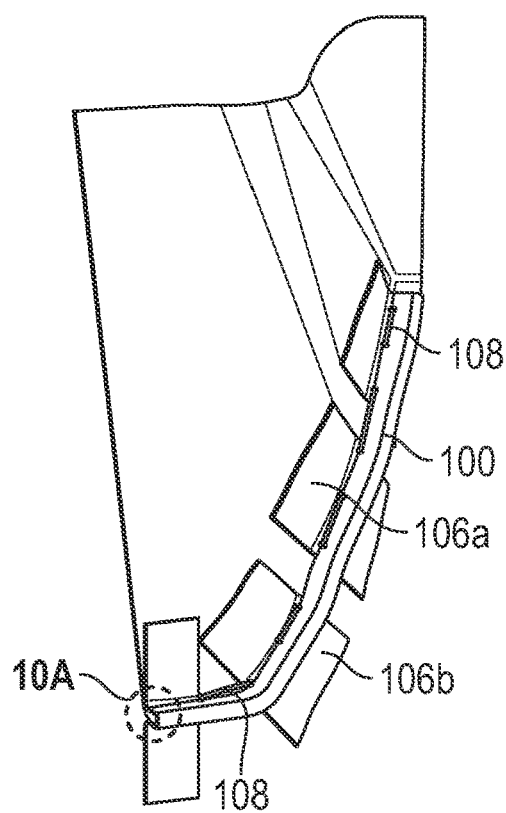
Figure 10A:
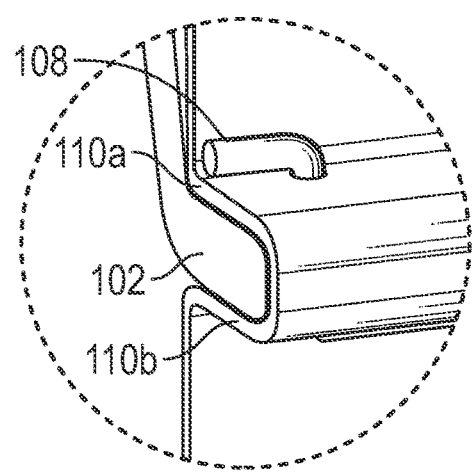
Figure 11A:
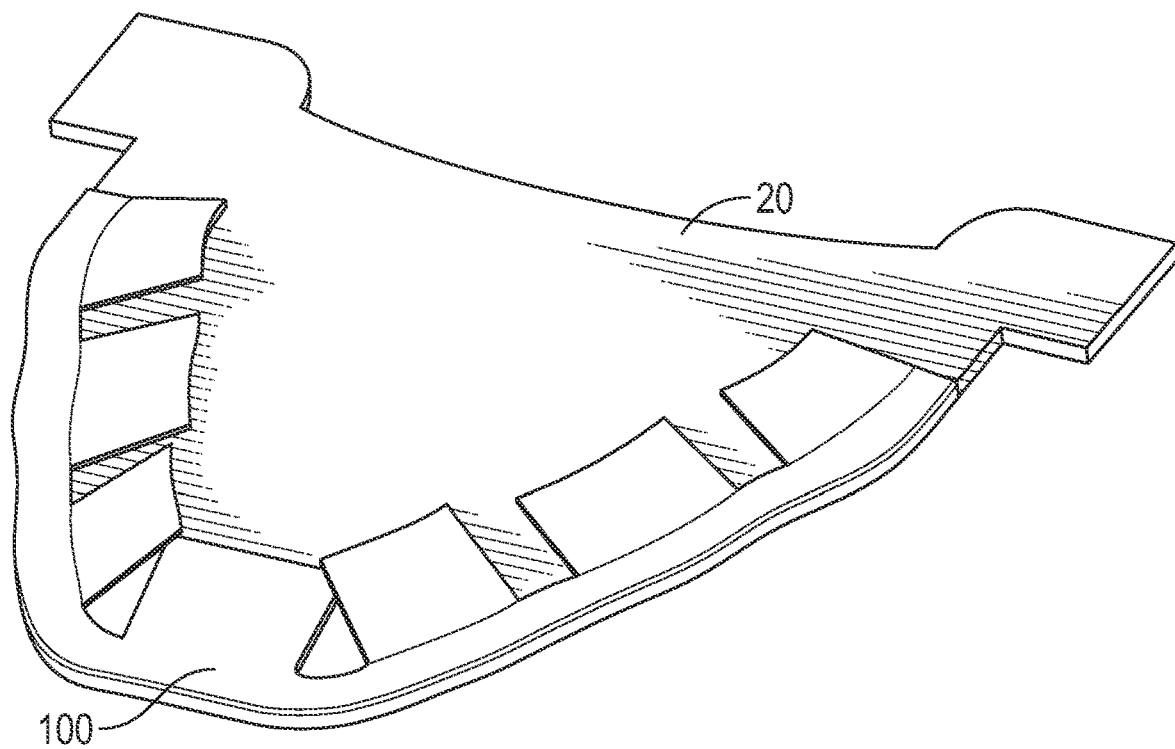

Referring to FIGS. 10 and 10A, to secure a connecting skirt 100 to a leaflet 20, the body 104 is folded along a central longitudinal fold bisecting the body to form folded portions 110a, 110b, which are then placed on opposite sides of the lower edge portion 102 of the leaflet 20 such that the flaps 106a are adjacent the outer surface of the leaflet and the flaps 106b are adjacent the inner surface of the leaflet. A suture can then be used to form stitches 108 that extend through the opposing portions 110a, 110b of the body 104 and the lower edge portion 102 of the leaflet and longitudinally along the length of the lower edge portion 102. FIG. 11A shows a flattened view of the leaflet 20 with the skirt 100 folded around the lower edge portion 102 of the leaflet. FIG. 11B shows a flattened view of the leaflet 20 and the skirt 100 after being secured to the leaflet with stitches 108.

Referring to FIGS. 12, 12A, and 12B, each pair of flaps 106a, 106b are folded away from the leaflet 20 over a respective strut 22 of the frame and secured in place with stitches 112 that extend through the flaps 106a, 106b along a stitching line outside of the frame 12. As best shown in FIG. 12B, the connecting skirt 100 mounts the leaflet to the frame 12 such that the lower edge portion 102 extends radially inwardly at about a 90-degree angle relative to the frame 12. This effectively moves the bending axis of the lower edge portion 102 inwardly away from the inner surface of the frame and toward the center of the frame.

As best shown in FIG. 8, each of the skirts 100 is secured to the frame along a diagonal line 116 extending along the curved surface of the frame defined by a diagonally extending row of struts 22 extending from the inflow end of the frame toward the outflow end. As such, the lower edge portion 102 of each leaflet is also positioned along a respective diagonal line 116 defined by a respective diagonally extending row of struts 22. This advantageously reduces tension and the formation of wrinkles in the leaflets 20.

The attachment along diagonal lines 116 also helps reduce the crimping profile of the prosthetic valve when the prosthetic valve is radially compressed to its delivery configuration. In particular, struts in a circumferentially extending row of struts of the frame are moved or bent toward each other during the crimping process while struts lying along diagonally extending lines 116 substantially retain their alignment relative to each other along lines 116 during the crimping process. As such, the connecting skirts 100 (which typically are formed from non-stretchable materials) do not inhibit movement or deformation of the struts relative to each other. Also, since the cusp edge portions of the leaflets move with the connecting skirts during crimping, stretching of the leaflets along the cusp edge portions is prevented or at least minimized.

Figure 13A:
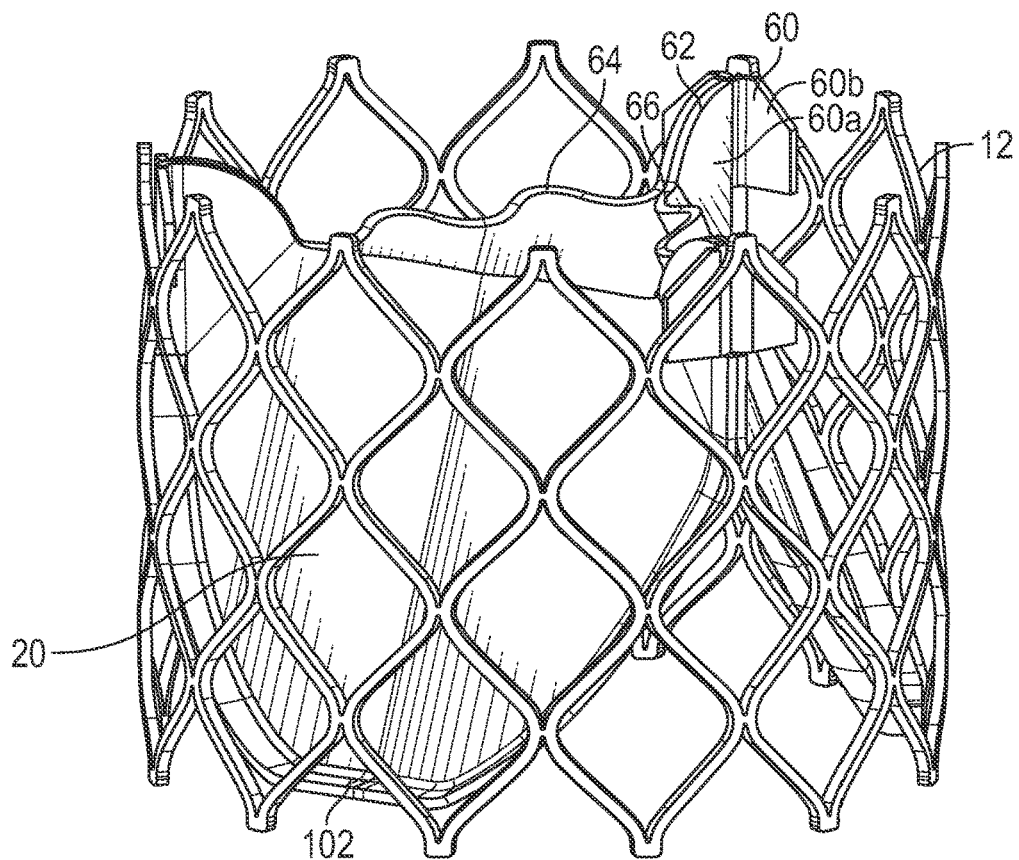
FIG. 13A is a perspective view of a frame of a prosthetic heart valve and leaflets mounted inside the frame, according to one embodiment.
Figure 13B:
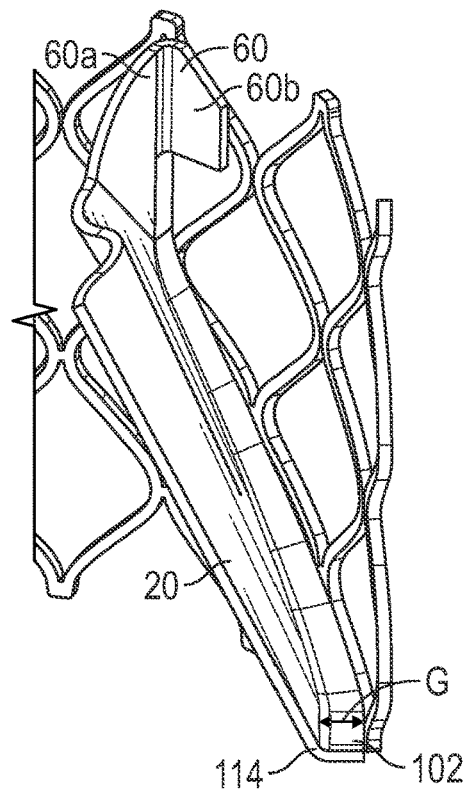
FIG. 13B is an enlarged view of a portion of the frame and one of the leaflets of FIG. 13A.

FIG. 13A is a perspective view of the frame 12 and the leaflets 20 supported in the frame shown in their mounted configuration with the connecting skirts 100 removed for purposes of illustration. FIG. 13B is an enlarged, partial cross-sectional view of the frame and a leaflet. As can be seen, the lower edge portion 102 of the leaflet extends perpendicularly or inversely parallel relative to the frame, creating a gap G between the inner surface of the frame and the bending axis 114 of the leaflet 20. Advantageously, this helps prevent or at least minimize contact of the outer surfaces of the leaflets with the frame and other relatively abrasive components, such as sutures, when the leaflets open during valve operation, thereby inhibiting undesirable abrasion of the leaflets that occurs through contact with the frame. The enlarged spaced between the leaflet and the frame also can promote blood washing over the leaflets at the bending axes of the leaflets.

Moreover, with known prosthetic valves, care must be taken to prevent the leaflets from extending through the open cells of the frame during crimping so as to prevent damage to the leaflets. For example, known crimping devices for prosthetic valves can include features or accessories that press the leaflets away from the frame or shield the leaflets from extending through the frame cells during crimping. In contrast, the skirts 100 assist in maintaining at least the inflow portions of the leaflets spaced from inner surface of the frame during crimping of the prosthetic valve to reduce the need for such specially designed crimping accessories.

Further, the connecting skirts 100 (and the other connecting skirts described herein) can facilitate assembly of the prosthetic valve compared to known assembly techniques. For example, the leaflets and the skirts can be assembled while the leaflets are in a flattened configuration, prior to forming the tubular (annular) configuration the valvular structure 14. Automated or semi-automated techniques can be used to suture the skirts to the leaflets. Also, once the valvular structure is placed inside of the frame, the lower edge portions 102 of the leaflets can be secured to the frame with stitching that is completely outside of the frame 12. This can substantially reduce assembly time as the assembler does not have to thread the needle for forming stitches 112 in and out of the cells 24 of the frame.

As further shown in FIGS. 13A-13B, each leaflet 20 comprises opposing tabs 60. Each tab 60 can be secured to an adjacent tab 60 of an adjacent leaflet 20 to form a commissure that is secured to the frame 12. Each tab 60 can be folded to form a radially extending layer 60a and a circumferentially extending layer 60b facing the frame. Methods for mounting commissures to the frame are described in detail below and can be incorporated into the prosthetic valve shown in FIGS. 13A-13B.

The tab layer 60a can have an inclined edge 62 that extends radially inwardly from a location on the frame to a coaptation edge 64 of the leaflet. The inclined edge 62 also extends in an axial direction from the location on the frame to the coaptation edge 64. This places the center of the coaptation edge 64 (halfway between adjacent commisures)

lower than the commissures and the attachment areas of the tabs 60 to the frame. In other words, the commissures are located at different locations along the height of the frame than the centers of the coaptation edges 64. This configuration is advantageous in that more evenly distributes stress along the tabs 60 during valve cycling. In some embodiments, the entire coaptation edge 64 of a leaflet is below the location where the commissures are attached to the frame, at least when the leaflets are in the closed positions.

During valve cycling, the leaflets can articulate at the inner most edges 66 of the tab layers 60a, which helps space the leaflets away from the frame during normal operation of the prosthetic valve. This is particular advantageous in cases where the prosthetic valve is not fully expanded to its nominal size when implanted in a patient. As such, the prosthetic valve can be implanted in a wider range of patient annulus sizes. Under relatively higher forces, such as when the prosthetic valve is radially compressed for delivery, the leaflets can splay apart from each other at the frame to relieve stress on the leaflets.

The commissures and the coaptation edges of the leaflets typically are relatively bulky portions of leaflets and can inhibit full radial compression of the prosthetic valve if they are at the same height along frame. Another advantage of the commissure tabs 60 shown in FIGS. 13A-13B is that the commissures and the coaptation edges are separated from each other in the axial direction when prosthetic valve is radially compressed for delivery into a patient's body. Separating these portions of the leaflets reduces the overall crimp profile of the prosthetic valve.

Figure 14:
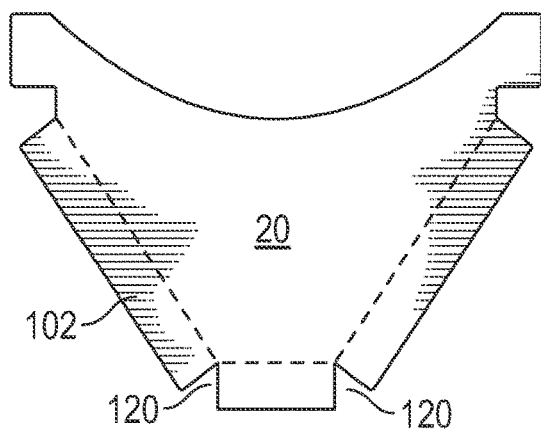
FIG. 14 is a plan view of a leaflet that can be used in a prosthetic heart valve, according to one embodiment.

FIGS. 14 and 15A-15D show an alternative technique for mounting the lower edge portion 102 of a leaflet to the frame 12 using a connecting skirt 100. As shown in FIG. 14, slits 120 can be formed along the lowermost section of the edge portion 102 to facilitate folding of the edge portion during the assembly process. FIGS. 15A-15D show a step-by-step process for attaching the skirt 100 to the leaflet 20 and then mounting the skirt to the frame.

Figure 15A:
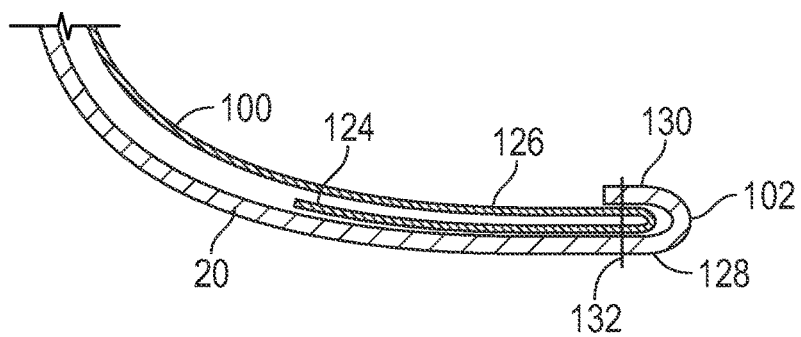
FIGS. 15A, 15B, 15C, 15D, 16, 17, 18, 19, 20, 21, 22, and 23 show various ways of connecting the cusp edge portion of a leaflet to a frame of a prosthetic heart valve using a connecting skirt.

Referring first to FIG. 15A, the skirt 100 is folded to form a first layer 124 and a second layer 126 and the folded skirt is placed along the upper surface of the leaflet 20. The edge portion 102 of the leaflet is then wrapped around the folded edge of the skirt 100 to form a first leaflet layer 128 and a second leaflet layer 130 sandwiching the layers 124, 126 of the skirt. The layers 124, 126, 128, 130 can then be secured to each other with stitches 132 that extend through all four layers and longitudinally along the length of the edge portion 102 of the leaflet. An advantage of folding the edge portion 102 of the leaflet is that the leaflet can better resist pull through of the stitches 132.

Figure 15B:
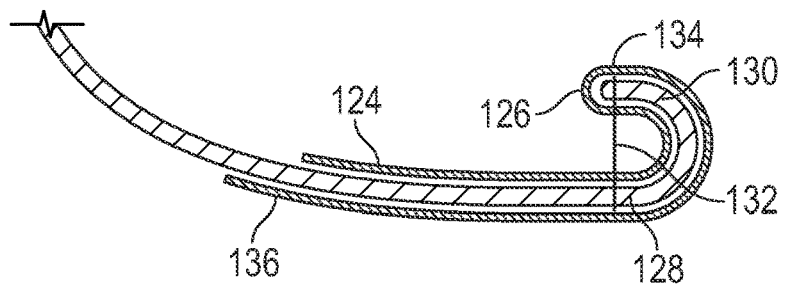
Figure 15C:
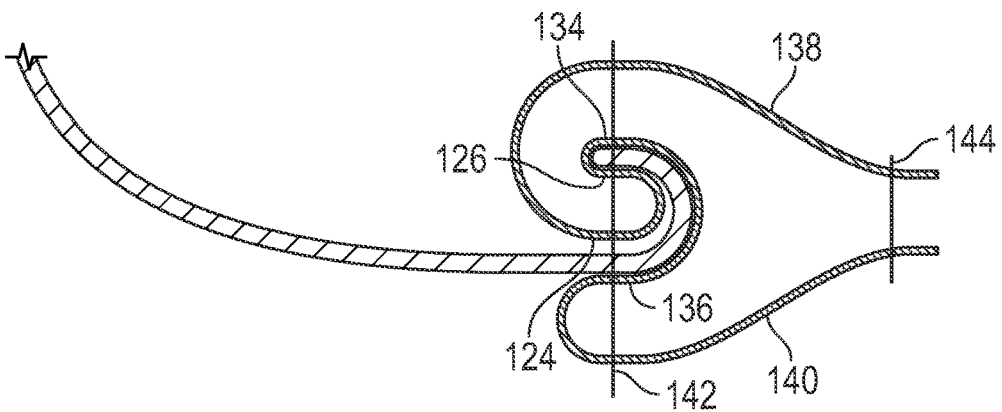

Referring to FIG. 15B, the second layer 126 of the skirt can then be folded around the two leaflet layers 128, 130 to form a third skirt layer 134 adjacent the second leaflet layer 130 and a fourth skirt layer 136 adjacent the first leaflet layer 128. Referring to FIG. 15C, the first skirt layer 124 can then be folded back over the third skirt layer 134 to form a fifth skirt layer 138. The fourth skirt layer 136 can folded back over itself to form a sixth skirt layer 140. All six skirt layers and the two leaflet layers can be secured together with stitches 142 extending through all eight layers and longitudinally along the length of the edge portion 102 of the leaflet. In addition, the fifth and sixth layers 138, 140, respectively, can be secured together at a location spaced radially outward from the leaflet 20 with stitches 144 that extend through both layers and longitudinally along the length of the skirt 100.

Figure 15D:
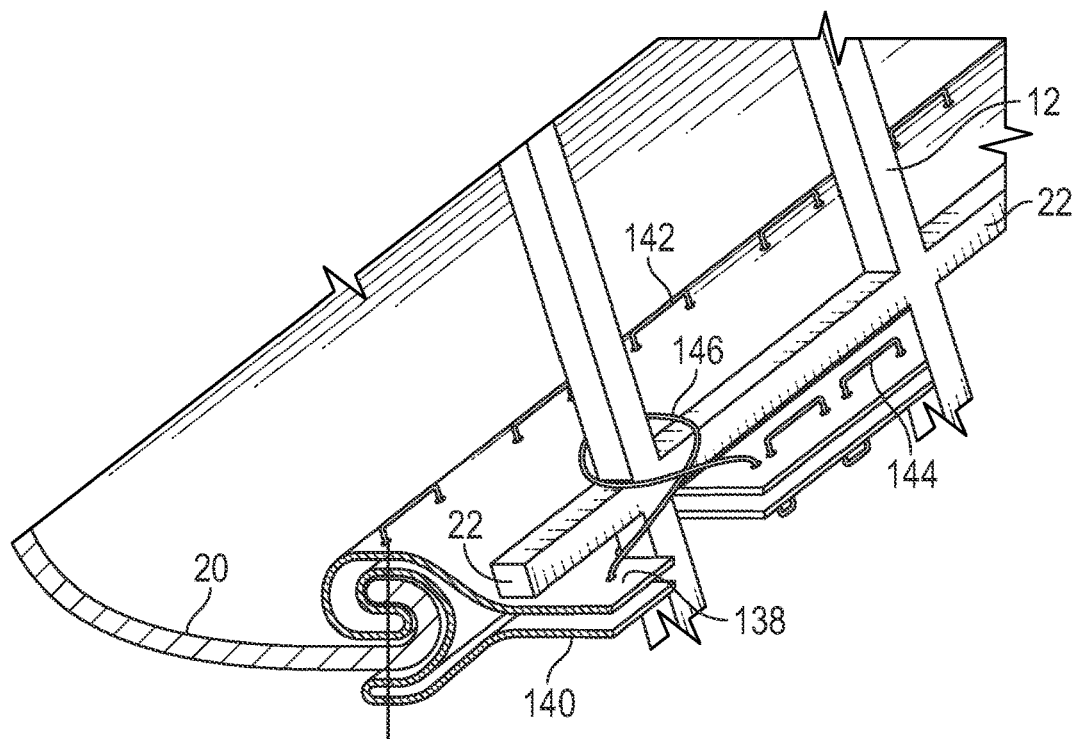

The leaflet and skirt assembly can then be secured to the frame 12. As shown in FIG. 15D, for example, layers 138, 140 of the skirt can be placed below struts 22 of the frame and secured to the frame using, for example, stitches 146 that extend around the struts and through the layers 138, 140. Alternatively, the stiches 144 also can be wrapped around the struts of the frame to mount the leaflet and skirt assembly, in lieu of or in addition to stitches 146. Thus, the lower edge portion of each leaflet extends along a diagonal line just below the line 116 (FIG. 8) defined by the diagonal row of struts. Mounting the skirt below the diagonal row of struts 22 reduces motion of the skirt relative to the frame and resulting abrasion of the skirt so as to protect against tearing of the skirt during operation of the prosthetic valve.

In alternative embodiments, the skirt can be secured to the frame by placing the fifth layer 138 over the struts and the sixth layer 140 below the struts and securing those layers directly to each other outside of the frame (e.g., with sutures), similar to the way the skirt is secured to the frame in FIG. 12.

Figure 16:
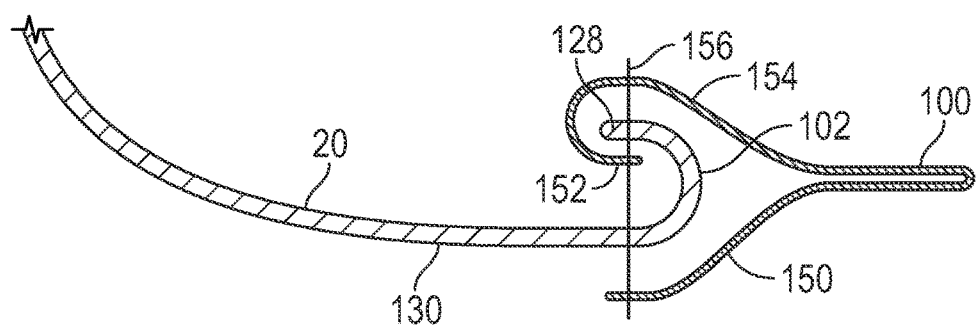
Figure 17:
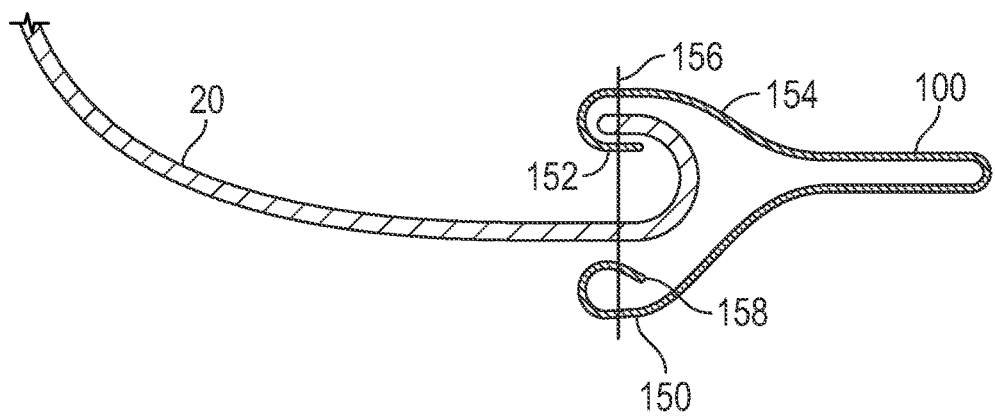
Figure 18:
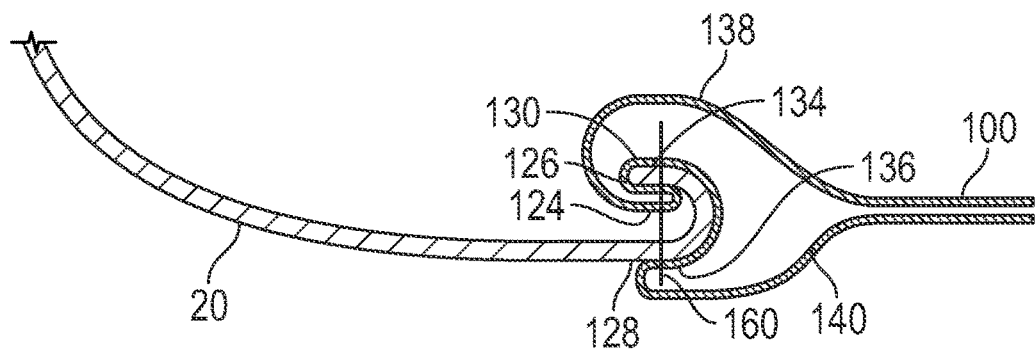

FIGS. 16-18 show alternative configurations for assembling a skirt 100 and a leaflet 20 utilizing a folded leaflet edge portion. In FIG. 16, the skirt 100 is folded around the leaflet layers 128, 130 to form a first skirt layer 150 below the leaflet layer 130, a second skirt layer 152 between the leaflet layers 128, 130, and a third skirt layer 154 above the leaflet layer 128. The leaflet and the skirt can be secured to each other using stitches 156 that extend through the skirt layers 150, 152, 154 and the leaflet layers 128, 130 and longitudinally along the length of the leaflet edge portion 102. The configuration of FIG. 16 utilizes less skirt layers than FIGS. 15A-15D and can permit a lower overall crimp profile for the prosthetic valve 10. FIG. 17 is similar to FIG. 16 except that the first skirt layer 150 is folded inwardly to form an additional fourth skirt layer 158 between the first skirt layer 150 and the lower surface of the leaflet 20. The fourth skirt layer 158 can help inhibit abrasion of the leaflet by positioning the edge of the skirt away from the articulating portion of the leaflet. FIG. 18 utilizes the same configuration as the embodiment of FIGS. 15A-15D except that in the embodiment of FIG. 18, stitches 160 extend through skirt layers 124, 126, 134, 136 and leaflet layers 128, 130 but not skirt layers 138, 140. The leaflet and skirt assemblies shown in FIGS. 16-18 can be secured to a frame 12 as previously described.

Figure 19:
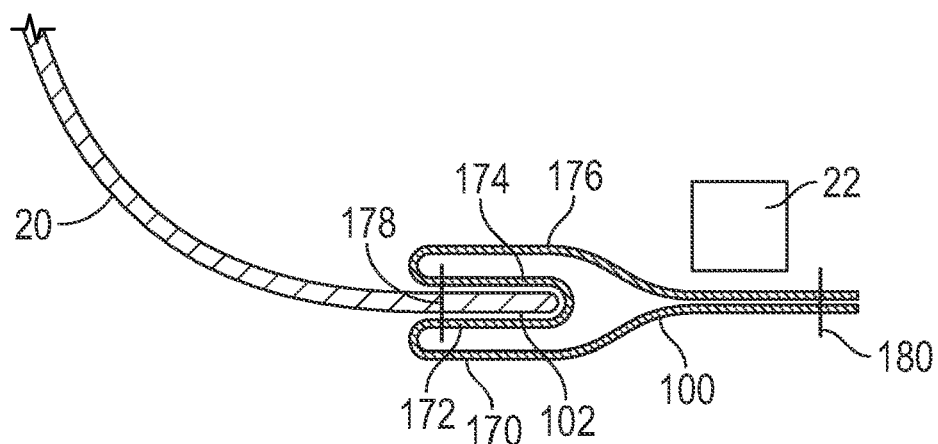
Figure 20:
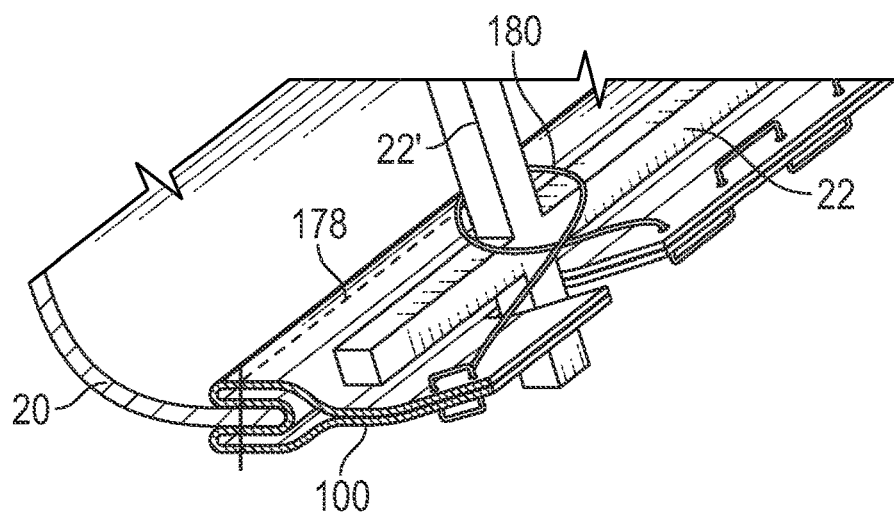
Figure 21:
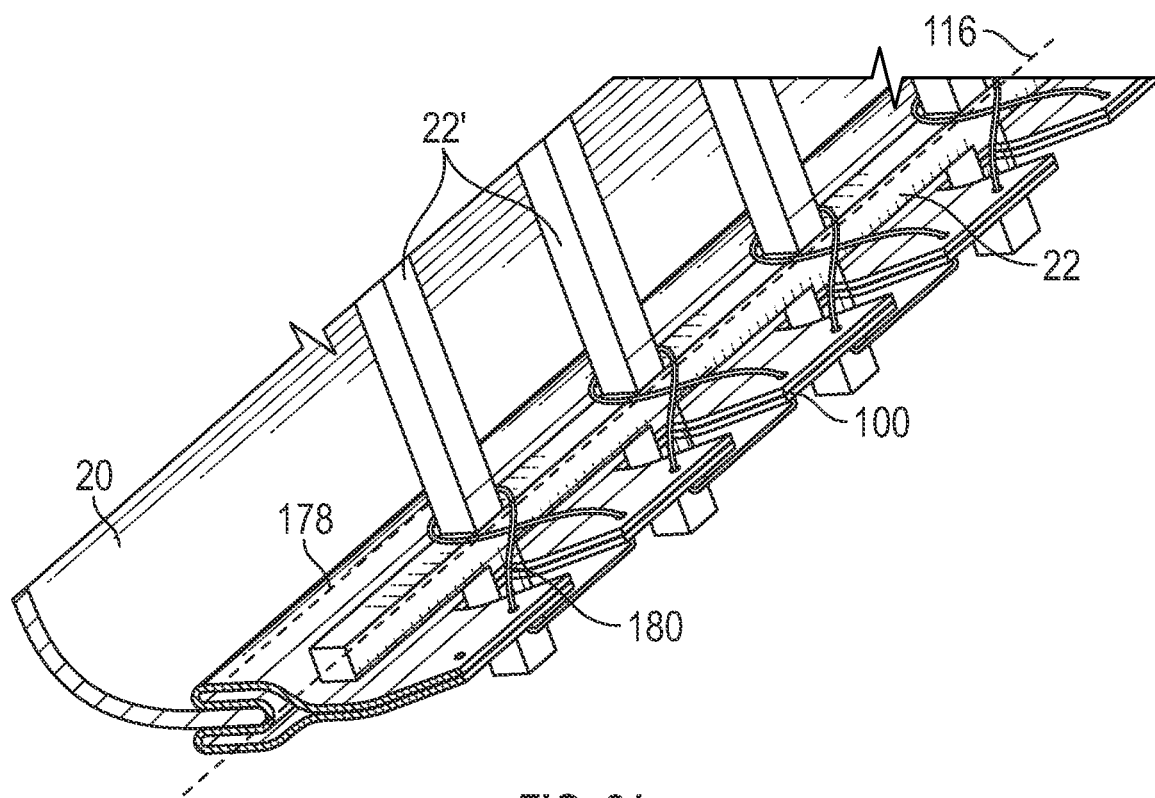

FIGS. 19-21 show another configuration for assembling a leaflet 20 and a skirt 100. As shown in FIG. 19, the skirt 100 is folded around a lower edge portion 102 of the leaflet 20 to form first and second skirt layers 170, 172 on the lower surface of the leaflet and third and fourth skirt layers 174, 176 on the upper surface of the leaflet. The inner edges of the folded layers can be secured with stitches 178 extending through all four layers 170, 172, 174, 176 and longitudinally along the length of the skirt and the leaflet. As shown in FIGS. 20 and 21, the skirt 100 can then be mounted to the frame 12 by positioning the outer edges of skirt layers 170, 176 below the diagonal row of struts 22 and securing those layers to each other and the struts with stitches 180. The stitches 180 extend through layers 170, 176 and around struts 22' that intersect with the struts 22 that form the diagonal row 116 of struts 22 above the row.

Figure 22:
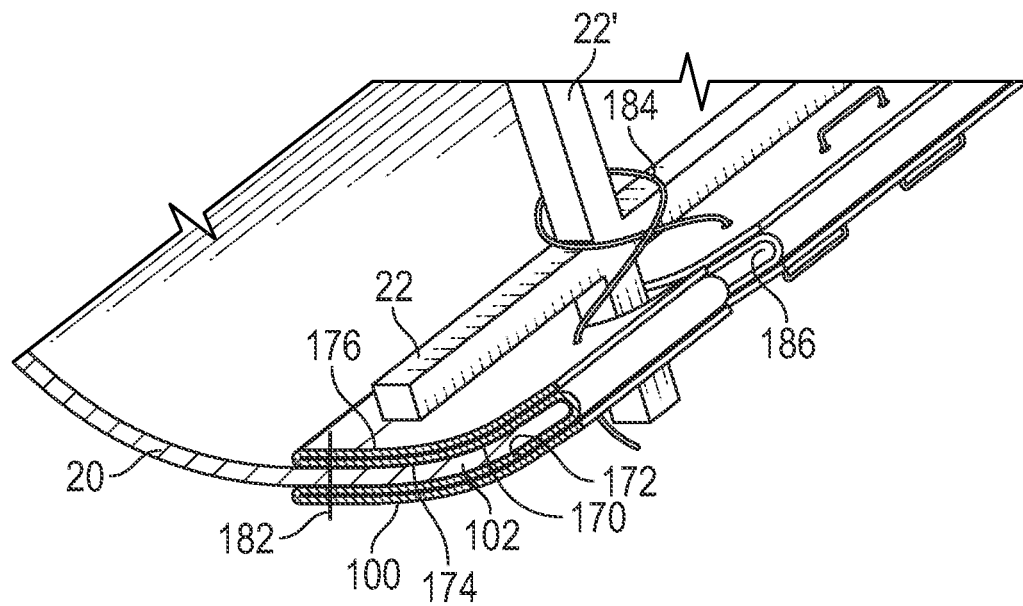

FIG. 22 shows a similar configuration to that shown in FIGS. 19-21 except that sections of the lower edge portion 102 of the leaflet extend through the cells of the frame. A first row of stitches 182 can be used to secure the lower edge portion 102 of the leaflet and the inner edges of the folded layers 170, 172, 174, 176. A second row of stitches 184 can be used to secure the lower edge portion 102 of the leaflet and the outer edges of the folded layers 170, 172, 174, 176 at a location outside of the frame. The lower edge portion 102 of the leaflet can be formed with a series of slits 186 spaced along the length of the leaflet corresponding to location of struts 22 to allow the sections of the lower edge portion 102 to be extended through the cells of the frame.

Figure 23:
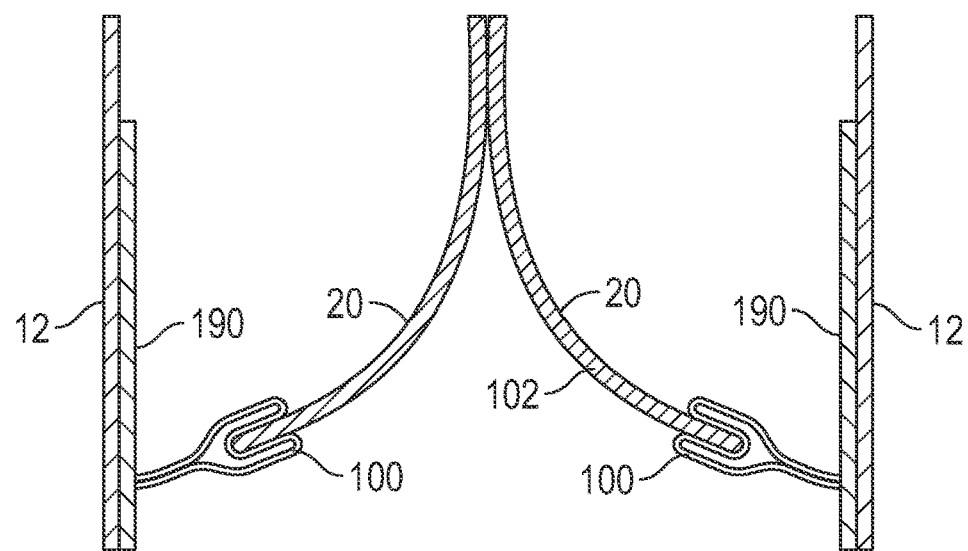

FIG. 23 is a schematic representation of mounting the leaflets 20 to the frame utilizing connecting skirts 100. In the illustrated embodiment, the outer edges of the connecting skirts 100 can be secured to an annular inner skirt 190 (e.g., with sutures, an adhesive, or welding), which in turn can be secured to the struts of the frame (e.g., with sutures, an adhesive, or welding). Alternatively, the outer edges of the connecting skirts 100 can be mounted directly to the struts of the frame without an inner skirt 190, as previously described with respect to the embodiments in FIGS. 8-22. The inner edges of the connecting skirts 100 can be connected to respective lower edge portions 102 of the leaflets (e.g., by sutures), which can be spaced from the inner surface of the inner skirt 190 and/or the frame 12 by the connecting skirts. In particular embodiments, for example, the width of a skirt 100 between the lower edge of the respective leaflet 20 and the inner surface of the inner skirt 190 and/or the frame 12 can be about 1 mm to about 5 mm.

Forming the connecting skirts 100 from a fabric (e.g., PET) can promote tissue ingrowth and the formation or deposition of biological components, such as fibrin and other blood components along the upper surface of the connecting skirts during valve operation. Due to the material deposition of the skirts 100, they effectively become thicker and stiffer, thereby resisting flexing of the skirts during valve cycling. As a result, the normally closed position of the leaflets is dictated by diastolic pressure on the leaflets. During the systolic phase, the skirts 100 can remain substantially stationary, creating a gap between the leaflets and the inner surface of the inner skirt 190 and/or the frame 12 to protect against abrasion of the leaflets through contact with those components of the prosthetic valve.

Figure 24:
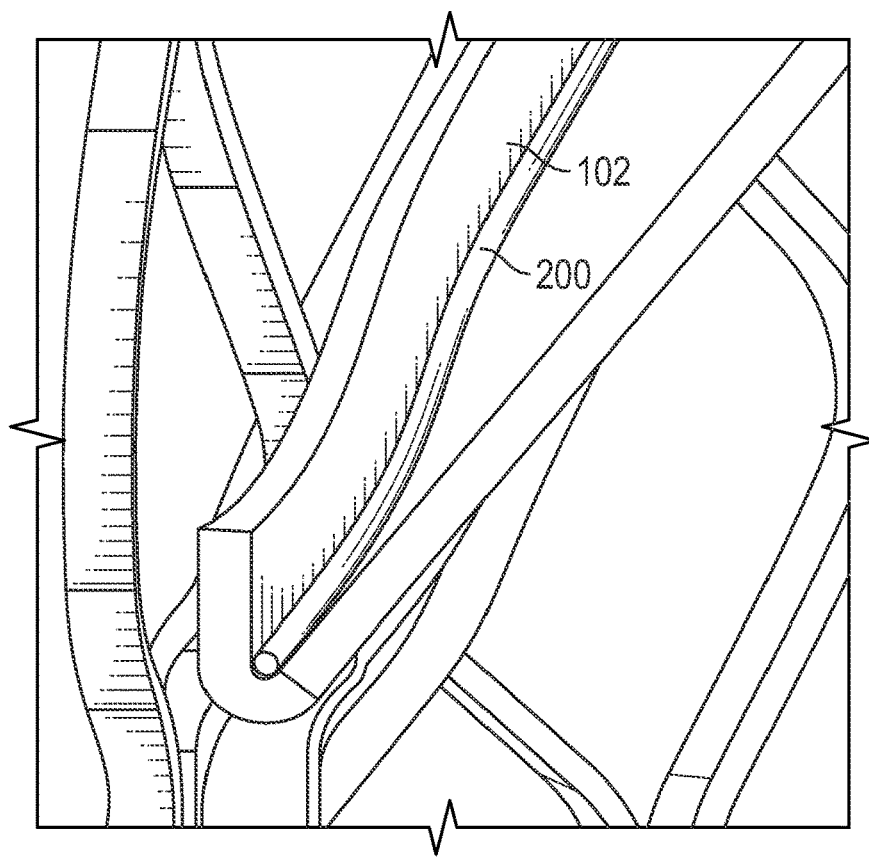
FIG. 24 is an enlarged, perspective view of the inside of a prosthetic heart valve, showing another way of connecting the cusp edge portion of a leaflet to the frame of the valve.

FIGS. 24-25 show another configuration for mounting the lower, scalloped-shaped edge portions 102 of the leaflets to the frame 12. As shown in FIG. 24, the lower edge portion 102 of a leaflet 20 can be folded upwardly toward the outflow end of the frame and against the inner surface of the frame to create a bending axis between the lower edge portion and the remaining portion of the leaflet that can articulate toward and away from the frame during valve cycling. The bending axis of the leaflets is therefore spaced inwardly from the frame, which can provide several advantages, including protection against leaflet abrasion during valve cycling, reduction of stress along the lower edge of the leaflets during valve closure, improved blood-washing of the leaflets (thus eliminating or at least minimizing early calcification in those areas), and improved closing action of the leaflets. A reinforcing member 200, such as a wire, chord, sleeve, fabric or suture, can be placed along the upper surface of the leaflet at the bending axis where the lower edge portion 102 intersects with the articulating portion of the leaflet. In other embodiments, the reinforcing member 200 can be placed along the lower surface of the leaflet. The reinforcing suture 200 can comprise, for example, a multifilament suture (e.g., an Ethibond suture).

Figure 25A:
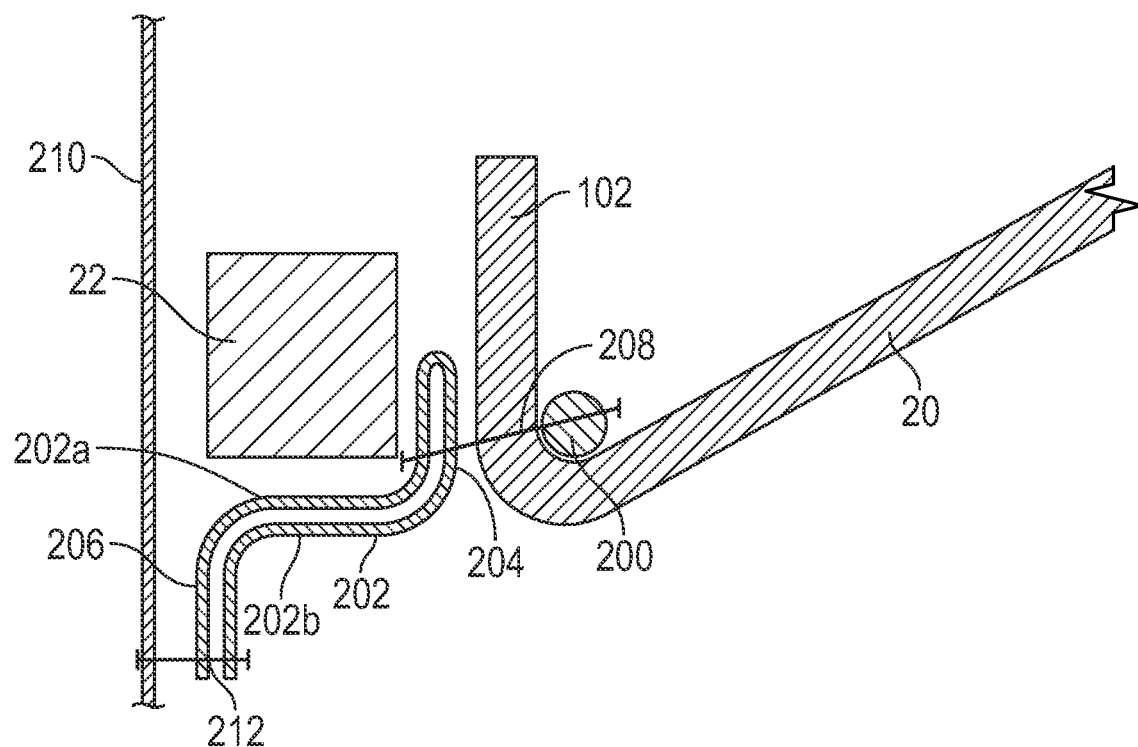
Figure 25B:
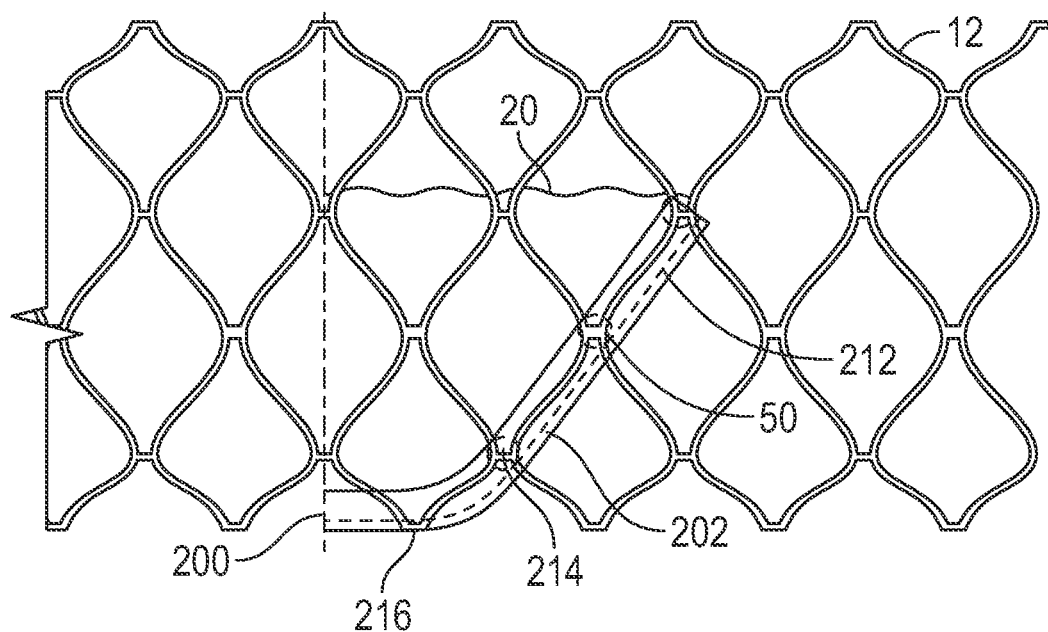

The leaflet 20 can be coupled to the frame 12 using various techniques or mechanisms. As shown in FIGS. 25A-25B, for example, the leaflet 20 can be coupled to the frame 12 with a connecting skirt 202 having an inner longitudinal edge portion 204 and an outer longitudinal edge portion 206. The inner edge portion 204 can be folded upwardly against the lower edge portion 102 of the leaflet. The outer edge portion 206 can be folded downwardly against an outer skirt 210 (which can comprise, for example, the sealing member 16) mounted on the outside of the frame. The outer edge portion 206 can contact the outer skirt 210 through the cells of the frame at a location below a diagonal row of struts 22. The connecting skirt 202 can comprise two layers 202a, 202b of material formed, for example, by folding the skirt lengthwise prior to assembling the skirt to the leaflet. Alternatively, the connecting skirt 202 can comprise a single layer of material.

The inner edge portion 204 can be secured to the leaflet 20 with stitches 208 extending through the skirt 202, the leaflet 20, and the reinforcing suture 200 and longitudinally along the leaflet and the skirt. The outer edge portion 206 can be secured to the outer skirt 210 via stitches 212 that extend through the connecting skirt 202 and the outer skirt 210 and longitudinally along the connecting skirt. As shown in FIG. 25B, the connecting skirt 202 also can be secured directly to the frame via the stitches 212 or separate stitches that extend through the outer edge portion 206 of the skirt 202 and around junctions 50 of the frame where two struts intersect. The connecting skirt can be left unattached to apices 216 formed by the intersection of respective pairs of struts 22 at the inflow end of the frame.

The row of stitches 212 desirably extends above the apices 216 as shown to prevent the leaflets from protruding below the inflow end of the frame so as to protect against the leaflets contacting adjacent native tissue, such as calcium nodes, prior to or during deployment of the prosthetic valve 10. Having the lower edge portions 102 of the leaflets folded upwardly away from the connecting skirt 202 and toward the outflow end of the frame can minimize the amount of overlapping layers of material of the skirt 202, the leaflet 20 and the frame 12 so as to reduce the overall crimp profile of the prosthetic valve.

Figure 26:
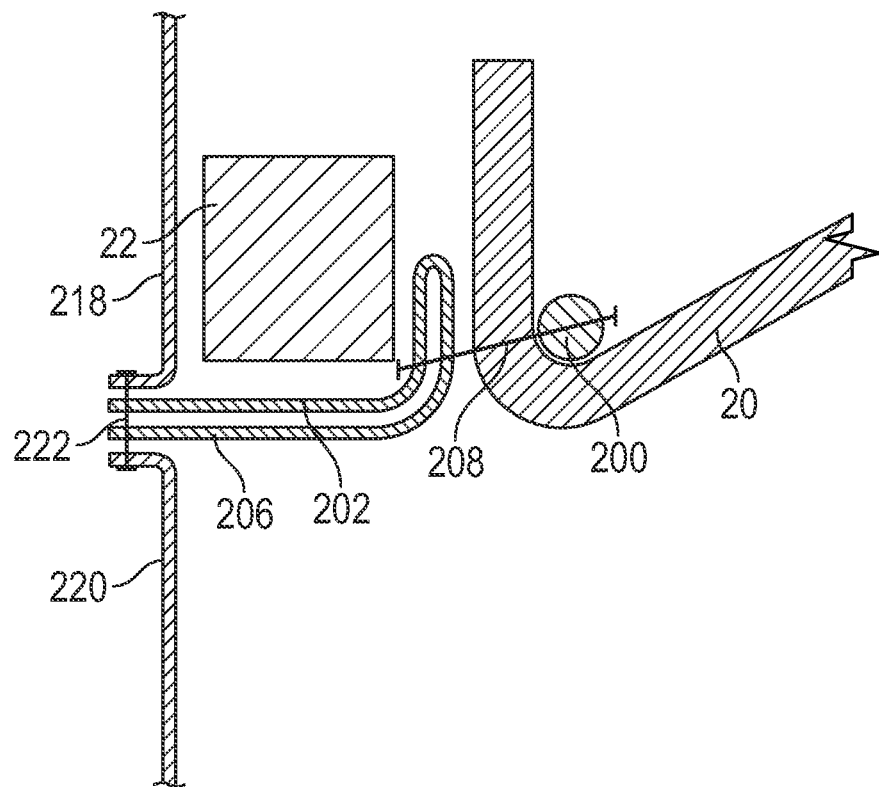

FIG. 26 shows an alternative configuration for mounting the leaflets 20 to the frame using the connecting skirts 202. The embodiment of FIG. 26 can be the same as the embodiment of FIGS. 24 and 25 except that the outer edge portion 206 of the connecting skirt 202 extends between a lower edge portion of an upper outer skirt 218 and an upper edge portion of a lower outer skirt 220. The connecting skirt 202, the upper outer skirt 218, and the lower outer skirt 220 can be secured to each other with stitches 222 extending through all three layers of material.

Figure 27:
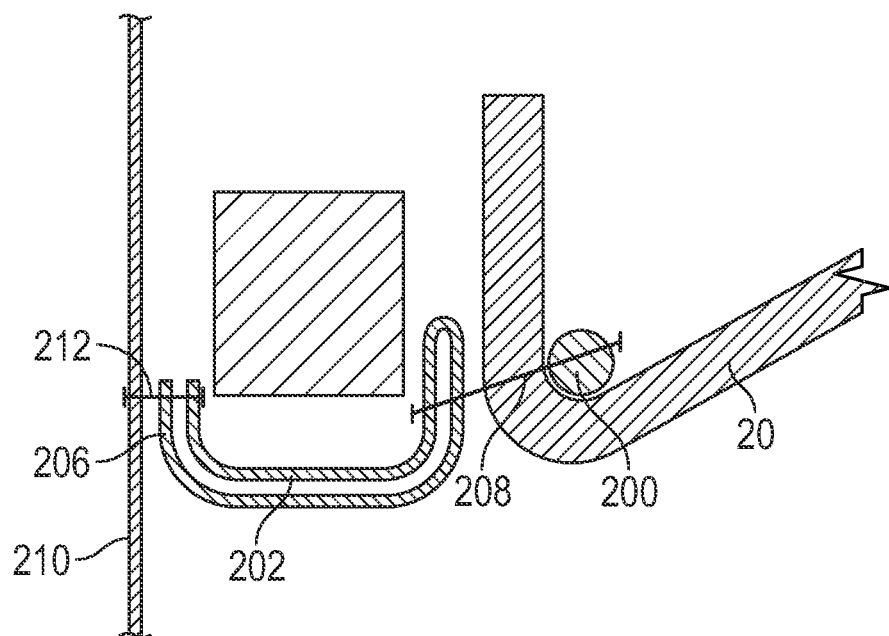

FIG. 27 shows another alternative configuration for mounting the leaflets 20 to the frame using the connecting skirts 202. The embodiment of FIG. 27 can be the same as the embodiment of FIGS. 24 and 25 except that the outer edge portion 206 of the connecting skirt 202 can be folded upwardly toward the outflow end of the frame. The outer edge portion 206 can be secured to the outer skirt 210 with stitches 212.

FIGS. 28 and 29 illustrate in greater detail different ways of stitching the inner edge portion 204 of the connecting skirt 202 to the lower edge portion 102 of a leaflet 20. In FIG. 28, the stitches 208 extend through the inner skirt layer 202b but not the outer skirt layer 202a. In FIG. 29, the stitches 208 extend through both skirt layers 202a, 202b.

FIG. 30 shows another configuration for mounting the lower edge portions 102 of the leaflets to the frame 12. As shown in FIG. 30, the lower edge portion 102 of a leaflet can be coupled to the frame 12 with a connecting skirt 230 having an upper edge portion 232 and a lower edge portion 234. The upper edge portion 232 can be secured to an outer skirt 210 at a location above a diagonal row of struts 22 via stitches 236 that extend through the outer skirt and the connecting skirt. The lower edge portion 234 of the connecting skirt can be secured to the outer skirt at a location below the diagonal row of struts 22 via stitches 238 that extend through the outer skirt and the connecting skirt. An intermediate portion of the connecting skirt (between the upper and lower edge portions 232, 234) can extend over the diagonal row of struts.

As shown in FIG. 30, the spacing between the row of struts and the stitching 236 desirably is greater than the spacing between the row of struts and the stitching 238, which can increase the contact angle of the skirt and the struts 22. The encircled area 240 in FIG. 30 represents the contact area where contact between the connecting skirt 230 and the frame 12 occurs, or where a majority of the contact between the connecting skirt and the frame occurs. Under systole, the angle of the skirt 230 relative to a transverse axis of the frame (the transverse axis being perpendicular to a longitudinal axis of the frame) at the contact area 240 is about 60 to 90 degrees, or more preferably about 70 to 90 degrees, or even more preferably about 80 to 90 degrees. Increasing the contact angle of the skirt can reduce bending stresses in the skirt during valve cycling to improve durability of the skirt. Further, the connecting skirt 230 can be sized or configured such that during diastole, the connecting skirt can move slightly radially inwardly under blood pressure and separate from the skirt 230 from the struts 22 so as to remove or minimize contact between the skirt and struts.

FIG. 31 shows another configuration for mounting the lower edge portions 102 of the leaflets to the frame 12 with connecting skirts 230 similar to the embodiment of FIG. 30 except that the upper edge portion 232 of the connecting skirt is secured to an upper diagonally extending row of struts 22a and the lower edge portion 234 of the connecting skirt is secured to a lower diagonally extending row of struts 22b. In this manner, the lower edge portion 102 of the leaflet can be secured to the connecting skirt 230 between the upper and lower rows of struts. The upper edge portion 232 of the connecting skirt can be at least partially wrapped around the struts 22a of the upper row and secured in place by loop stitches 250 extending through the skirt and around the struts 22a. The lower edge portion 234 of the connecting skirt can be at least partially wrapped around the struts 22b of the lower row and secured in place by loop stitches 252 extending through the skirt and around the struts 22b. Attaching the connecting skirt 230 to two adjacent diagonally extending rows of struts in the manner shown in FIG. 31 can prevent or at least minimize relative motion between the connecting skirt and the frame to improve durability of the skirt.

Figure 32:
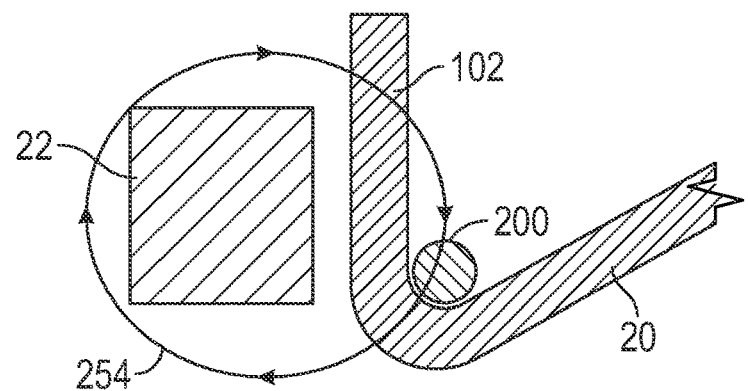

FIG. 32 shows another configuration for mounting the lower edge portions 102 of the leaflets to the frame 12 without any connecting skirts. In the embodiment of FIG. 32, the lower edge portion 102 of a leaflet 20 can be folded upwardly against a diagonal row of struts 22 and secured in place with loop stitches 254 extending around the struts 22 and through the leaflet edge portion 102 at a first location, through the reinforcing suture 200, and through the leaflet edge portion 102 at a second location. Placing the folded edge portion 102 of the leaflet parallel to the inner surfaces of the struts can minimize wear of the leaflets due to motion of the leaflets relative to the frame. The elimination of the skirts in this embodiment can reduce the overall crimp profile of the prosthetic valve and can achieve a tighter connection between the leaflets and the frame to reduce relative motion between these two components.

FIGS. 33-37 show a technique for mounting the commissures of a valvular structure to a frame, such as the commissures 32 to the frame 12, according to one embodiment.

Figure 33:
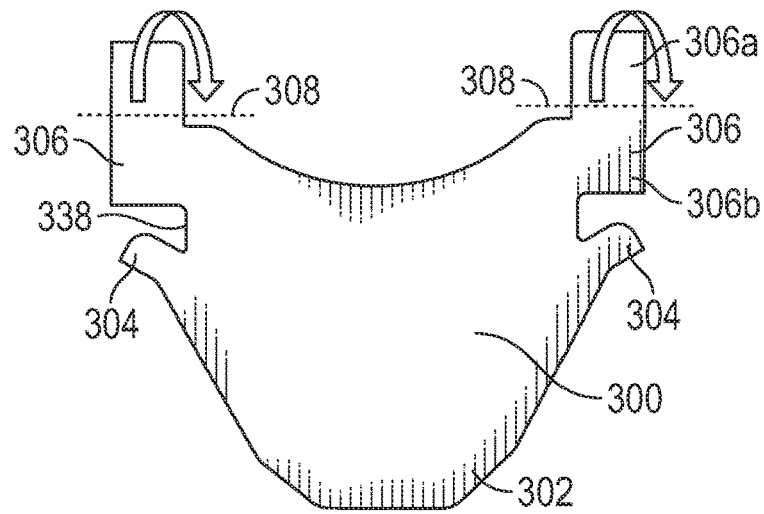
FIG. 33 is a plan view of a leaflet that can be used in a prosthetic heart valve, according to one embodiment.
Figure 34:
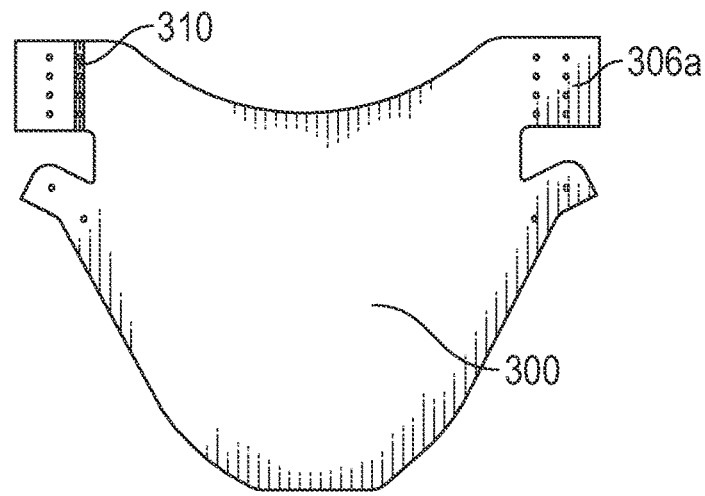
FIGS. 34, 35, and 36 show the formation of one-half of a commissure using the leaflet of FIG. 33, according to one embodiment.

FIG. 33 shows a leaflet 300 having a lower edge portion 302 that can be mounted to the frame 12 using any of the previously described embodiments. The lower edge portion 302 terminates at its upper ends at two laterally projecting integral lower tabs 304. Projecting from the upper corners of the leaflet 300 are integral upper tabs 306 (also referred to as commissure tabs). The upper tabs 306 can be spaced from the lower tabs 304 by side edges 338 defining laterally extending gaps or recesses in the leaflet.

Figure 37:
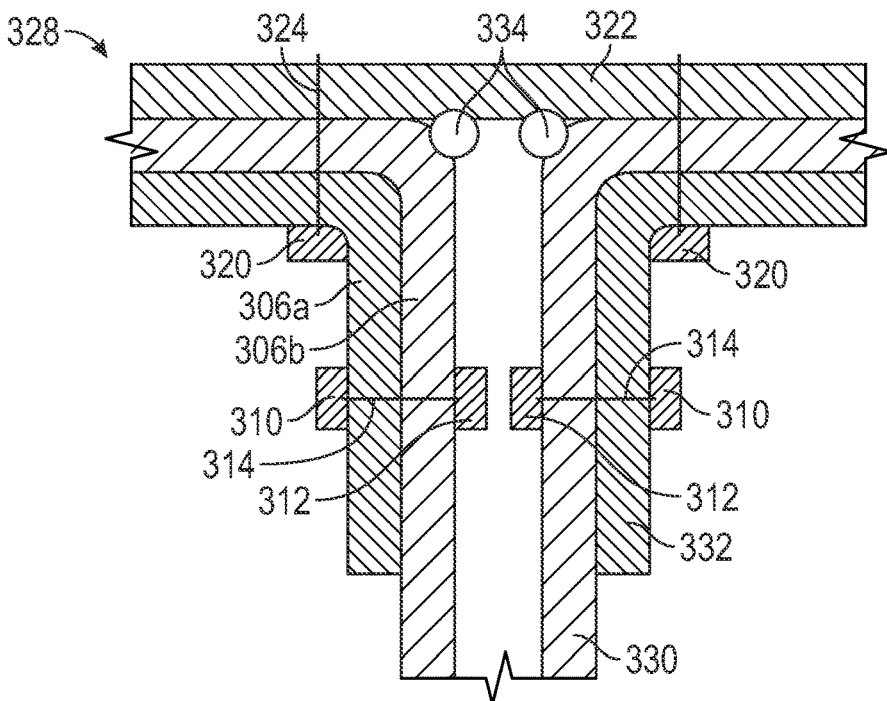
FIG. 37 is a cross-sectional view of a commissure formed from two leaflets of the type shown in FIG. 33, according to one embodiment.

To assemble the commissure, each upper tab 306 is folded along a horizontal fold line 308 to form first and second tab layers 306a, 306b, as shown in FIG. 33 (see also FIG. 37). A first vertically extending reinforcing member 310 can be placed against the first tab layer 306a adjacent its inner edge. A second vertically extending reinforcing member 312 can be placed against the second tab layer 306b opposite the first reinforcing member 310. The first and second tab layers 306a, 306b can be secured to each other with stitching 314 that extends through the first and second tab layers 306a, 306b and the first and second reinforcing members 310, 312.

Figure 35:
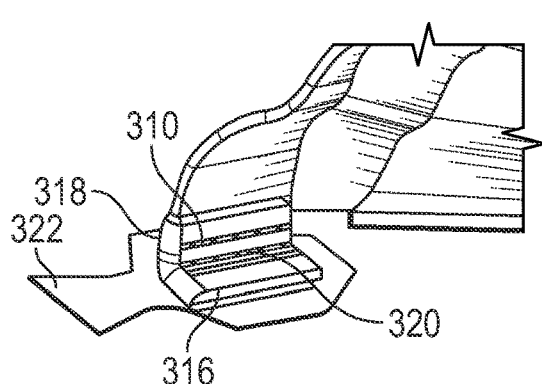
Figure 36:
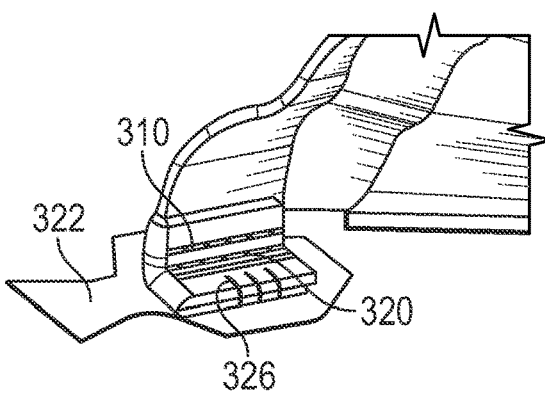

The first and second tab layers 306a, 306b can then be folded lengthwise along a vertical fold line as shown in FIG. 35 to form an outer folded portion 316 and an inner folded portion 318 that extends radially inwardly from the outer folded portion 316. A third vertically extending reinforcing member 320 can be placed against the first folded layer 306a of the outer folded portion 316 and a commissure attachment member 322 can be placed against the second folded layer 306b of the outer folded portion 316. The outer folded portion 316 can be secured to the commissure attachment member 322 with stitches 324 that extend through the third reinforcing member 320, the first and second tab layers 306a, 306b, and the commissure attachment member 322. The outer edges of the first and second tab layers 306a, 306b can be further secured to the commissure attachment member 322 with stitches 326. The upper tab 306 of a second leaflet 300 can be assembled in the same manner with respective reinforcing members and attached to the commissure attachment member 322 adjacent the first leaflet to form a commissure 328 as shown in FIG. 37. The commissure attachment member 322 can then be secured to the struts of the frame (see, e.g., FIG. 65), as further described below.

The folded tab layers 306a, 306b, reinforced by the first and second reinforcing members 310, 312, can be more resistant to bending, or articulating, than the portions 330 of the leaflets that are radially inward of the tab layers. This causes the leaflets 300 to articulate primarily at inner edges 332 of the folded layers 306a in response to blood flowing through the prosthetic valve during operation of the prosthetic valve in the body, as opposed to articulating about respective axes on or adjacent the metal struts of the frame. Because the leaflets articulate at a location spaced radially inwardly from the frame 12, the leaflets can avoid contact with and damage from the frame. This is particularly advantageous in cases where the prosthetic valve is not fully expanded to its nominal size when implanted in a patient's body. As such, the prosthetic valve can be implanted in a wider range of patient annulus sizes.

Under high forces, the folded tab layers 306a, 306b of adjacent leaflets can splay apart from each other about respective axes 334 (FIG. 37) adjacent to the frame 12, with each inner folded portion 318 folding out against the respective outer folded portion 316. For example, this can occur when the prosthetic valve 10 is compressed and mounted onto a shaft of a delivery apparatus, allowing for a smaller crimped diameter. The folded tab layers can also splay apart about their axes 334 when the balloon of the balloon catheter is inflated during expansion of the prosthetic valve, which can relieve some of the pressure on the commissures caused by the balloon and so the commissures are not damaged during expansion.

When the leaflets 300 are mounted to the frame, the lower tabs 304 of each leaflet can be folded downwardly against the cusp edge portion 302 and held in place, such as with sutures. The folded lower tabs 304 help reinforce the connection between the cusp edge portions 302 of the leaflets and the frame along the upper sections of the cusp edge portions adjacent the commissures. The folded lower tabs 304 also move the bending axes of the upper sections of the cusp edge portions inwardly and away from the inner surface of the frame to prevent or minimize contact between the leaflets and the frame in the areas below the commissures.

Figure 1C:
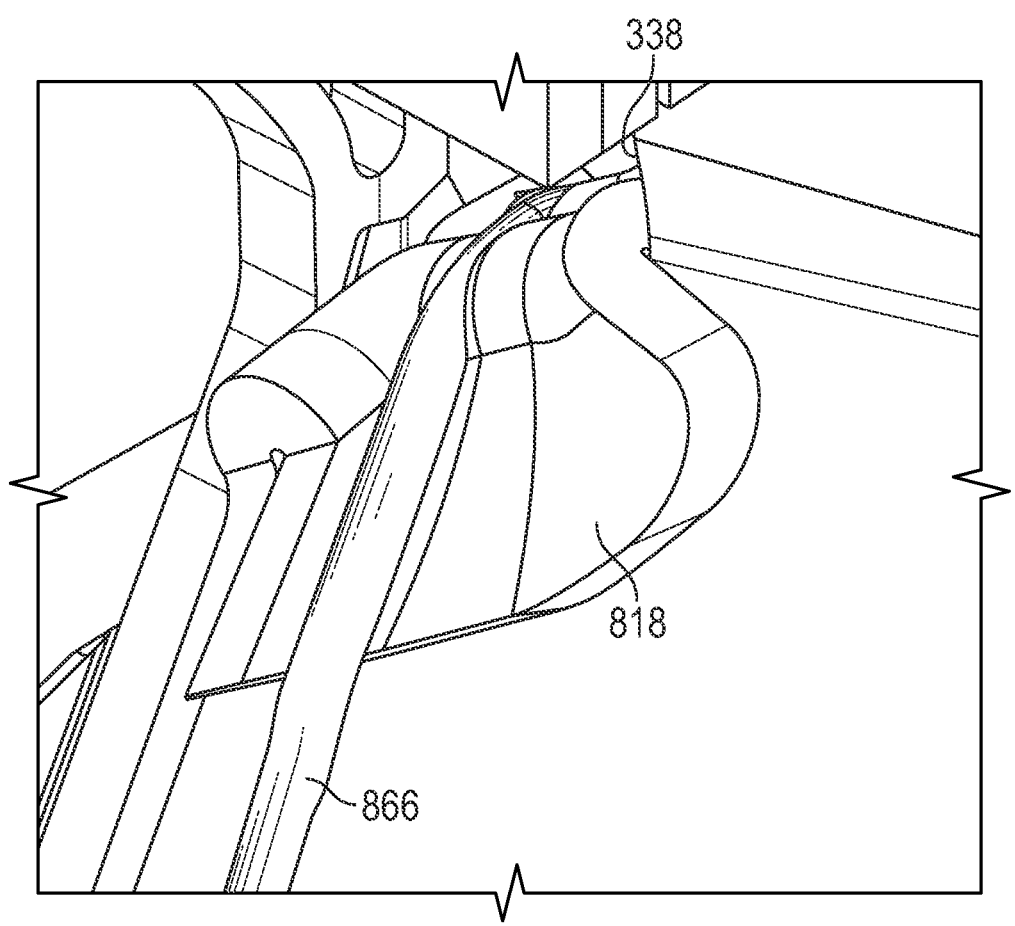
FIG. 1C is an enlarged, perspective view of the area beneath one of the commissures of the prosthetic heart valve of FIGS. 1A-1B.
Figure 2:
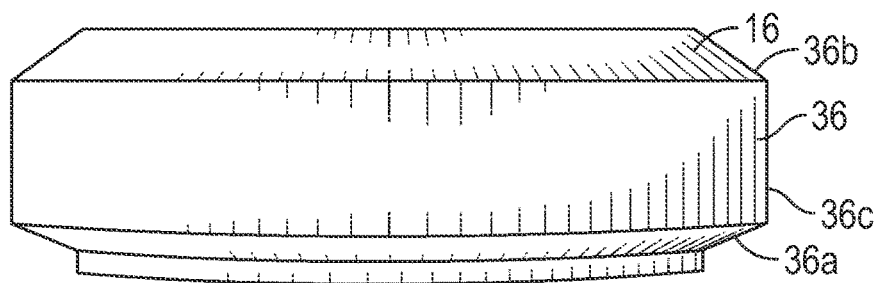
FIG. 2 is a side elevation of the sealing member of the prosthetic heart valve of FIG. 1.

The side edges 338 between the lower and upper tabs 304, 306 can be left unattached to the frame of the prosthetic valve (see FIG. 1C). The unattached side edges 338 provide several advantages, including reducing stress in the leaflets, by allowing greater elongation or stretching of the leaflets in the axial direction when the prosthetic valve is compressed from the radial expanded state to the radial compressed state during the crimping process and by allowing greater elongation or stretching of the leaflets in the radial direction when the prosthetic valve is expanded to its radial expanded state. The unattached side edges 338 also allow blood to flow in the space between a pair of side edges 338 of adjacent leaflets and the inner surface of the frame to reduce stagnant blood flow and thrombosis. During diastole, the adjacent side edges 338 can coapt with each other and prevent retrograde blood from flowing between the side edges 338. During systole, the adjacent side edges 338 can separate from each other and allow antegrade blood to flow between side edges 338 and help wash away blood from the areas underneath the commissures.

The reinforcing members 310, 312, 320 desirably comprise relatively soft and flexible, non-metallic materials. For example, the reinforcing members can comprise multi-filament sutures (e.g., Ethibond sutures) or strips of synthetic material, such as fabric (e.g., PET) or non-fabric material (e.g., silicone or polyurethane), or natural tissue (e.g., pericardium). The commissure attachment member 322 similarly can comprise a soft and flexible, non-metallic material, such as strips of synthetic material, such as fabric (e.g., PET) or non-fabric material (e.g., silicone or polyurethane), or natural tissue (e.g., pericardium). Hence, in the illustrated embodiment, the commissure 328 does not include metallic components or other materials having similar rigidity. The absence of such materials can reduce abrasion and wear of the leaflet material and reduce the overall crimp profile of the prosthetic valve.

Figure 38:
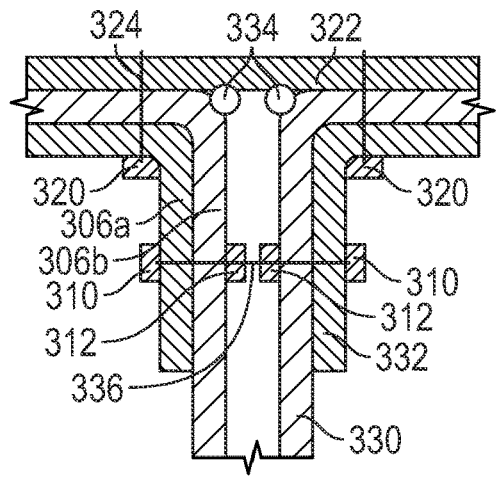
FIG. 38 is a cross-sectional view of a commissure formed from two leaflets of the type shown in FIG. 33, according to another embodiment.

FIG. 38 shows a modification of the embodiment shown in FIG. 37. The embodiment of FIG. 38 can be same as that shown in FIG. 37 except that the pair of folded layers 306a, 306b of adjacent leaflets 300 can be secured to each other with a suture 336 that extends through the reinforcing members 310, 312 and the tab layers 306a, 306b of each leaflet 300. Securing the leaflets together can reinforce the bending axes of the articulating portions 330 of the leaflets during normal valve operation.

Figure 39:
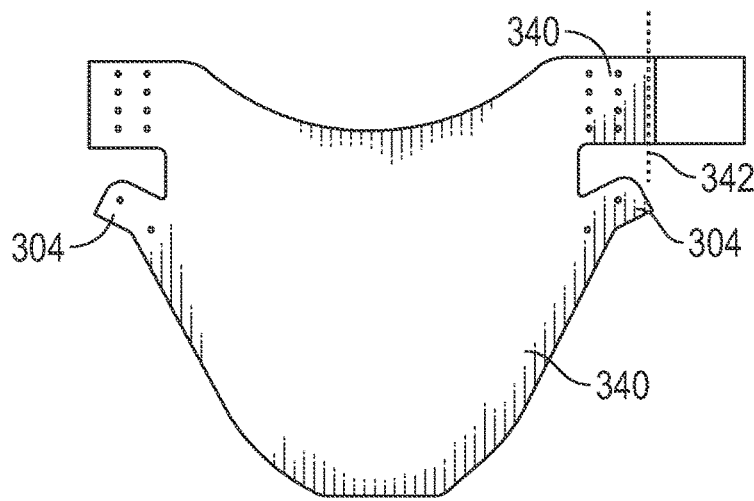
FIG. 39 is a plan view of a leaflet that can be used in a prosthetic heart valve, according to another embodiment.

FIG. 39 shows an alternative embodiment of a leaflet 340, which is similar to the leaflet 300, except that the leaflet 340 includes upper tabs 340 that project laterally a greater distance than the upper tabs 306. Each upper tab 340 can be folded widthwise along a respective vertical fold line 342 to form two folded tab layers that are paired with folded tab layers of an adjacent leaflet to form a commissure as previously described.

Figure 40:
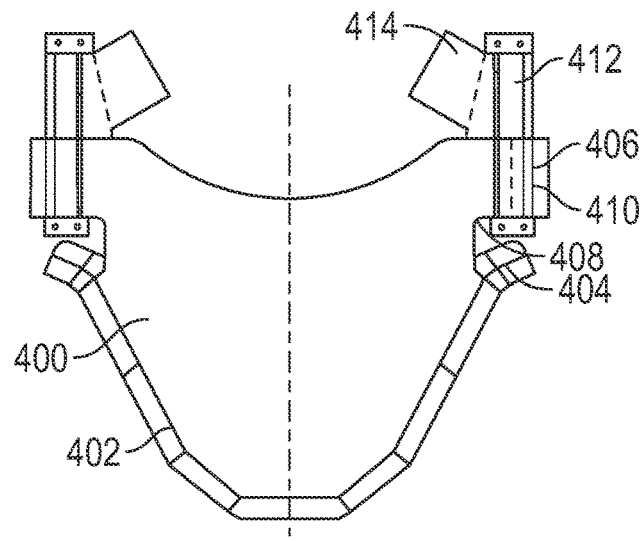
FIG. 40 is a plan view of a leaflet that can be used in a prosthetic heart valve, according to another embodiment.

FIGS. 40-46 show another embodiment of a leaflet and a method for forming a commissure from two leaflets. As shown in FIG. 40, a leaflet 400 comprises a lower edge portion 402 terminating at lower tabs 404, upper tabs 406 (also referred to as commissure tabs) spaced from the lower tabs 404 by gaps 408. The lower tabs 404 can be folded downwardly against the lower edge portion 402 to reinforce those areas of the leaflet and to move the bending axes of the upper sections of the edge portions 402 (the portions just below the commissures) inwardly away from the inner surface of the frame, as previously described.

Figure 41:
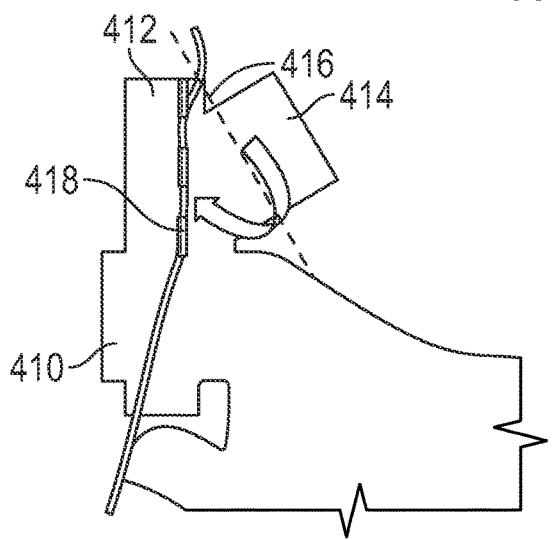
FIGS. 41, 42, 43, 44, and 45 show the formation of a commissure from two of leaflets of the type shown in FIG. 40, according to one embodiment.
Figure 42:
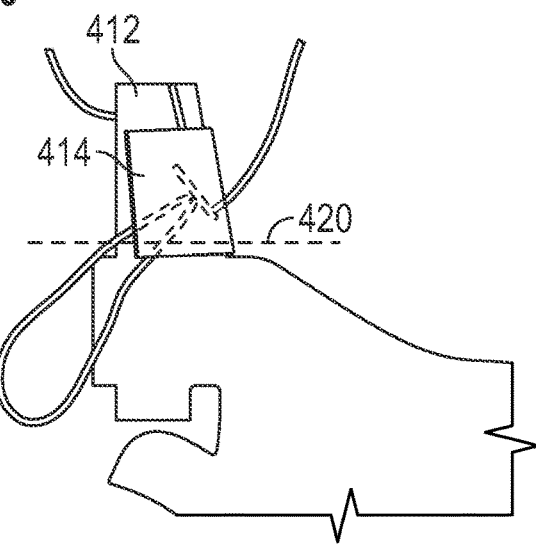
Figure 43:
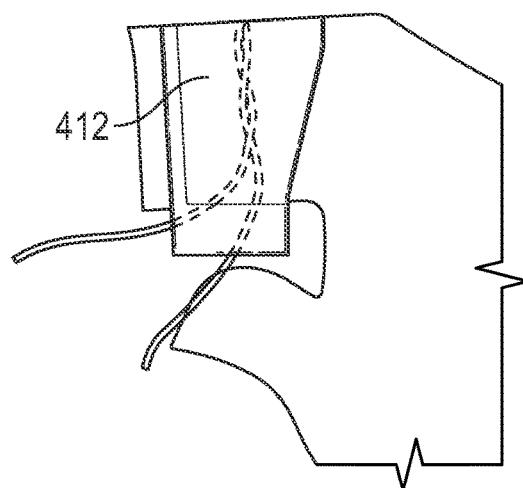

Each upper tab 406 includes a lower tab portion 410, an upper tab portion 412 extending from the lower tab portion, and a side tab portion 414 extending laterally inwardly from the upper tab portion. To form a commissure, a reinforcement member 418 (e.g., a multi-filament suture or a strip of fabric) can be placed vertically along the upper tab portion 412 in the manner shown in FIG. 41. The side tab portion 414 can then be folded along a fold line 416 against the upper tab portion 412 as shown in FIGS. 41-42. The dual layer of the side tab portion 414 and the upper tab portion 412 can then be folded along horizontal fold line 420 against the lower tab portion 410, as depicted in FIGS. 42-43.

Figure 44:
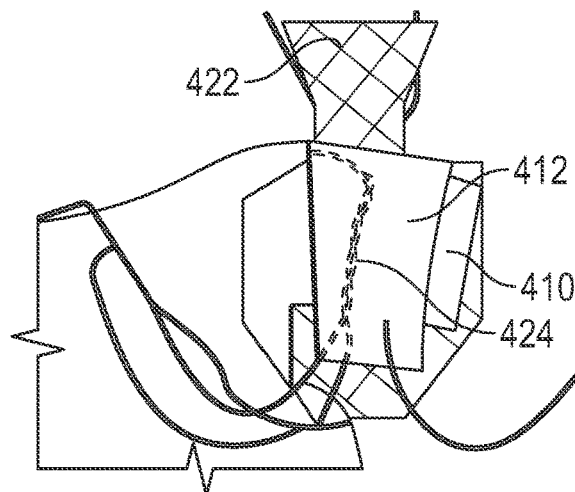
Figure 45:
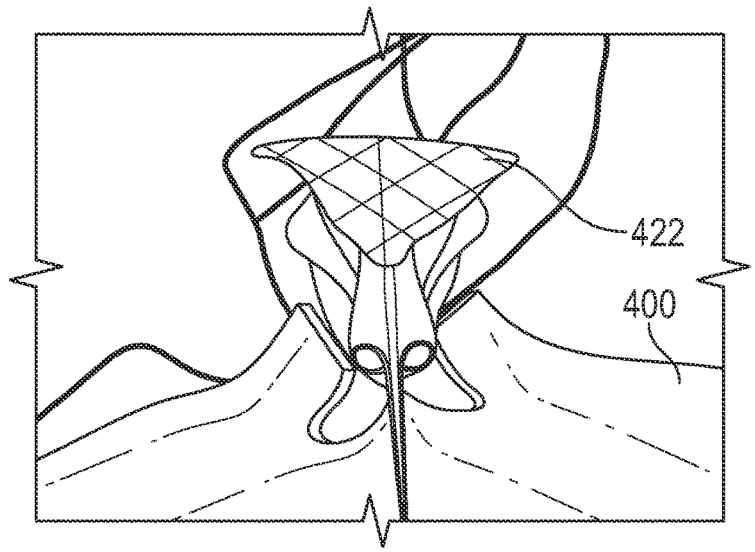
Figure 46:
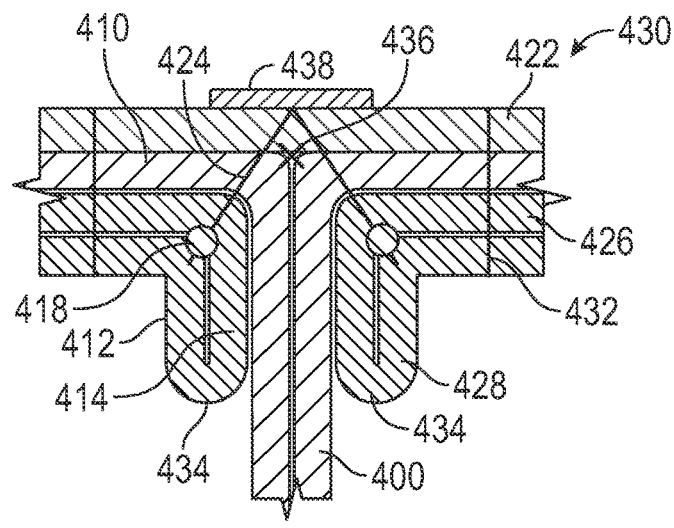
FIG. 46 is a cross-sectional view of a commissure formed from two leaflets of the type shown in FIG. 40, according to one embodiment.

As shown in FIG. 44, a commissure attachment member 422 can then be placed against the rear (outer) surface of the lower tab portion 410 and secured to the upper tab 406 with stitching 424 that extends through the upper tab portion 412, reinforcement member 418, the side tab portion 414, the lower tab portion 410, and the commissure attachment member 422. The three layers formed by the lower tab portion 410, the upper tab portion 414, and the side tab portion 414 can then be folded into an L-shape to form an outer folded portion 426 adjacent the commissure attachment member 422 and an inner folded portion 428 extending radially inwardly from the outer folded portion as shown in FIG. 46. As shown in FIG. 46, the tab layers of the outer folded portion 426 can be further secured to the commissure attachment member 422 with stitches 432. The upper tab 406 of another leaflet can be assembled in the same manner and secured to the same commissure attachment member 422 to form a commissure 430 as shown in FIGS. 45-46.

As described above, the stitches 424 can extend through each layer formed by the lower tab portion 410, the upper tab portion 414, and the side tab portion 414. As shown in FIG. 46, the stitches 424 from each commissure tab 406 can extend diagonally toward each other to compress the folded commissure tabs 406 against each other and the commissure attachment member 422. In alternative embodiments, the stitches 424 can be placed through the reinforcement member 418, the side tab portion 414 and the lower tab portion 410 prior to folding the upper tab portion and the side tab portion along fold line 420. In this manner, the stitches 424 need not extend through the upper tab portion 412, as depicted in FIG. 46. In some embodiments, another reinforcement member 438 can be placed against the outer surface of the commissure reinforcement member 422 (FIG. 46). The stitches 424 from each commissure tab 406 can extend through the reinforcement member 438 at the same location as shown or at spaced apart locations.

The commissure 430 can function similar to the commissure 328 described above. Thus, during normal valve cycling, the leaflets 400 can articulate about respective axes at the inner ends 434 of the tab layers 412. The compression of the folded commissure tabs 406 by stitches 424 helps maintain the normal bending axes of the leaflets 400 away from the frame. During valve deployment, the leaflets can splay apart from each other at an axis 436 adjacent the commissure attachment member 422.

Figure 47:
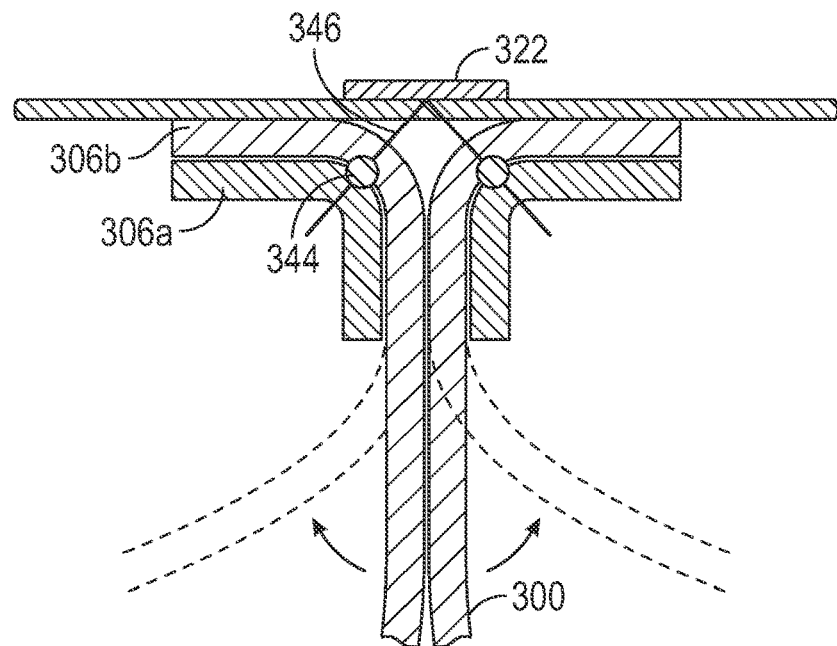
FIG. 47 is a cross-sectional view of a commissure formed from two leaflets of the type shown in FIG. 33, according to another embodiment.

FIG. 47 shows an alternative configuration for forming a commissure. The embodiment of FIG. 47 is similar to the embodiment of FIGS. 33-37 except that a vertical reinforcement member 344 can be placed between two layers of the commissure tab of the leaflet. The commissure can be formed by placing the reinforcement member 344 on tab portion 306*a* prior to folding tab portion 306*a* along fold line 308. After folding the commissure tab 306, the folded layers 306*a*, 306*b* can be secured to the commissure attachment member 322 with stitches 346 that extend through the reinforcement member 344, both tab layers 306*a*, 306*b*, and the commissure attachment member 322.

Figure 48:
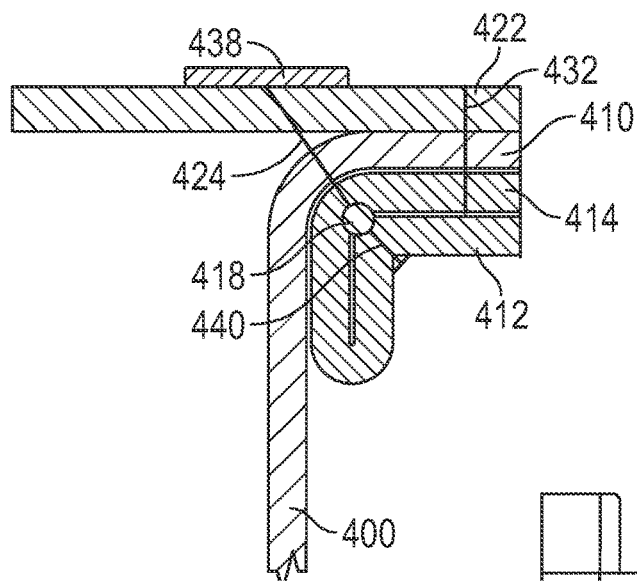
FIG. 48 is a cross-sectional view of a commissure formed from two leaflets of the type shown in FIG. 40, according to another embodiment.

FIG. 48 shows an alternative configuration for forming a commissure similar to FIG. 46, except that each folded commissure tab 406 is secured to a separate reinforcing member 438 (one of which is shown in FIG. 48). Also, stitches 440 can secure the side tab portion 412 to the reinforcing member 418.

Figure 49:
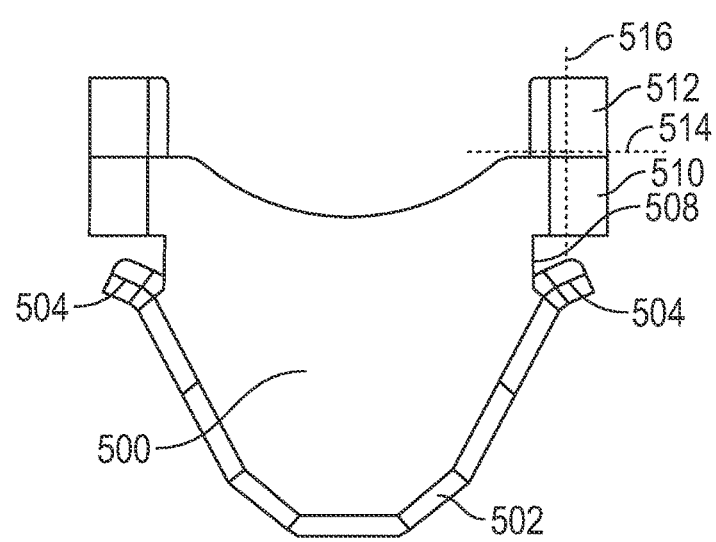
FIG. 49 is a plan view of a leaflet that can be used in a prosthetic heart valve, according to another embodiment.

FIGS. 49-54 show another embodiment of a leaflet and a method for forming a commissure 32 from two leaflets. As shown in FIG. 49, a leaflet 500 comprises a lower edge portion 502 terminating at lower tabs 504, upper tabs 506 (also referred to as commissure tabs) spaced from the lower tabs 504 by gaps 508. The lower tabs 504 can be folded downwardly against the lower edge portion 502 to reinforce those areas of the leaflet and to move the bending axes of the upper sections of the edge portions 502 (the portions just below the commissures) inwardly away from the inner surface of the frame, as previously described.

Figure 50:
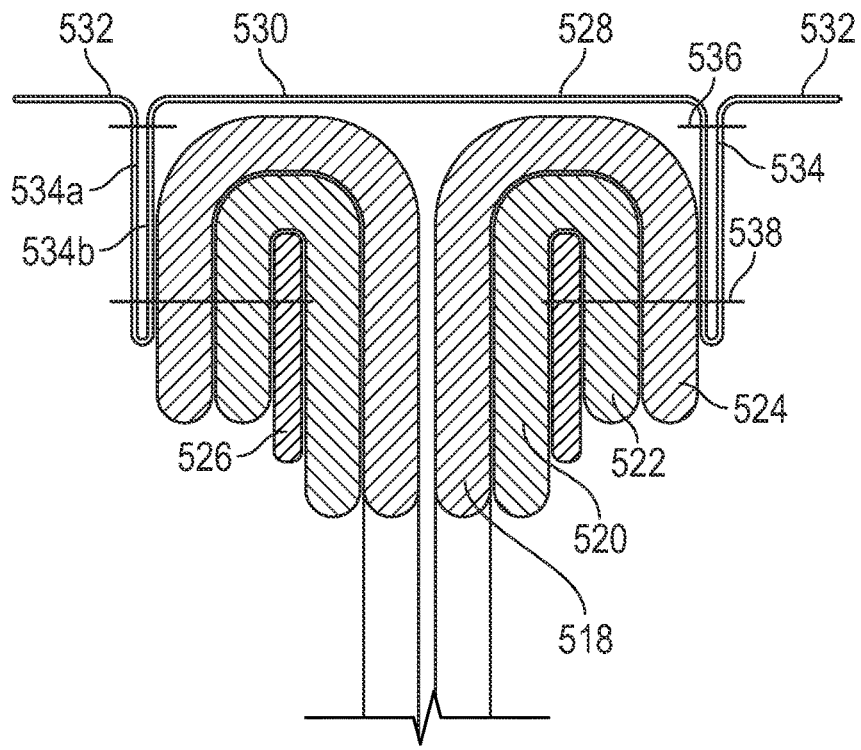
FIGS. 50-51 are cross-sectional views of two embodiments of a commissure formed from two leaflets of the type shown in FIG. 49.
Figure 51:
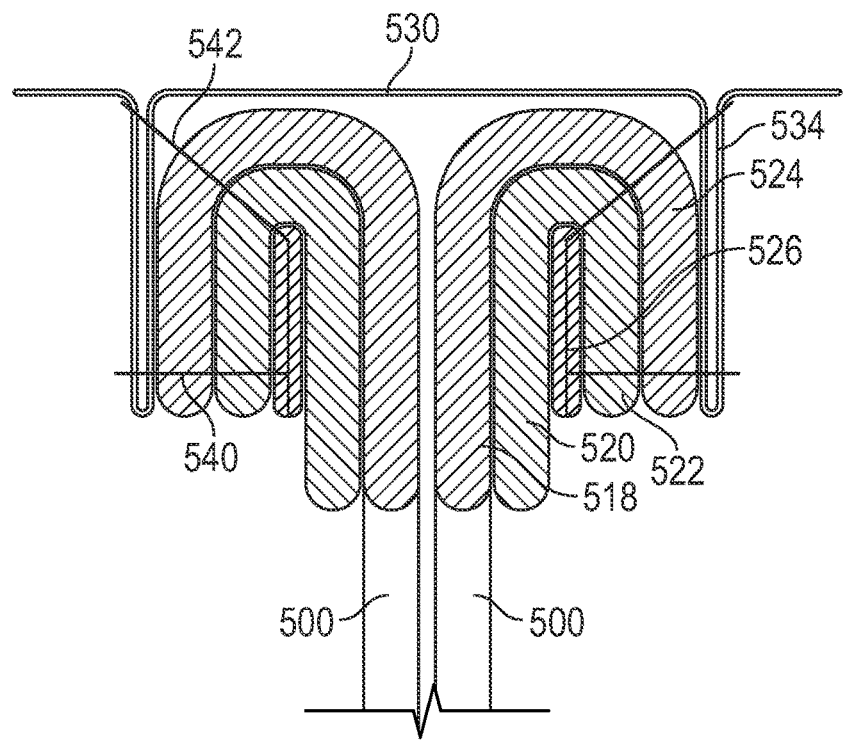
Figure 52:
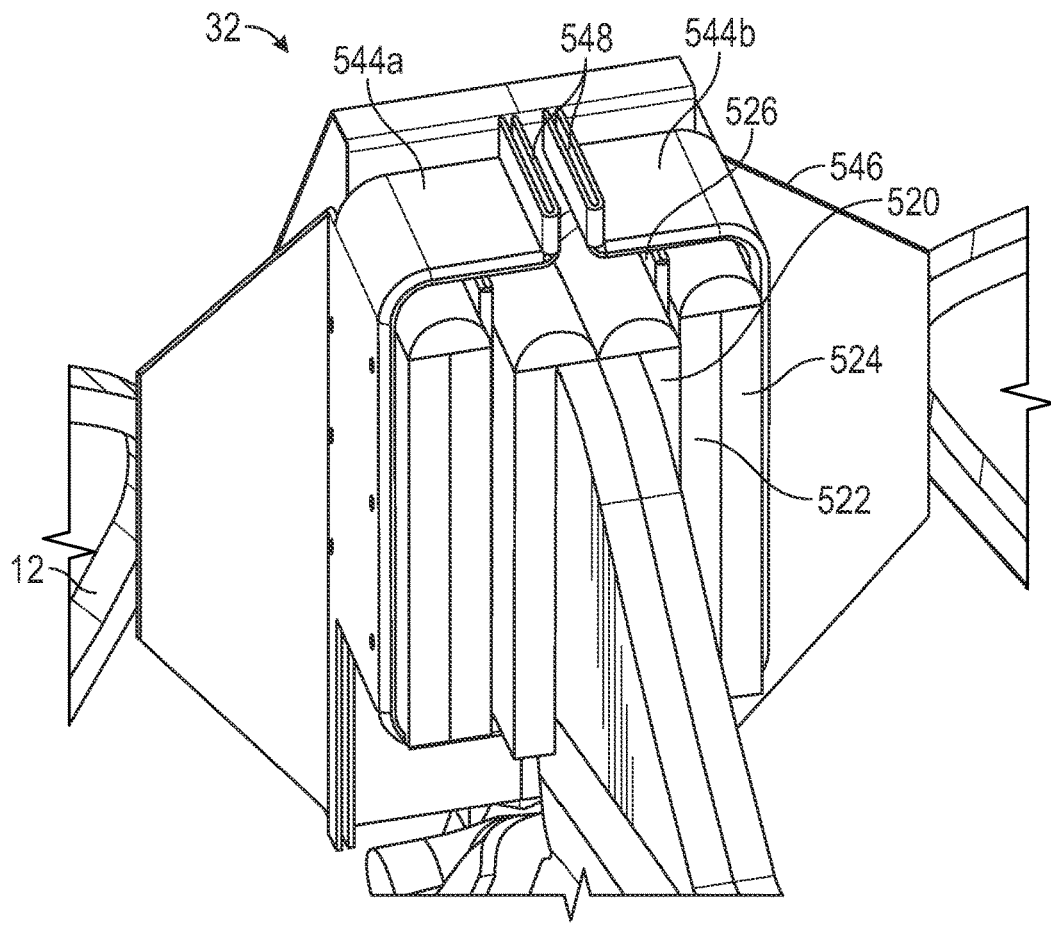
FIGS. 52, 53, 54, and 55 are various views showing the attachment of the commissure of FIG. 50 or 51 to the frame of a prosthetic heart valve using a commissure attachment member.

Each commissure tab 506 includes a lower tab portion 510 and an upper tab portion 512. To form a commissure, the upper tab portion 512 is folded along fold line 514 against the lower tab portion 510. The dual layer comprising tab portions 510, 512 can then be folded along a vertical fold line 516 to form a first layer 518, a second layer 520, a third layer 522, and a fourth layer 524 from each commissure tab 506, as depicted in FIGS. 50-52. A reinforcement member 526, such as strip of fabric (e.g., PET), can be positioned between the second layer 520 and the third layer 522.

The commissure tab 506 of another leaflet 500 is folded in the same manner and placed against the folded commissure tab of the first leaflet within a commissure attachment member 528. The commissure attachment member 528 can be folded as shown in FIG. 50 to form a central outer portion 530, outer end portions 532, and side portions 534, each comprising first and second layers 534*a*, 534*b* of material extending from respective ends of an end portion 532 and the central outer portion 530. The side portions 534 can be placed against respective fourth layers 524 of the commissure tabs.

As shown in FIG. 50, the layers 534*a*, 534*b* of each side portion 534 can be secured to each other with stitching 536. Each side portion 534 can be secured to a commissure tab 506 with stitching 538 extending through a respective reinforcing member 526, respective third and fourth layers 522, 524, and both layers of a respective side portion 534. The commissure attachment member 528 can be secured to the struts 22 of a frame 12 with sutures or other techniques or mechanisms.

FIG. 51 shows another way of securing the folded commissure tabs 506 to the commissure attachment member 530. As shown in FIG. 51, for each commissure tab, a row of laterally extending stitches 540 can be used to secure the inner end portions of the layers 534*a*, 534*b* of the side portion, the third and fourth layers 522, 524, and the reinforcing member 526. A diagonally extending row of stitches 524 can be used to secure the reinforcing member 526, the third and fourth layers 522, 524, and the rear end portions of layers 534*a*, 534*b* of the side portion.

Figure 53:
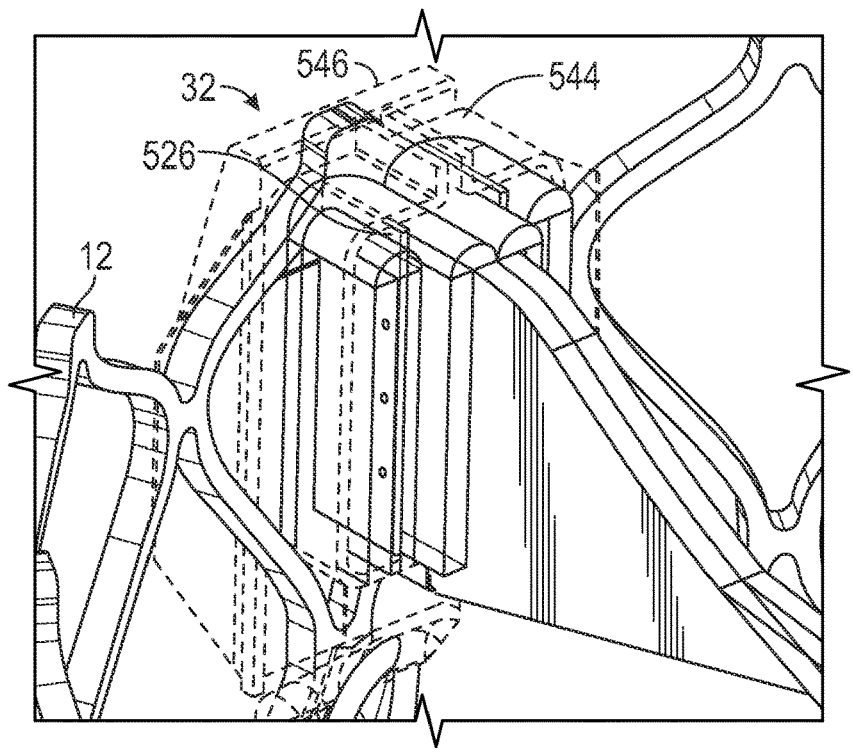

As shown in FIG. 52-53, each commissure 32 can include an inner sleeve 544 and an outer support member 546. The inner sleeve 544 can comprise first and second portions 544*a*, 544*b*, each of which extends around the outer side as well as the upper and lower portions of a respective folded commissure tab 506. The adjacent upper ends 548 of the first and second portions 544*a*, 544*b* can be secured to each other (e.g., with sutures) at the center of the commissure 32. The adjacent lower ends of the first and second portions 544*a*, 544*b* can be secured to each other (e.g., with sutures) in a similar manner at the center of the commissure 32. Each of the side portions 534 of the commissure attachment member 528 can be secured to one of the first and second portions 544*a*, 544*b* of the inner sleeve (e.g., with sutures). The outer support member 546 can be secured to the central outer portion 530 and/or the end portions 532 of the commissure attachment member 528 (e.g., with sutures).

Figure 54:
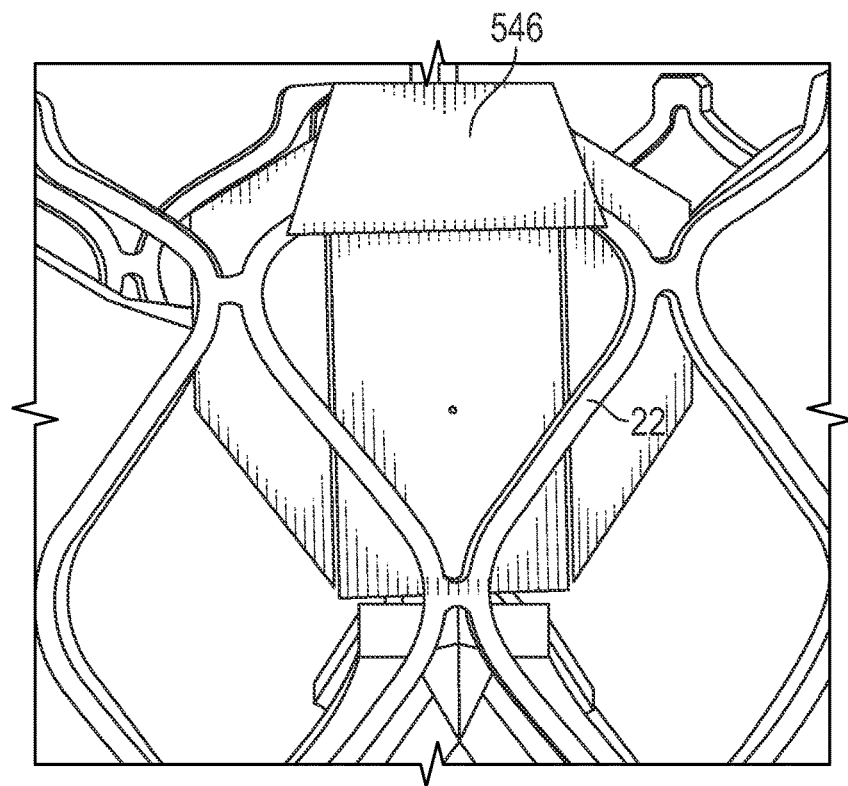

As shown in FIG. 54, at least a portion of the outer support member 546 can be positioned outside of the frame 12. The outer support member 546 can be secured (e.g., with sutures) to each strut 22 of a set of struts forming a cell of the frame. In the illustrated embodiment, for example, the outer support member 546 can be sutured to each strut of a diamond-shaped cell comprised of four struts 22. The inner sleeve 544 and the outer support member 546 can comprise any suitable relatively flexible and soft material as previously described for the reinforcement members and the commissure attachment members of the embodiments described above. In particular embodiments, the inner sleeve 544 and the outer support member 546 comprise PET fabric.

Figure 55:
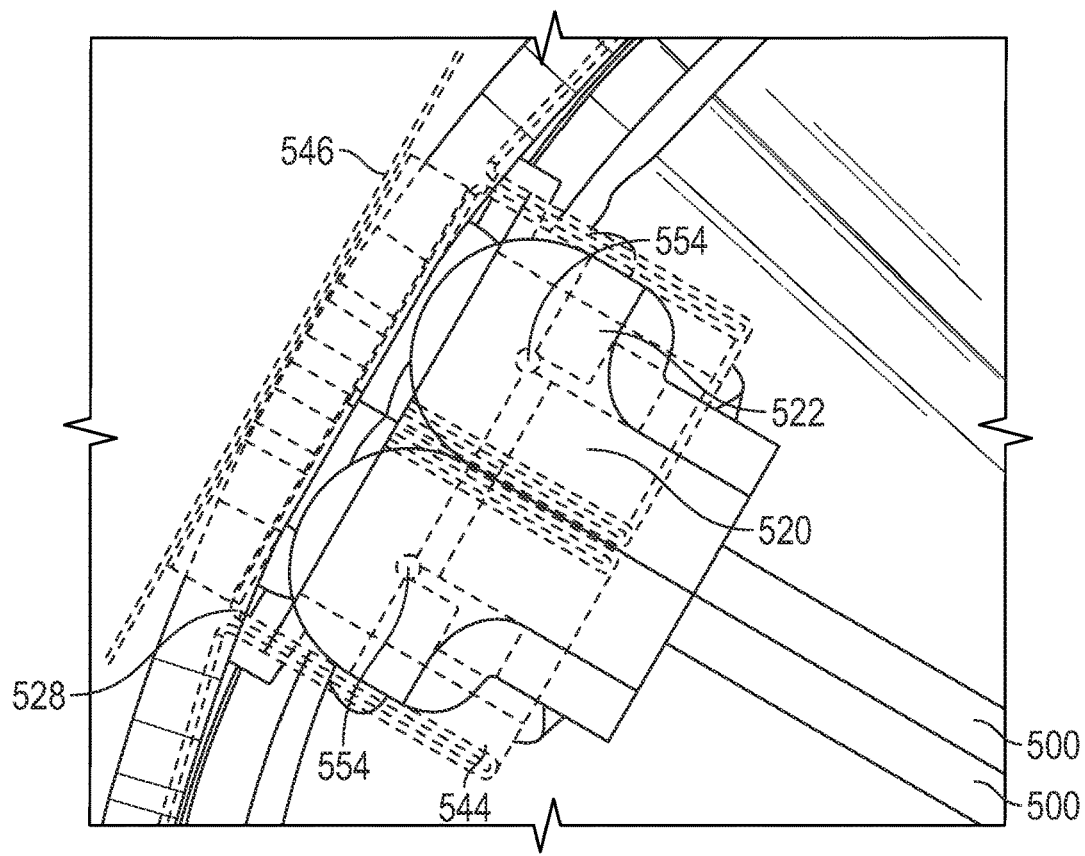

FIG. 55 shows a modification of the commissure 32 shown in FIGS. 52-54. The embodiment of FIG. 55 can be the same as the embodiment of FIGS. 52-54, except that the former includes reinforcing members 554 in the form of multi-filament sutures positioned between the second and third layers 520, 522 of each commissure tab 506.

Figure 56:
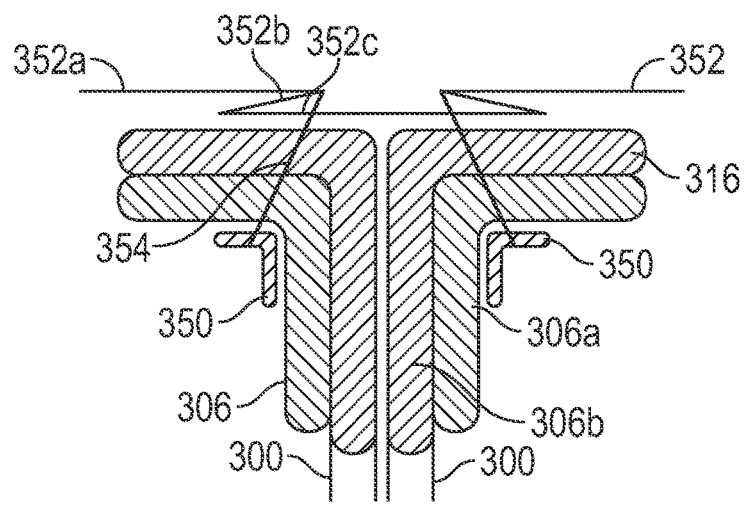
FIG. 56 is a cross-sectional view of another embodiment of a commissure formed from two leaflets of the type shown in FIG. 33.

FIG. 56 shows an alternative embodiment for forming a commissure from two leaflets 300. The commissure tabs 306 can be folded in a manner similar to that described above for the embodiment of FIGS. 33-37. As shown, a reinforcement member 350 (e.g., strips of PET fabric or other material) can be placed at the fold of each layer 306*a*. A commissure attachment member 352 can be placed against the outer folded portions 316 of each layer 306*b* and folded in the manner shown in FIG. 56 to create three layers of material 352*a*, 352*b*, 352*c* at each layer 306*b*. For each commissure tab 306, stitches 354 can be used to secure the reinforcement member 350, layers 306*a*, 306*b* and the three folded layers of the commissure attachment member 352.

Figure 57:
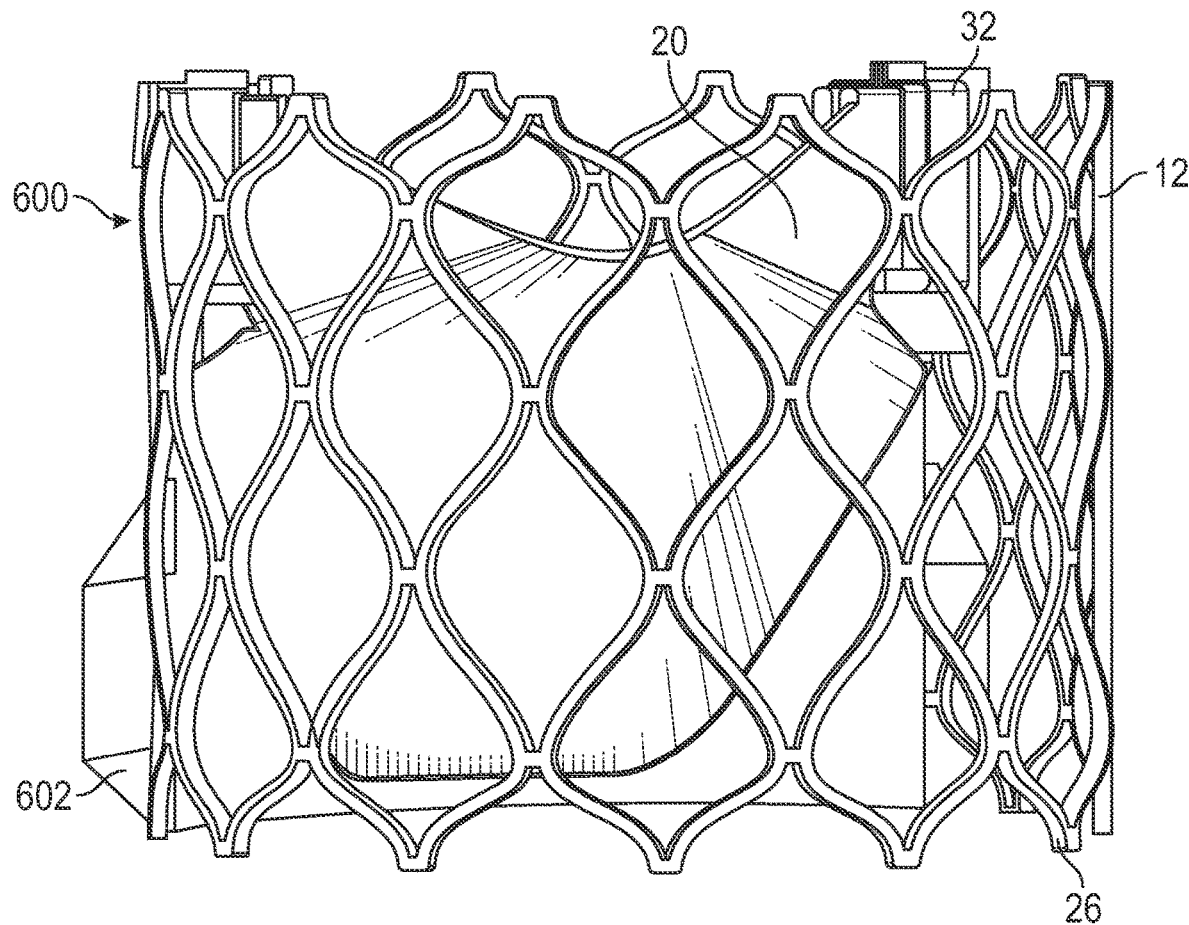
FIGS. 57 and 58 are side elevation and perspective views, respectively, of a prosthetic heart valve, according to another embodiment.
Figure 58:
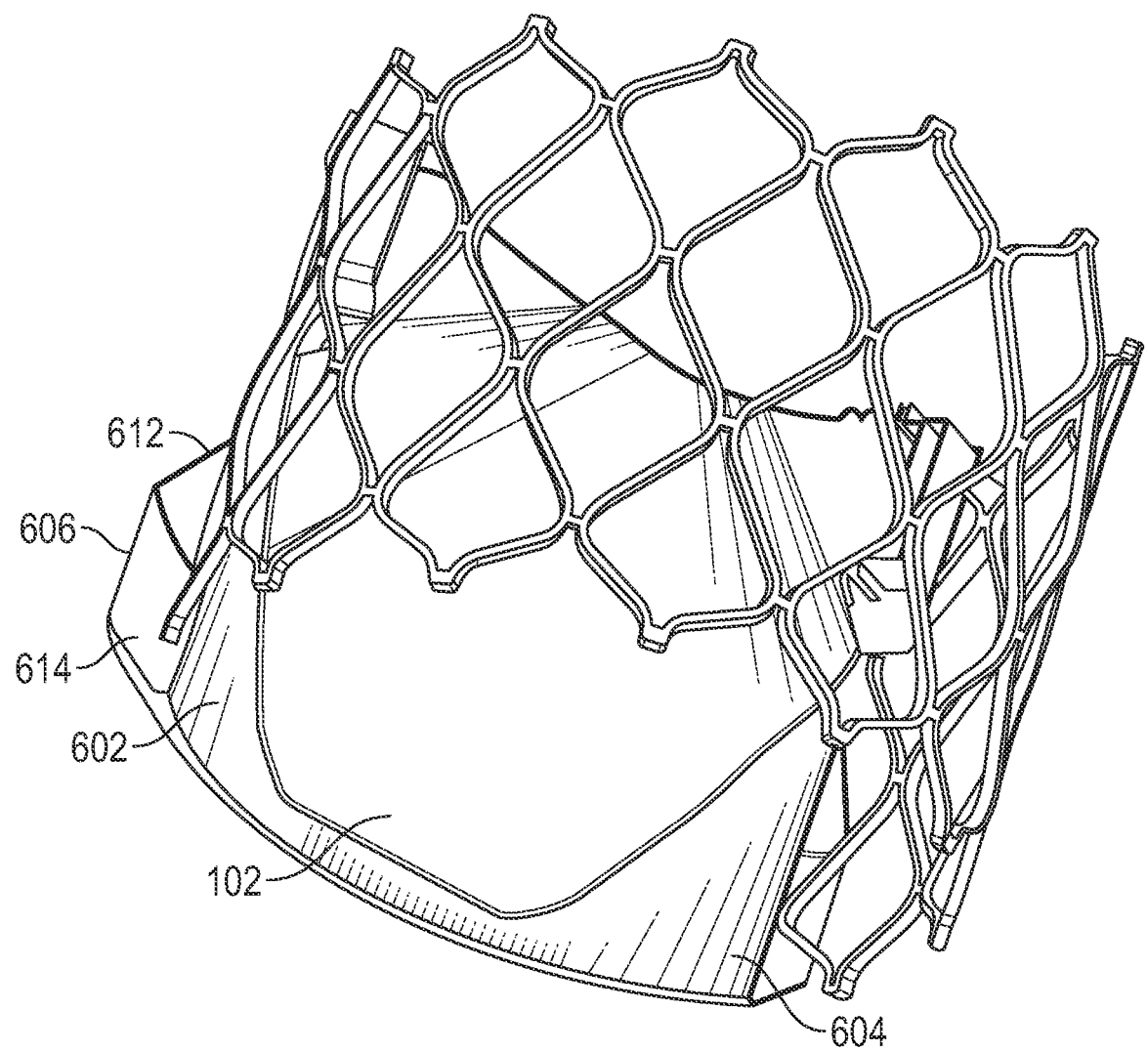
Figure 59:
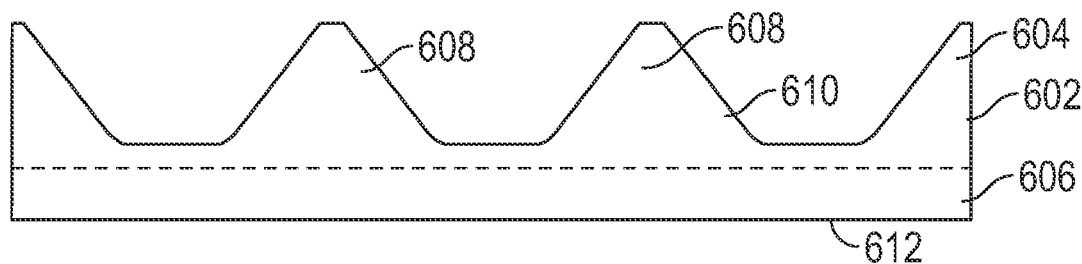
FIG. 59 is a plan view of the sealing member of the prosthetic heart valve of FIGS. 57-58, shown in a flattened configuration.

FIGS. 57-58 show a prosthetic valve 600, according to another embodiment. The prosthetic valve 600 can be similar to the prosthetic valve 10 described above except for the configuration of the sealing member. The prosthetic valve 600 in the illustrated embodiment comprises a sealing member 602 comprising an inner portion or layer 604 and an outer portion or layer 606. The inner layer 604 is mounted inside of the frame 12 and comprises three triangular shaped portions 608. FIG. 59 shows the sealing member 602 in a flattened configuration prior to attachment to the frame. The half triangular portions at each end of the sealing member form a triangular portion 608 when the sealing member is formed into a tubular or annular shape with the ends connected to each other.

The upper edge portion 610 of the inner layer is shaped to correspond to the shape of the lower edge portions 102 of the leaflets 20. The lower edge portions 102 of the leaflets 20 can be connected directly to the upper edge portion 610 of the inner layer 602 (e.g., with sutures), using connecting skirts (e.g., any of the connecting skirts described herein, such as skirts 100) or other mounting techniques described herein. The upper edge portion 610 of the inner layer 602 can be secured to the struts 22 of the frame 12, such as with the sutures used to connect the inner layer to the leaflets or with separate sutures that extend around the struts 22 and through the inner layer. The inner layer 604 functions to prevent antegrade blood from flowing outwardly through the cells of the frame below the inflow edges of the leaflets.

The outer layer 606 can be wrapped around the inflow end 26 of the frame and secured (e.g., with sutures) along its upper edge portion 612 to the struts 22 on the outside of the frame 12. Individual sutures can be used to secure the outer layer 606 at circumferentially spaced apart locations to the apices at the inflow end 26 of the frame.

The outer layer 606 can be shaped or configured to extend radially outwardly from the frame when the prosthetic valve is radially expanded to its functional size to create a space 614 between the frame and the outer layer 606. Upon deployment in a patient's body, retrograde blood can flow over the outer surface of the leaflets 20, through the cells of the frame, and into the space 614 inside of the outer layer 606 to facilitate creation of a seal against the surrounding tissue. The absence of material inside of the frame facing the movable portions of the leaflets 20 can reduce the overall crimp profile of the prosthetic valve and can inhibit abrasion of the leaflets 20, especially in cases where the prosthetic valve is not fully expanded to its nominal size. Consequently, this can allow the prosthetic valve to be implanted in a wider range of patient annulus sizes.

The sealing member 602 can be formed from the same materials and using the same techniques as described above for the sealing member 16.

Figure 60:
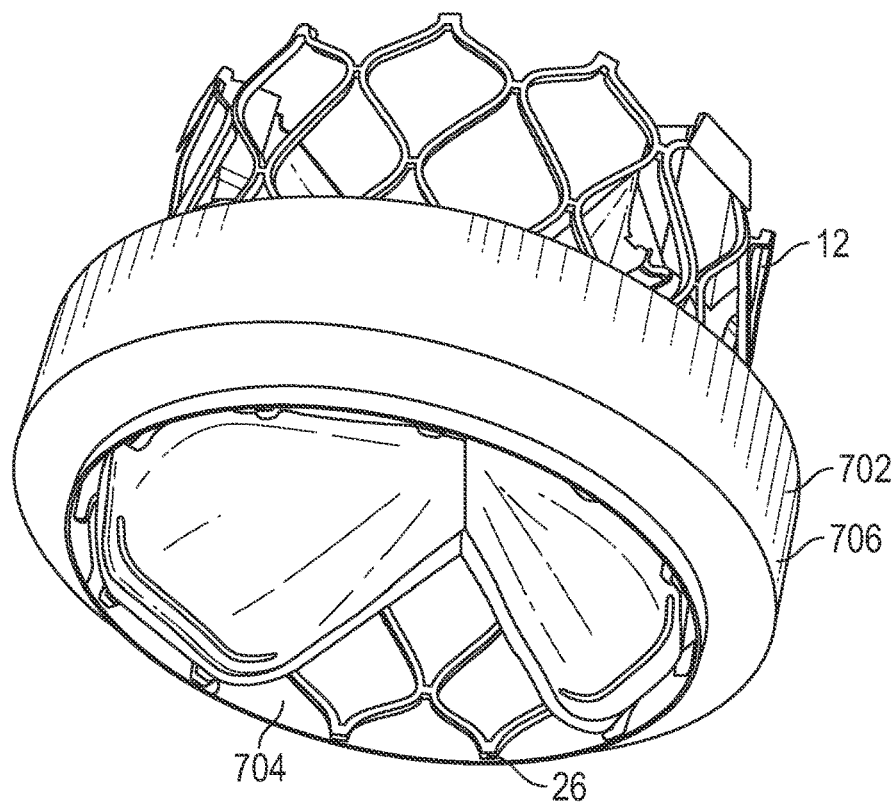
FIGS. 60 and 61 are perspective and cross-sectional views, respectively, of a prosthetic heart valve, according to another embodiment.
Figure 61:
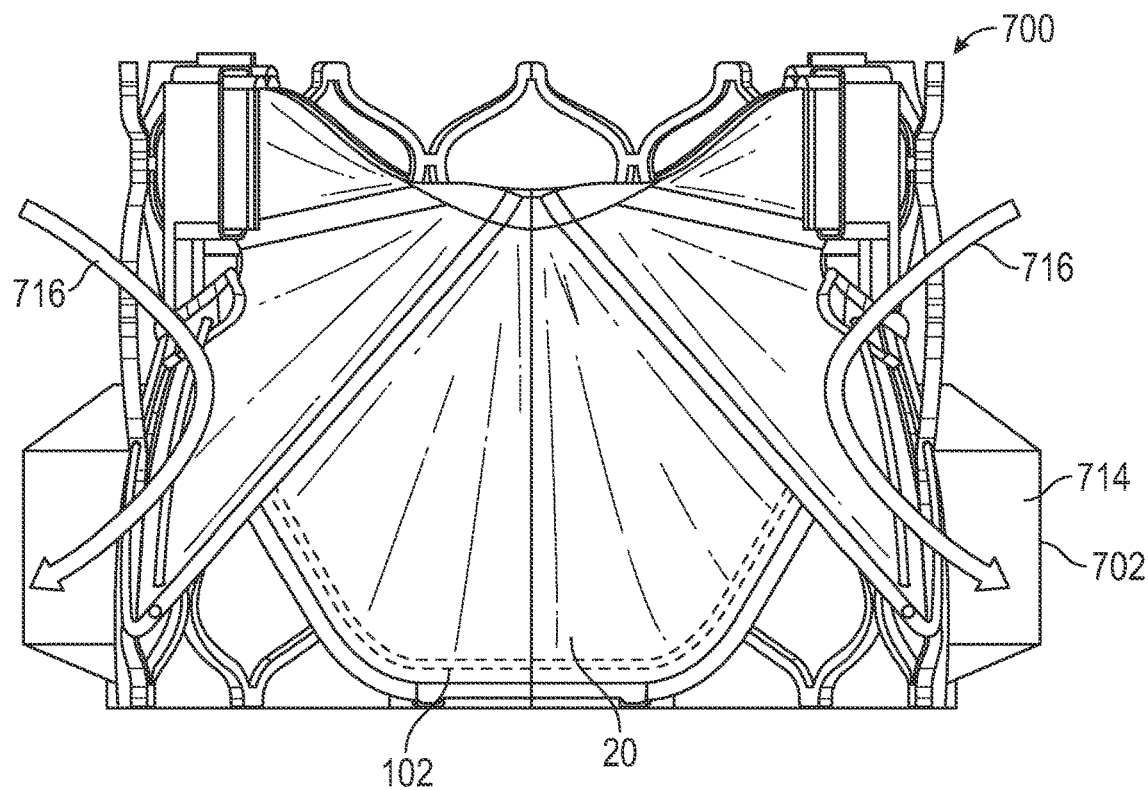

FIGS. 60-61 show a prosthetic valve 700, according to another embodiment. The prosthetic valve 700 can similar to the prosthetic valve 10 described above except for the configuration of the sealing member. The prosthetic valve 700 in the illustrated embodiment comprises a sealing member 702 comprising an inner portion or layer 704 and an outer portion or layer 706. The inner layer 704 is mounted outside of the frame 12 and comprises three triangular shaped portions 708. In particular embodiments, the triangular shaped portions 708 are connected only by a thin strip 705.

Figure 62:
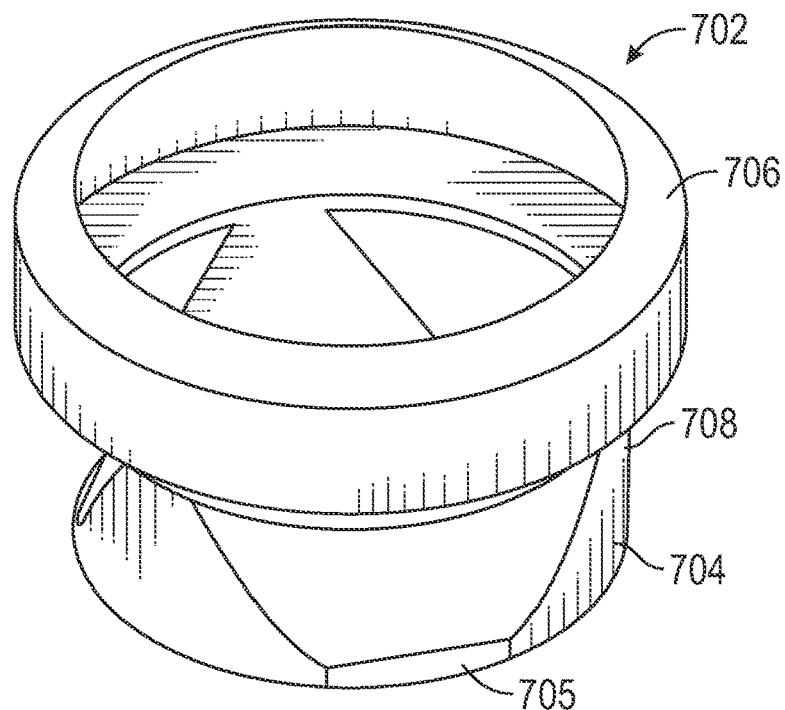
FIGS. 62, 63, and 64 show the sealing member of the prosthetic heart valve of FIGS. 60-61 being mounted on the frame of the valve.
Figure 63:
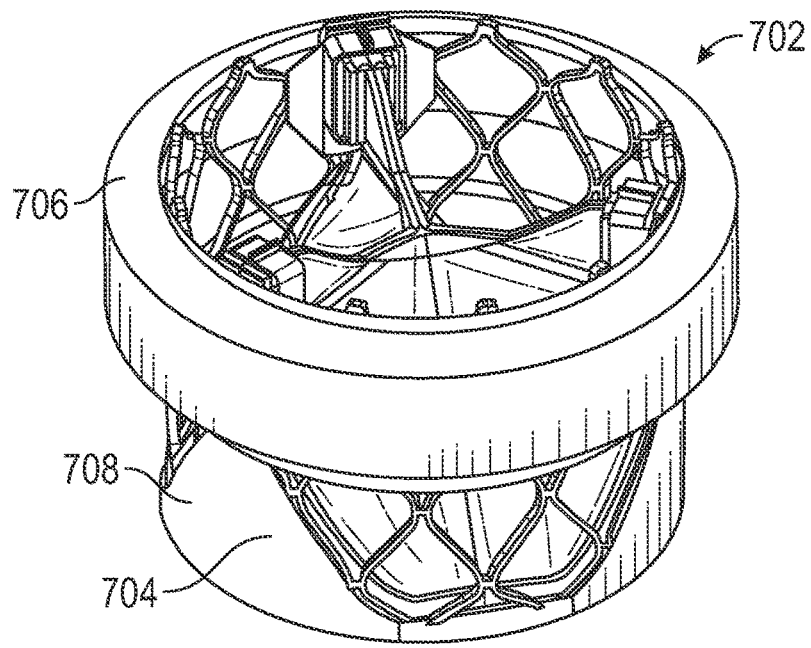

FIG. 62 shows the sealing member 702 prior to assembling it on the frame 12 and folded into its final shape. When mounting the sealing member 702 on the frame 12, the sealing member can first be placed on the frame as shown in FIG. 63 such that the inflow end portion of the inner layer 704 is adjacent the inflow end 26 of the frame. The triangular portions 708 are shaped to correspond to the shape of the lower edge portions 102 of the leaflets 20 and cover the openings in the frame between adjacent edge portions 102 underneath each commissure. By virtue of the shape of the triangular portions 708, the inner layer 704 does not cover the portions of the frame facing the outflow surfaces of the leaflets.

The lower edge portions 102 of the leaflets 20 can be connected directly to the upper edge portion 710 of the inner layer 704 (e.g., with sutures), using connecting skirts (e.g., any of the connecting skirts described herein, such as skirts 100) or other mounting techniques described herein. The inner layer 704 functions to prevent antegrade blood from flowing outwardly through the cells of the frame below the inflow edges of the leaflets.

Figure 64:
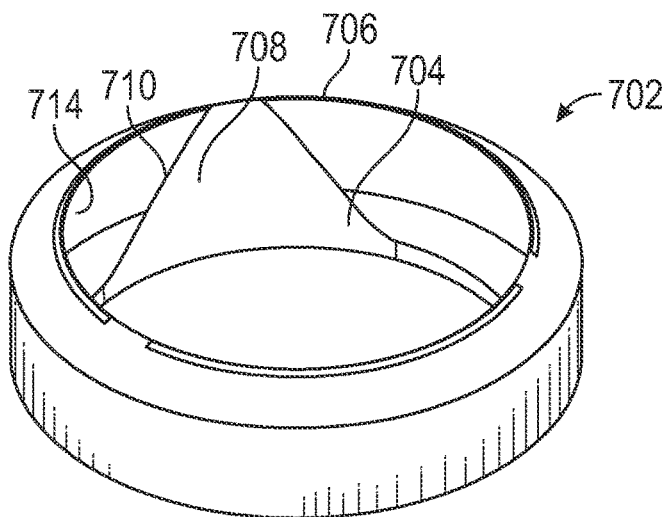

The outer layer 706 can then be folded over the inner layer 704 toward the inflow end 26 of the frame such that the upper end of the pre-folded outer layer becomes the lower (inflow) end of the outer layer and lies adjacent the inflow end 26 of the frame, as shown in FIG. 60. Folding the outer layer over the inner layer inverts the outer layer such that the inner surface of the pre-folded outer layer becomes the outer surface of the outer layer and the outer surface of the pre-folded outer layer becomes the inner surface of the outer layer in its folded, assembled state. FIG. 64 shows the sealing member 702 in its final, folded state apart from the rest of the prosthetic valve for purposes of illustration. After folding the outer layer 706, the inflow and/or outflow ends of the outer layer can be secured to the struts 22 of the frame (e.g., with sutures).

The sealing member 702 can be formed from the same materials and using the same techniques as described above for the sealing member 16. In alternative embodiments, the inner layer 704 and the outer layer 706 can be separate pieces of material, which can be secured to each other (e.g., with sutures) at their inflow ends and/or outflow ends.

Similar to the embodiment of FIGS. 57-59, the outer layer 706 can be shaped or configured to extend radially outwardly from the frame when the prosthetic valve is radially expanded to its functional size to create a space 714 between the frame and the outer layer 706. Upon deployment in a patient's body, retrograde blood can flow over the outflow surface 70 of the leaflets 20, through the cells of the frame, and into the space 714 inside of the outer layer 706 in the direction of arrows 716 to facilitate creation of a seal against the surrounding tissue. The triangular shaped portions 708 prevent antegrade blood from flowing through the frame at locations between the cusp edge portions 102 of the leaflets. The absence of material inside of the frame can reduce the overall crimp profile of the prosthetic valve and can inhibit abrasion of the leaflets 20, especially in cases where the prosthetic valve is not fully expanded to its nominal size. Consequently, this can allow the prosthetic valve to be implanted in a wider range of patient annulus sizes.

Figure 65:
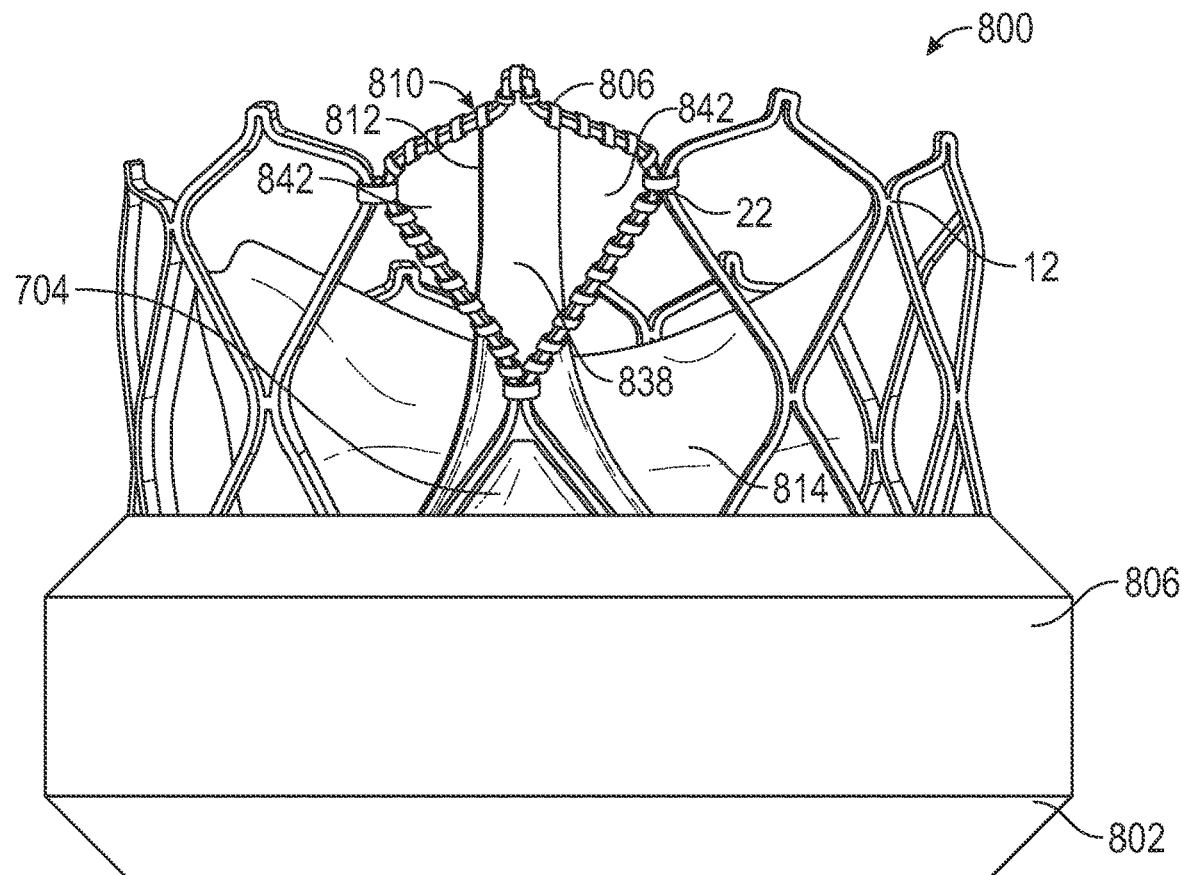
FIGS. 65 and 66 are perspective views of a prosthetic heart valve, according to another embodiment.
Figure 66:
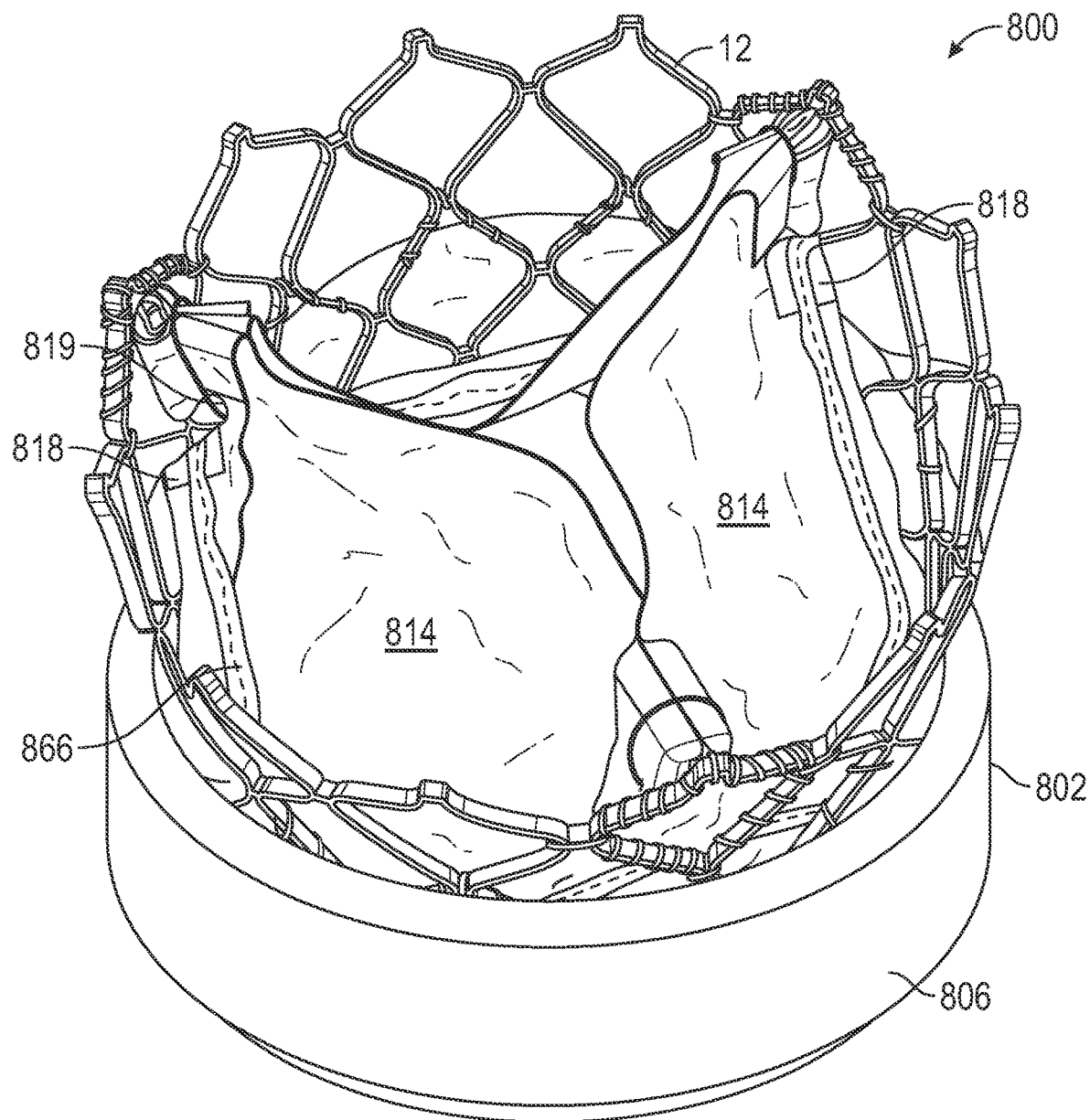

FIG. 65 shows a prosthetic valve 800, according to another embodiment. The prosthetic valve 800 can include a sealing member 802 mounted to the frame 12 as described above in connection with the embodiment of FIGS. 60-63. The prosthetic valve 800 can include leaflets 814 connected to each other at their outflow ends to form commissures 810 that are mounted to the cells at the outflow end of the frame. The commissures 810 can be formed by folding commissure tabs of the leaflets and securing them to a commissure attachment member 812. Each commissure attachment member 812 can be sutured to four struts 22 that define a closed cell 24 of the frame. A method for forming the commissures 810 and mounting them to a cell 24 via the commissure attachment members 812 is described in detail below.

Figure 68:
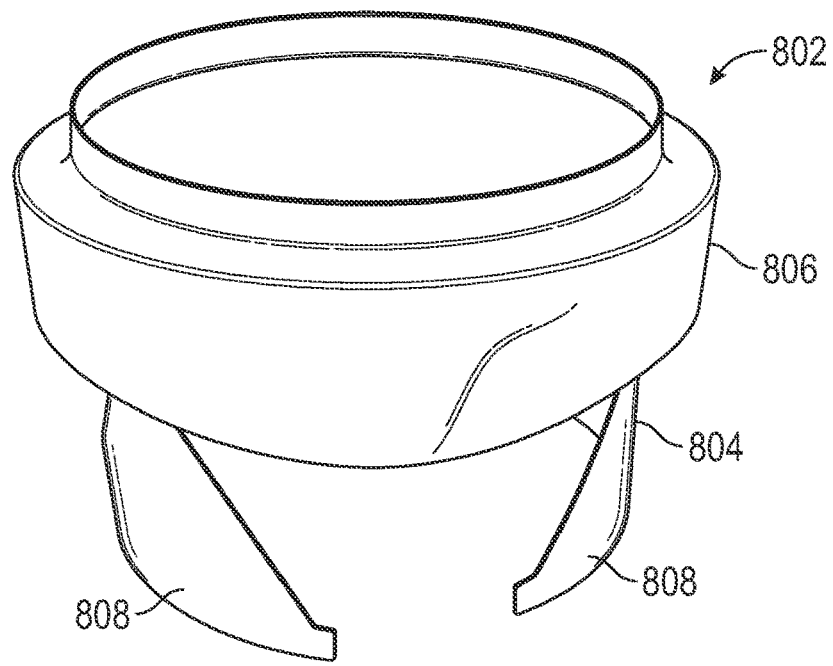
FIG. 68 is a perspective view of the sealing member of the prosthetic heart valve of FIGS. 65-66.

FIG. 68 show the sealing member 802 apart from the other components of the prosthetic valve. The sealing member 802 comprises an inner layer 804 and an outer layer 806. The inner layer 804 can comprise a plurality of triangular-shaped portions 808. The sealing member 802 can have the same or similar construction as the sealing member 702, except that the triangular-shaped portions 808 are not connected to each other at their lower (inflow) ends. The sealing member 802 can be mounted to frame 12 as described above in connection with sealing member 702.

Figure 75A:
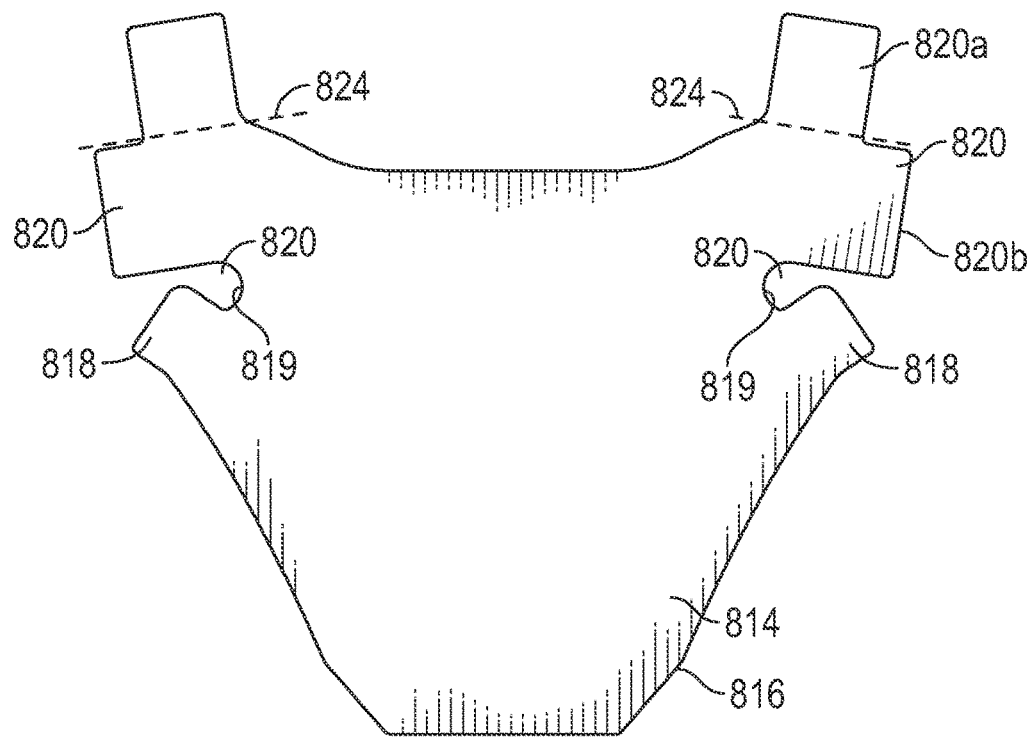
FIG. 75A is a plan view of the leaflet of FIG. 74, shown in a flattened configuration.

Referring to FIGS. 74-78, a method for forming the commissures 810 and mounting them to the frame 12 will be described. As best shown in FIG. 75, each leaflet 814 has a lower or cusp edge portion 816 that can be mounted to the frame 12 using any of the previously described embodiments. The lower edge portion 816 terminates at its upper ends at two laterally projecting integral lower tabs 818. Projecting from the upper corners of the leaflet 814 are integral upper tabs 820 (also referred to as commissure tabs). The upper tabs 820 can be spaced from the lower tabs 818 by side edges 819 forming laterally extending gaps or recesses 820 in the leaflet.

Figure 75B:
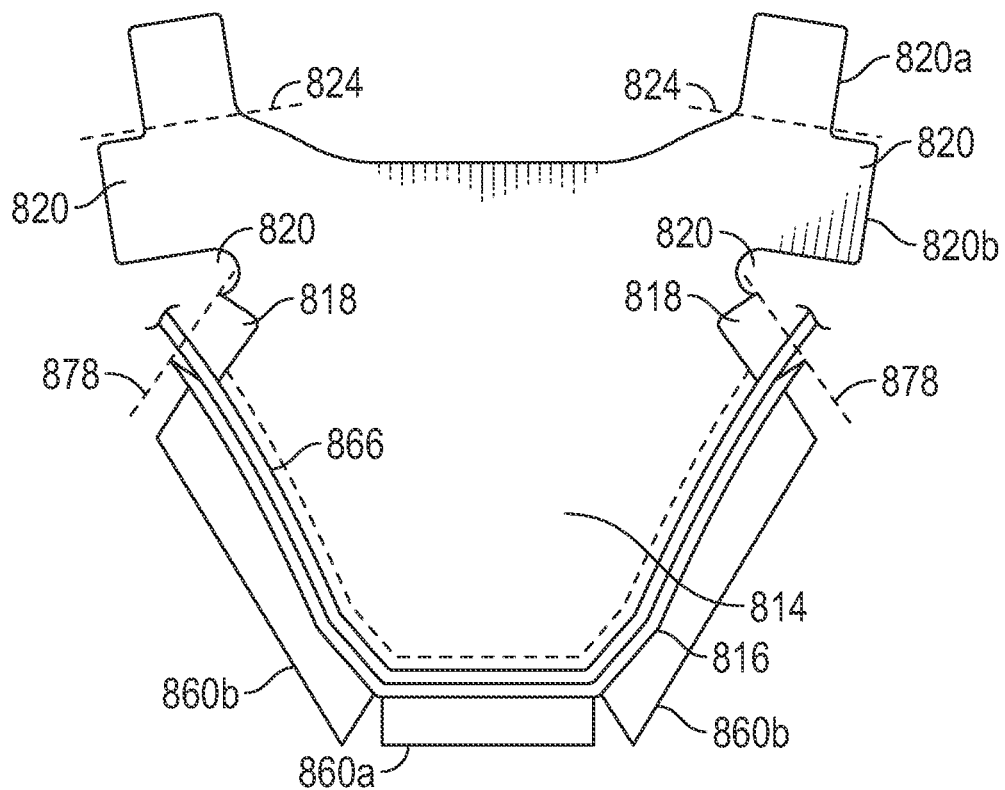
FIG. 75B is a plan view of the leaflet of FIG. 74 and the connecting skirt of FIG. 70 positioned along the cusp edge portion of the leaflet.
Figure 76:
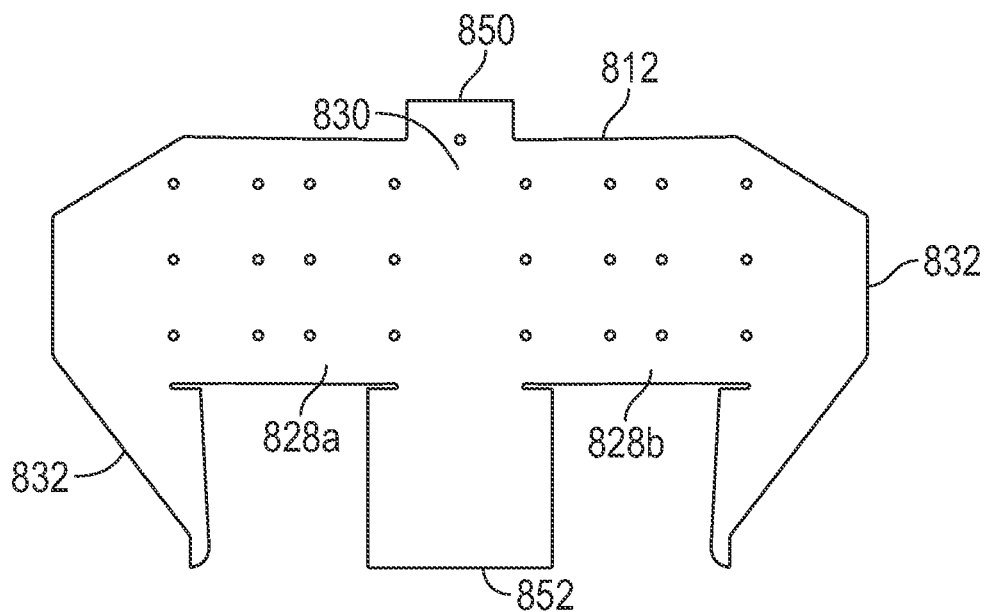
FIG. 76 is a plan view of an embodiment of a commissure attachment member, shown in a flattened configuration.

As shown in FIG. 75B, each upper tab 820 is folded along a fold line 814 to form first and second tab layers 820a, 820b, similar to the technique described above for leaflet 300 shown in FIGS. 33-37. The upper tab 820 is secured to a commissure attachment member 812, along with the upper tab 820 of an adjacent leaflet to form a commissure 810, as further described below. FIG. 76 shows a commissure attachment member 812 in a flattened configuration prior to folding and attachment to the leaflets. Each commissure attachment member 812 in the illustrated configuration comprises first and second side portion 828a, 828b projecting laterally from a central portion 830. As shown, the outer peripheral edges 832 of the side portions 828a, 828b can be shaped to correspond to one half of a diamond-shaped cell 24 of the frame 12 to facilitate mounting of the commissure attachment member 812 to the struts 22 of the frame 12, as further described below.

Figure 77:
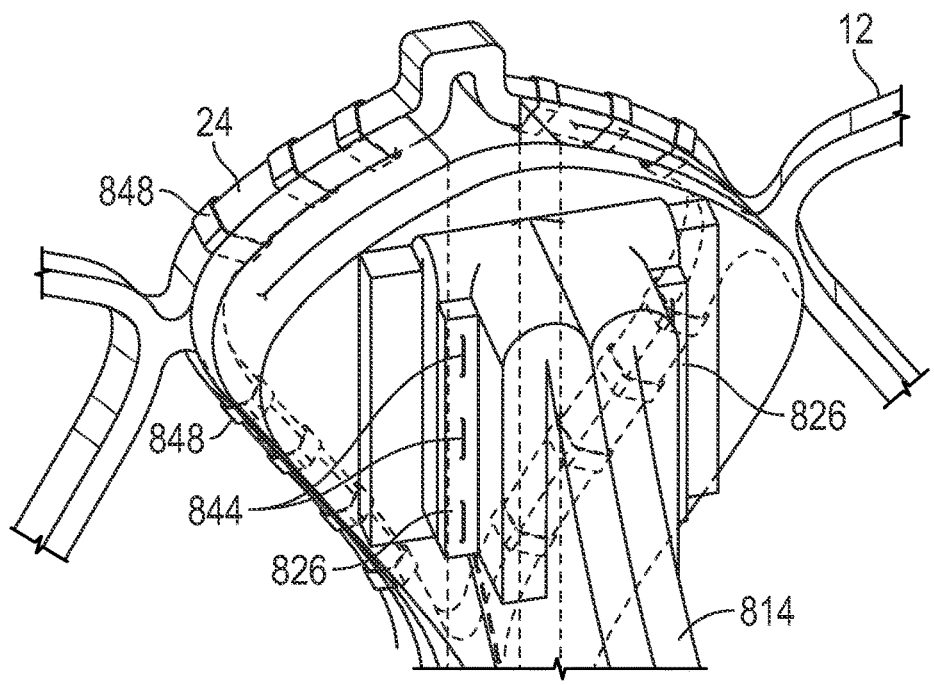
FIGS. 77 and 78 are perspective and cross-sectional views, respectively, of one of the commissures of the prosthetic heart valve of FIGS. 65-66.
Figure 78:
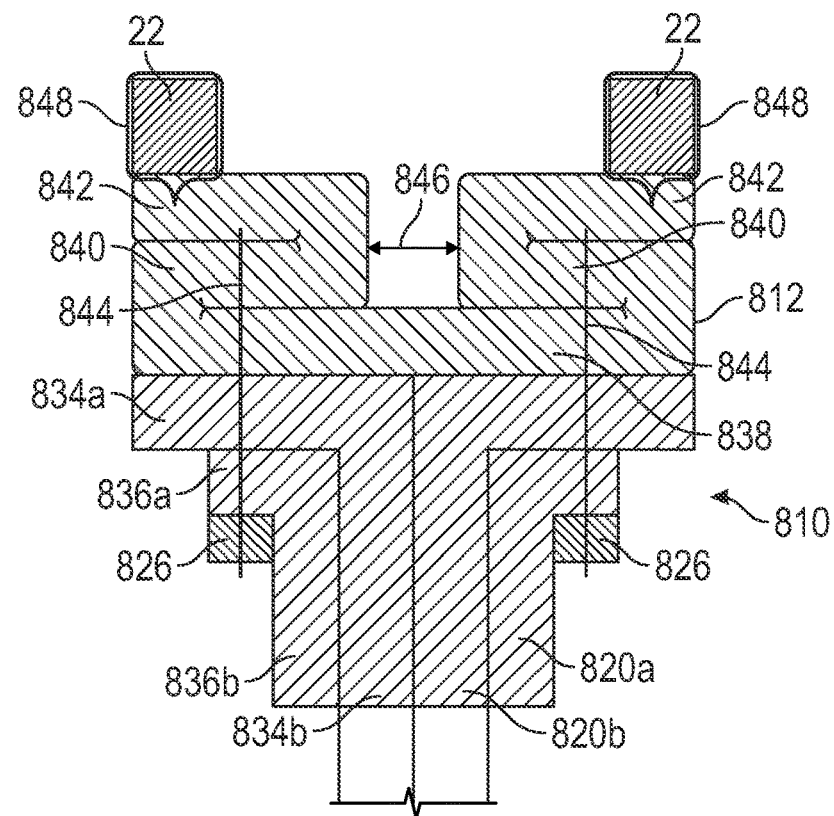

Referring to FIGS. 77-78, after the upper tab 820 of a leaflet 814 is folded, a vertical reinforcement 826 can be secured to the inner surface of tab layer 820a, such as with stitching. The folded tab layers 820a, 820b can be secured to a side portion 828a or 828b of the commissure attachment member 812. The folded tab layers also can be folded along a vertical fold line at the reinforcement 826 in an L-shape such that the tab layer 820b forms a first circumferentially extending layer 834a and a first radially extending layer 834b that is generally perpendicular to the layer 834a and the tab layer 820a forms a second inner circumferentially extending layer 836a and a radially extending layer 836b that is generally perpendicular to the layer 836a. Another upper tab 820 of an adjacent leaflet 814 can be similarly folded and secured to the other side portion 828a or 828b of the commissure attachment member 812.

The commissure attachment member 812 can be folded as shown in FIG. 78 to form an inner layer 838 and two intermediate layers 840 and two outer layers 842. Each folded upper tab 820 can be secured to the inner layer 383 and an intermediate layer 840 with stitching 844. In the illustrated embodiment, stitching 844 is shown extending through the reinforcement member 826, a layer 836a, a layer 834a, layer 838, and a layer 840. However, during the assembly process, multiple stitches can be employed to secure each layer to an adjacent layer as each folded is created. For example, layers 834a, 836a can be secured to each other and a reinforcement member 826 with separate stitching, and additional stitching can then be used to secure the leaflet layers to the inner layer 838 of the commissure attachment member 812, and further stitching can be used to secure an intermediate layer 840 to the inner layer 838. As best shown in FIG. 78, the commissure attachment member 812 can be folded to leave a small gap 846 between the outer layers 842.

Figure 71:
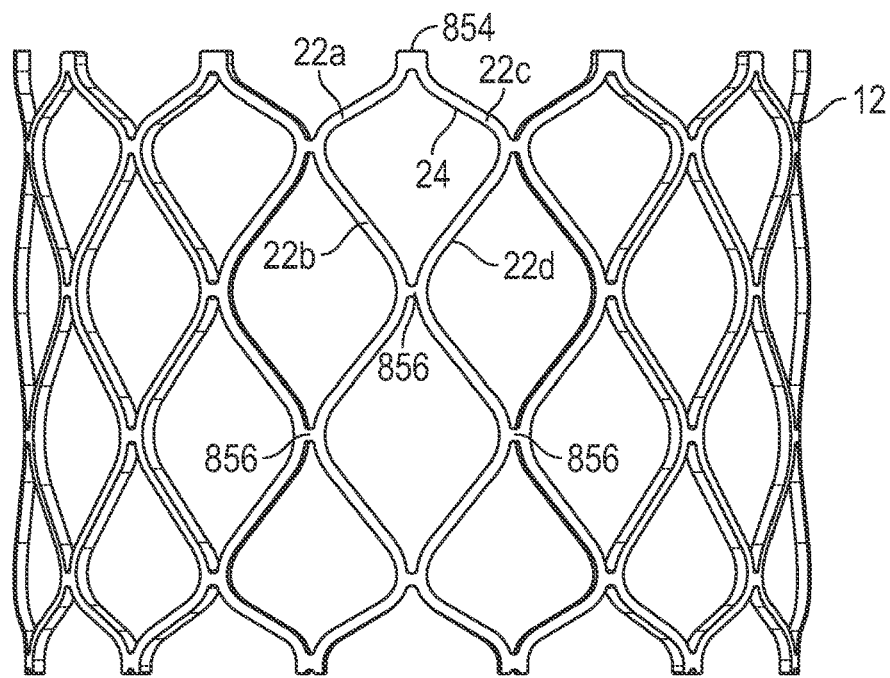
FIG. 71 is a side elevation view of the frame of the prosthetic heart valve of FIGS. 65-66.

The outer layers 842 can be secured to the frame 12, such as by suturing the outer peripheral edges 832 to struts 22 with stitching 848. As mentioned above, the outer peripheral edges 832 of the commissure attachment member 812 can generally correspond to the shape of a closed cell of the frame 12. For example, as shown in FIG. 71, the frame 12 in the illustrated embodiment comprises a plurality of generally diamond-shaped cells 24, each of which is formed by struts 22a, 22b, 22c, and 22d. Stitching 848 can be used to suture the outer peripheral edges 832 of the commissure attachment member 812 to struts 22a, 22b, 22c, 22d forming a closed cell 24. The commissure attachment member 812 can further include an upper tab 850 and a lower tab 852 projecting from the upper and lower edges of the central portion (FIG. 76). Stitching 848 can also be used suture the upper tab 850 an apex 854 formed by the intersection of struts 22a, 22c and to suture the lower tab 852 to a junction 856 formed by the intersection of struts 22b, 22d.

Figure 70:
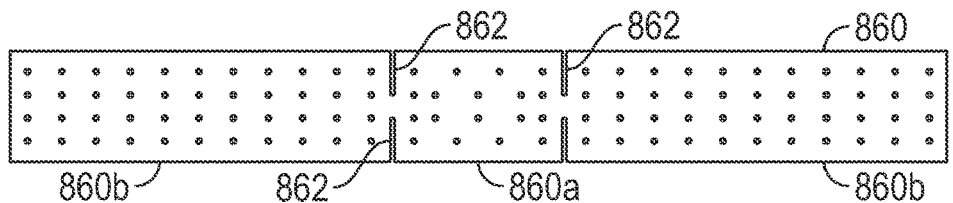
FIG. 70 is a plan view of an embodiment of a connecting skirt for connecting the cusp edge portion of a leaflet to a frame, shown in the flattened configuration.

The inflow or cusp edge portions 816 of the leaflets 814 can be secured to the frame 12 using a plurality of connecting skirts 860 (FIG. 70), which can be formed of the same materials as described above for the connecting skirt 100 (e.g., PET fabric). In the illustrated embodiment, a single connecting skirt 860 is provided for the cusp edge portion 816 of each leaflet 814 and is sized to extend along the entire length of a cusp edge portion 816 to locations just below the lower tabs 818 of the leaflet 814. FIG. 75B shows a connecting skirt 860 placed along the cusp edge portion 816 of a leaflet 814 prior to being attached to the leaflet with sutures. The connecting skirt 860 can include a central portion 860a sized to extend over the central lower edge portion and two side portions 860b sized to extend over the angled side edge portions extending from the lower central portion to the lower tabs 818. The connecting skirt 860 can be formed with slits 862 partially separating the side portions 860b from the central portion 860a to facilitate alignment of the skirt along the cusp edge portion as shown in FIG. 75B.

In alternative embodiments, plural connecting skirts can be provided for the cusp edge portion of each leaflet (e.g., the central portion 860a and the side portions 860b can be separate pieces of fabric). In another embodiment, a single connecting skirt can be used to secure all of the leaflets to the frame; i.e., a single connecting skirt can be sized to extend along the cusp edge portions of all of the leaflets.

Figure 69:
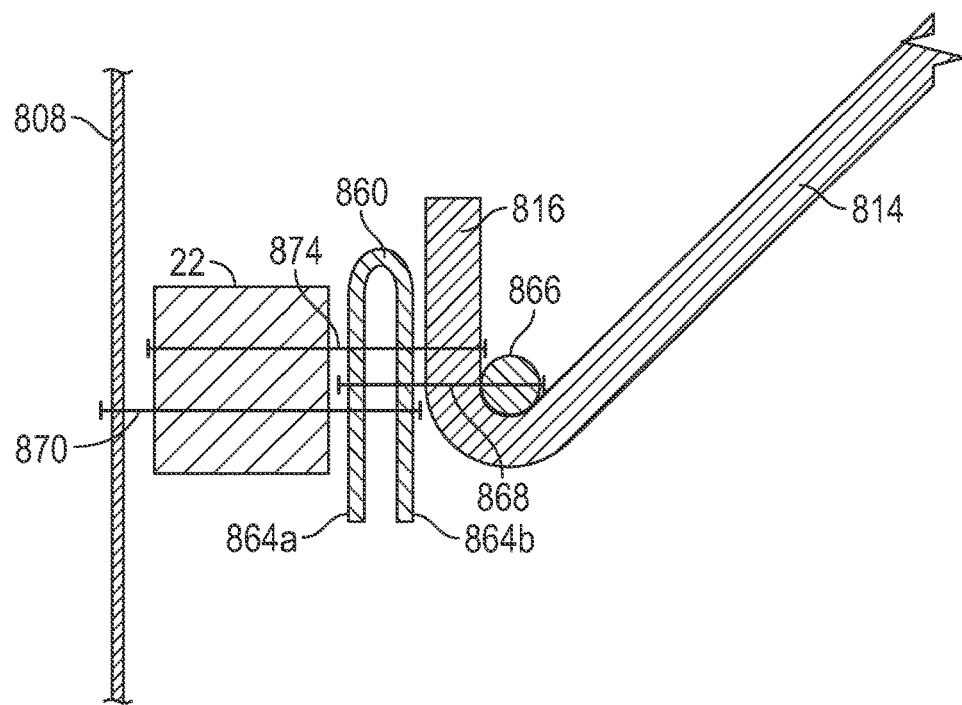
FIG. 69 is a cross-sectional view showing the attachment of the cusp edge portion of a leaflet to a connecting skirt, according to another embodiment.

Prior to attaching the leaflets to the frame, a connecting skirt 860 can be attached to the cusp edge portion of each leaflet. As shown in FIG. 69, a connecting skirt 860 can be folded lengthwise to form two fold layers 864a, 864b and placed against the inflow surface of the cusp edge portion 816. A reinforcing member or chord 866 (e.g., an Ethibond suture) can be placed against the outflow surface of the cusp edge portion opposite the connecting skirt 860. The reinforcing member 866 and the fold layers 864a, 864b can be sutured to each other and to the cusp edge portion 816 with stitching 868, which can be a single suture or multiple sutures extending through one or more layers of material.

Figure 67:
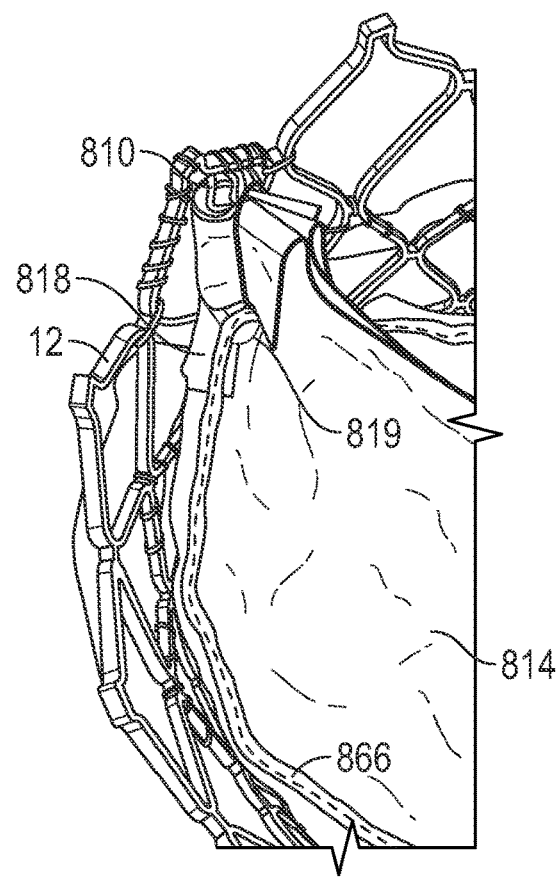
FIG. 67 is a perspective view of a portion of the prosthetic heart valve of FIGS. 65-66.

When suturing the reinforcing chord 866 to the leaflet 814, the lower tabs 818 can be folded downwardly against the cusp edge portion 816 (see FIG. 75B) and the reinforcing chord 866 can be placed over the folded lower tab 818. The upper ends of the connecting skirt 860 can be sized to extend over the folded lower tabs 818. Stitching 868 can be used to secure the reinforcing chord 866 in place against the folded lower tab 818. In particular embodiments, as best shown in FIG. 67, the reinforcing chord 866 can extend along the folded lower tab 818 of one leaflet 814, through the space between a pair of adjacent lower tabs 818 and a pair of upper tabs 820 under a commissure 810, and then along the lower tab 818 and the cusp edge portion of the adjacent leaflet 814. In some embodiments, a single reinforcing chord 866 extends continuously along the cusp edge portions 816 of all of the leaflets and through the spaces beneath each commissure 810. In other embodiments, plural reinforcing chords 866 can be used, with one reinforcing chord secured to the cusp edge portion of each leaflet. Where multiple reinforcing chords 866 are used, the ends of each chord can be connected (e.g., by tying or knotting) to adjacent ends of the other chords. For example, adjacent ends of two chords can be connected to each in the space underneath a commissure.

Figure 72:
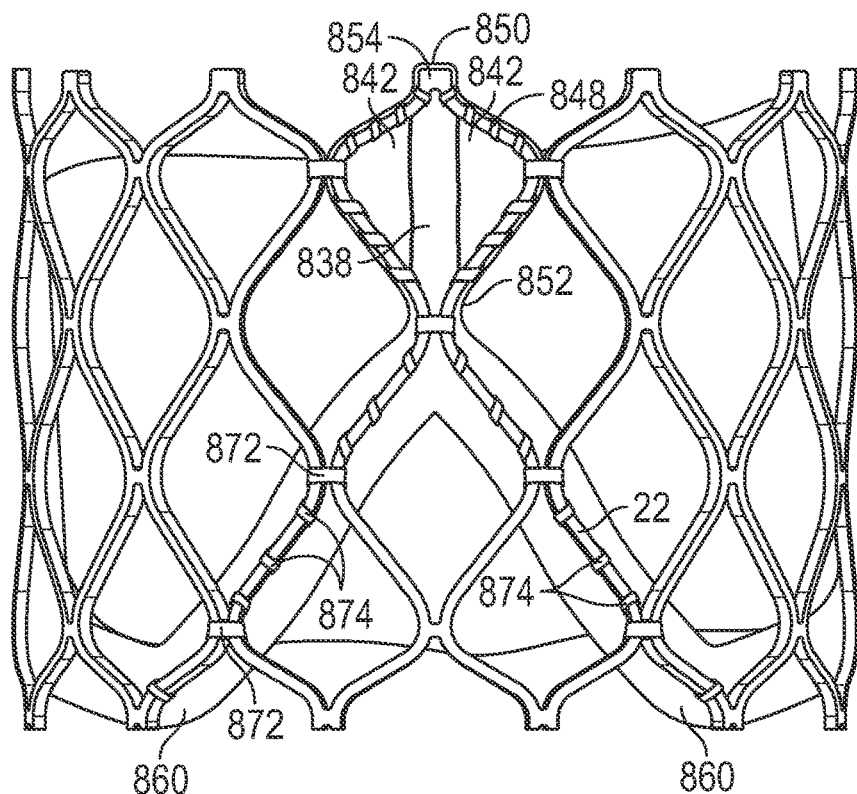
FIG. 72 shows the mounting of a valve assembly inside of the frame of FIG. 71, according to one embodiment.
Figure 73:
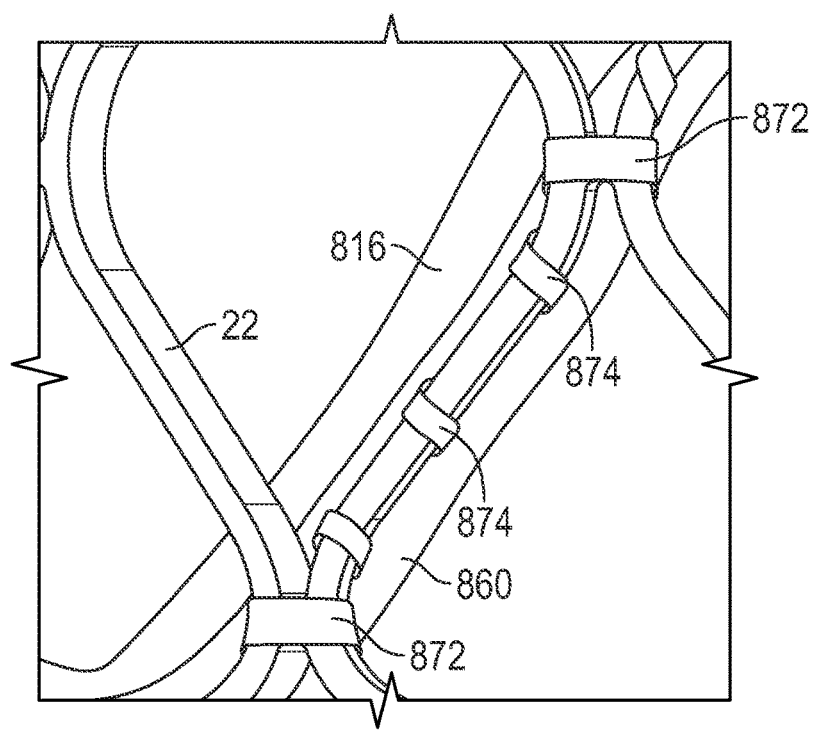
FIG. 73 is an enlarged view of a portion of the frame and the valve assembly of FIG. 72.
Figure 74:
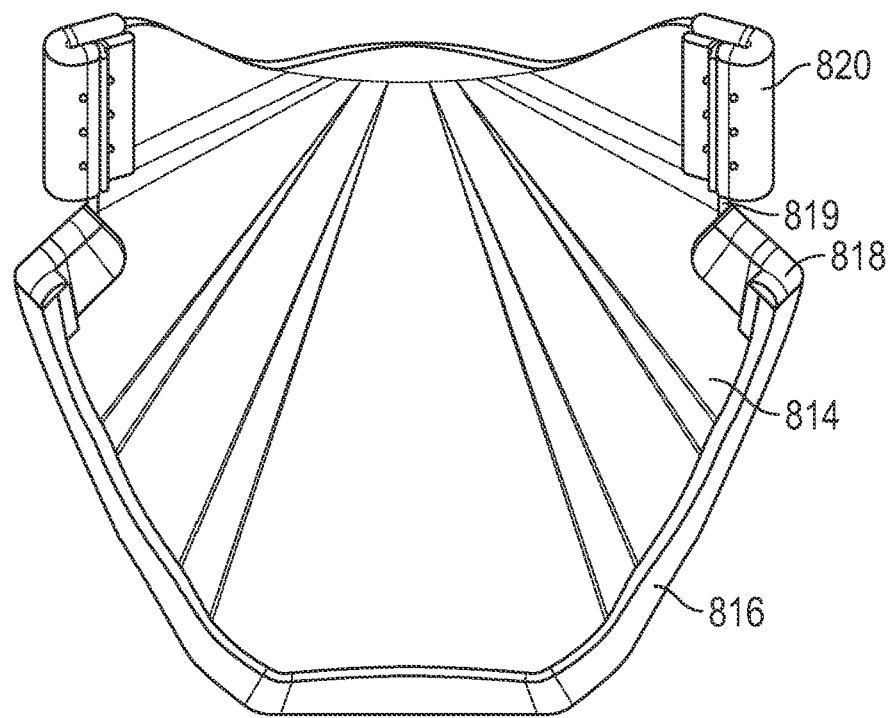
FIG. 74 is a perspective view of a leaflet of the prosthetic heart valve of FIGS. 65-66.

FIGS. 69, 72 and 73 illustrate the connection of the connecting skirts 860 to the frame 12, according to one embodiment. As shown, the connecting skirt can be sutured to struts 22 of the frame forming a diagonal line extending from a commissure 810 to the inflow end of the frame. In particular embodiments, one or both layers 864a, 864b of the connecting skirt can be secured to junctions 856 (FIG. 71) by individual stitches 872, and further with whip stiches 874 that are formed along the length of a struts 22 between two junctions 856. Each whip stitch 874 can extend through an edge portion 870 and around a strut 22 multiple times along the length of the strut. The whip stitches 874 optionally can extend through the cusp edge portion 816, as depicted in FIG. 69.

In alternative embodiments, the cusp edge portions 816 of the leaflets 814 can be mounted to the frame and/or the inner layer 804 of the sealing member using any of the techniques described herein. For example, any of the techniques or configurations described above with respect to FIG. 10-12B or 14-32 can be used to mount the leaflets 814 to the frame 12, without or without a reinforcing chord 866.

As discussed above in connection with the embodiment shown in FIGS. 33-37, the folded lower tabs 818 help reinforce the connection between the cusp edge portions 816 of the leaflets and the frame along the upper sections of the cusp edge portions adjacent the commissures 810. The folded lower tabs 304 also move the bending axes of the upper sections of the cusp edge portions inwardly and away from the inner surface of the frame to prevent or minimize contact between the leaflets and the frame in the areas below the commissures. In the illustrated embodiment, each lower tab 818 forms one additional layer of leaflet material on the upper (outflow) surface of the leaflet. In alternative embodiments, each lower tab 818 can be configured to form multiple additional layers of leaflet material, such as two, three, or four layers, on the upper surface of the leaflet to move the bending axes of the leaflet below the commissures even further away from the inner surface of the frame.

The side edges 819 between the lower and upper tabs 818, 82.0 can be left unattached to the frame of the prosthetic valve, as best shown in FIG. 67 and as previously described with respect to the configuration shown in FIG. 1C. As previously described, the unattached side edges 819 allow greater elongation or stretching of the leaflets in the axial direction when the prosthetic valve is compressed and allowing greater elongation or stretching of the leaflets in the radial direction when the prosthetic valve is expanded. During diastole, the adjacent side edges 819 can coapt with each other and prevent retrograde blood from flowing between the side edges 819. During systole, the adjacent side edges 819 can separate from each other and allow antegrade blood to flow between side edges 819 and help wash away blood from the areas underneath the commissures 810.

After the leaflet assembly (the leaflets 814 and the connecting skirts 860) is mounted to the frame, the sealing member 802 can be placed over and mounted to the frame as described above in connection with FIGS. 60-64. The triangular-shaped portions 808 of the inner layer 804 of the sealing member can be sutured to struts 22 of the frame and/or to one or both layers 864a, 864b of connecting skirts 860 with sutures 870 (see FIG. 69).

Figure 79:
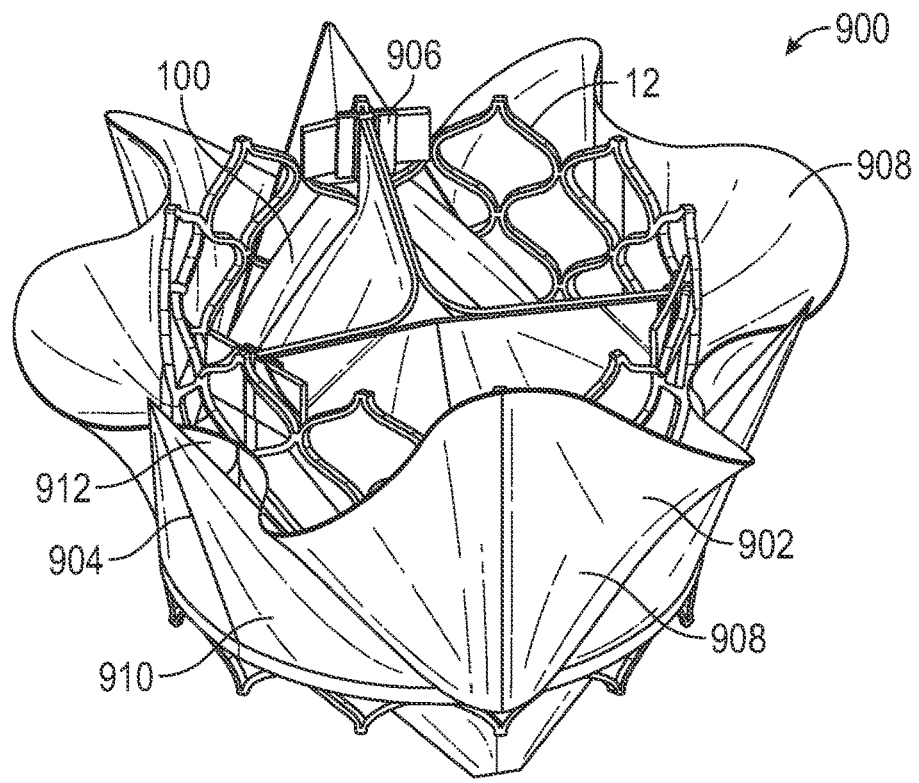
FIGS. 79 and 80 are perspective and top plan views, respectively, of a prosthetic heart valve, according to another embodiment.
Figure 80:
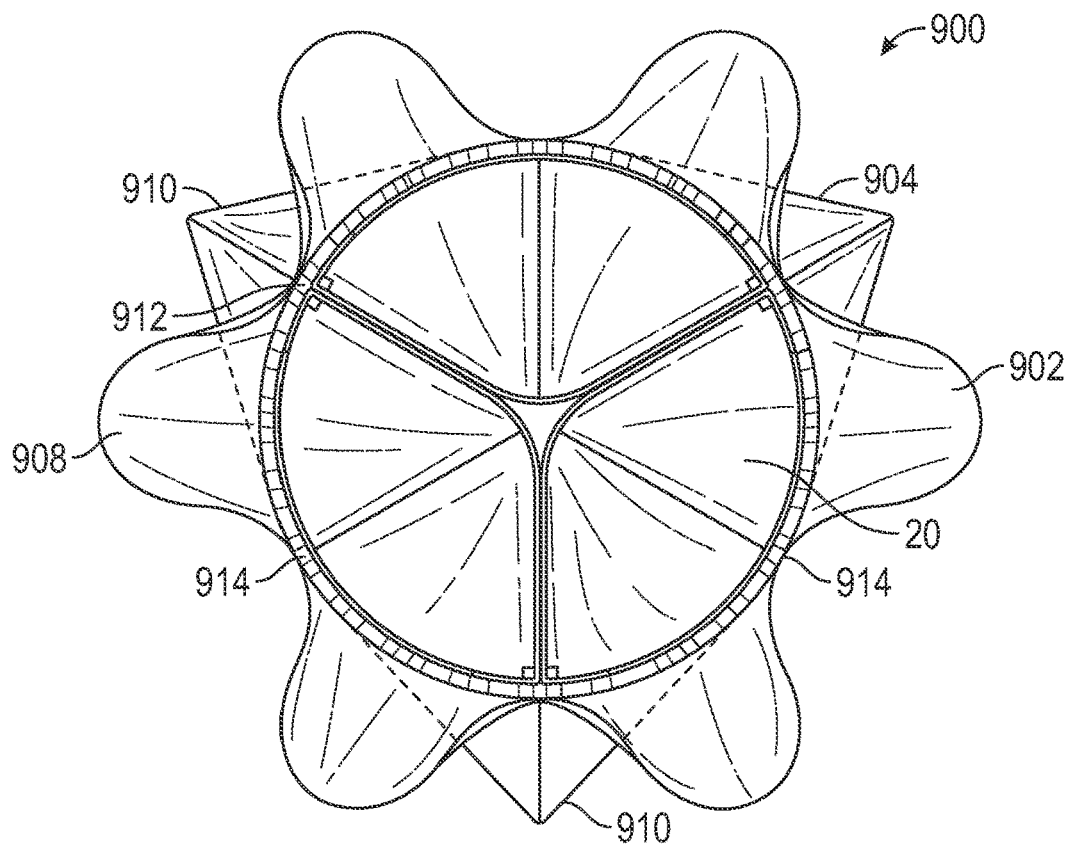

FIGS. 79-80 shows a prosthetic valve 900, according to another embodiment. The prosthetic valve 900 can similar to the prosthetic valve 10 described above except for the configuration of the sealing member. The prosthetic valve 900 in the illustrated embodiment comprises a sealing member 902 comprising a first layer 902 and a second layer 904, both of which are mounted on the outside of a frame 12. The first layer 902 comprises a plurality of diamond-shaped first portions 908 connected to each other at their upper (outflow) ends. The second layer 904 comprises a plurality of triangular-shaped portions 910 connected to each other at their lower (inflow) ends. The triangular-shaped portions 910, which are circumferentially aligned with commissures 906 of the prosthetic valve, are interspersed between the diamond-shaped portions 908, which are circumferentially aligned with the leaflets 20. As shown, the diamond-shaped portions 908 and the triangular-shaped portions 910 can overlap each to some extent in the vicinity of the commissures 906.

The triangular-shaped portions 910 generally correspond to the shape of the space between adjacent leaflets 20. The lower (inflow) end of the second layer 904 can be secured to the inflow end of the frame (e.g., with sutures). The lower edge portions 102 of the leaflets 20 can be coupled to the frame 12, such as with connecting skirts 100 as previously described, and the connecting skirts 100 can be secured to the sides of the triangular-shaped portions 910 (e.g., with sutures) through the cells of the frame. In this manner, the triangular-shaped portions 910 block antegrade blood from flowing outwardly through the cells the frame. The triangular-shaped portions 910 can also engage surrounding tissue to help seal the prosthetic valve and inhibit paravalvular leakage in conjunction with the diamond-shaped portions 908.

The first layer 902 can be secured to the frame 12 (e.g., with sutures) at the inflow end of each diamond-shaped portion 908 and at junctions 912 where the diamond-shaped portion 908 are connected to each other along the outflow edge of the first layer. The diamond-shaped portions 908 are configured to extend radially away from the frame to engage and seal with surrounding tissue when the prosthetic valve is deployed. The outflow edge of the first layer 902 between junctions 912 can remain unattached to the frame to receive retrograde blood between the first layer 902 and the frame. In some embodiments, the diamond-shaped portions 908 are configured to form an annular wave shape around the outside of the frame, as depicted in FIG. 67. In some embodiments, the outflow edge of the first layer 902 also can be secured to the frame (e.g., with sutures) at locations 914 between the junctions 912 to induce the first layer 902 to assume the wave shape when the prosthetic valve is expanded.

Although in the illustrated embodiment the first layer has diamond-shaped portions and the second layer has triangular shaped portions, other shapes are possible. For example, the sections 908, 910 of the first and second layers, can be square, oval, rectangular, circular, or combinations of one or more of these shapes.

Figure 81:
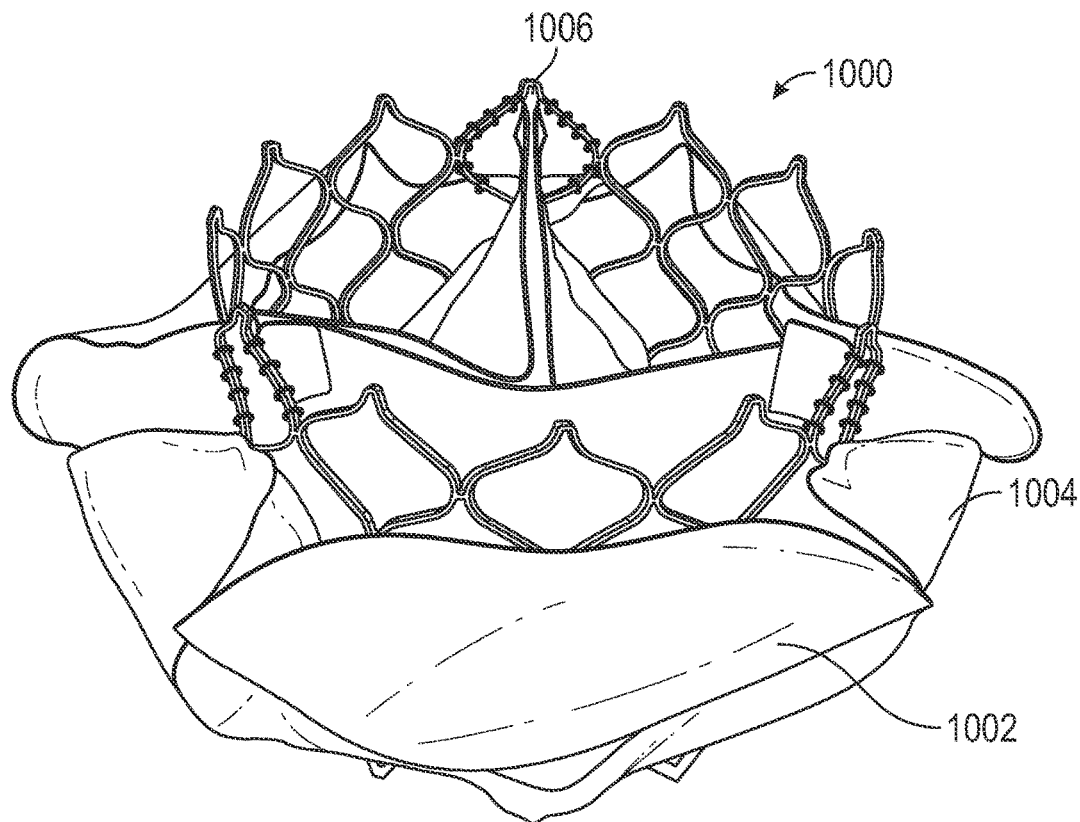
FIGS. 81 and 82 are perspective and top plan views, respectively, of a prosthetic heart valve, according to another embodiment.
Figure 82:
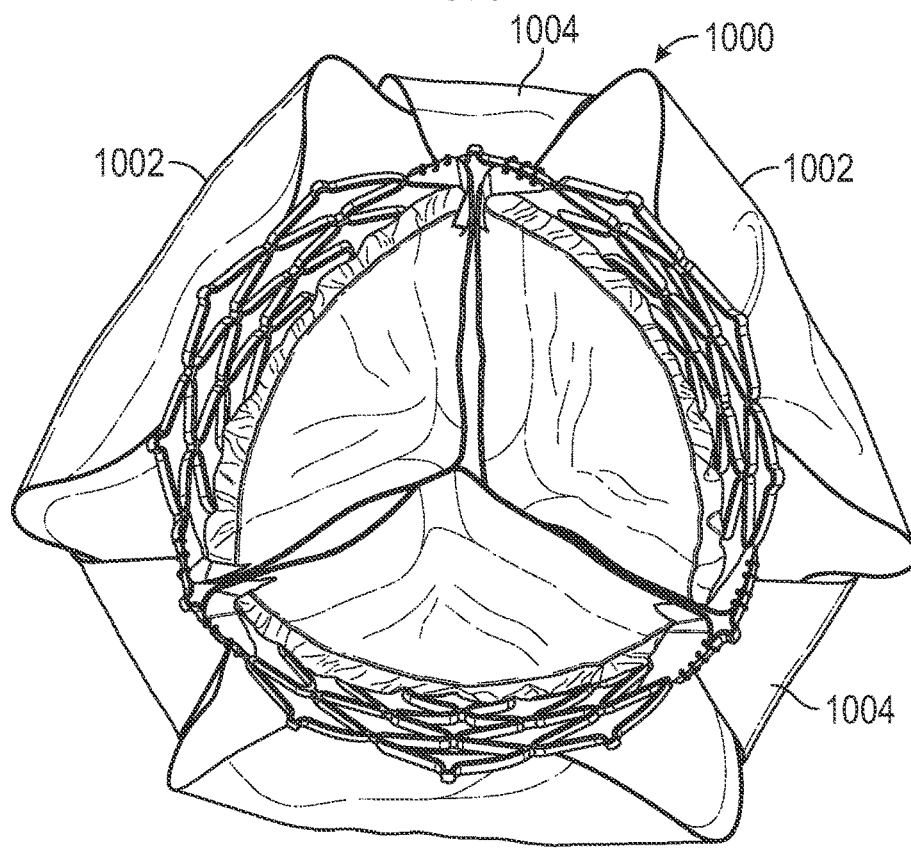

In alternative embodiments, the sections 908 of the first layer 902 can be separate pieces of material that are not connected to each other. Similarly, the sections 910 of the second layer 904 can be separate pieces of material that are not connected to each other. For example, FIGS. 81-82 show a prosthetic valve 1000 comprising a sealing member in the form of alternating diamond-shaped portions 1002 and triangular-shaped portions 1004 positioned around the outside of the frame. The diamond-shaped portions 1002 can be circumferentially aligned with the leaflets 20 and the triangular-shaped portions 1004 can be circumferentially aligned with the commissures 1006 of the leaflets. Each portion 1002, 1004 can be a separate piece of material that is sutured or otherwise secured to a frame 12 at its inflow and outflow ends. The diamond-shaped portions 1002 and the triangular-shaped portions 1004 can extend away from the frame 12 and engage surrounding tissue when the prosthetic valve is expanded.

Figure 83:
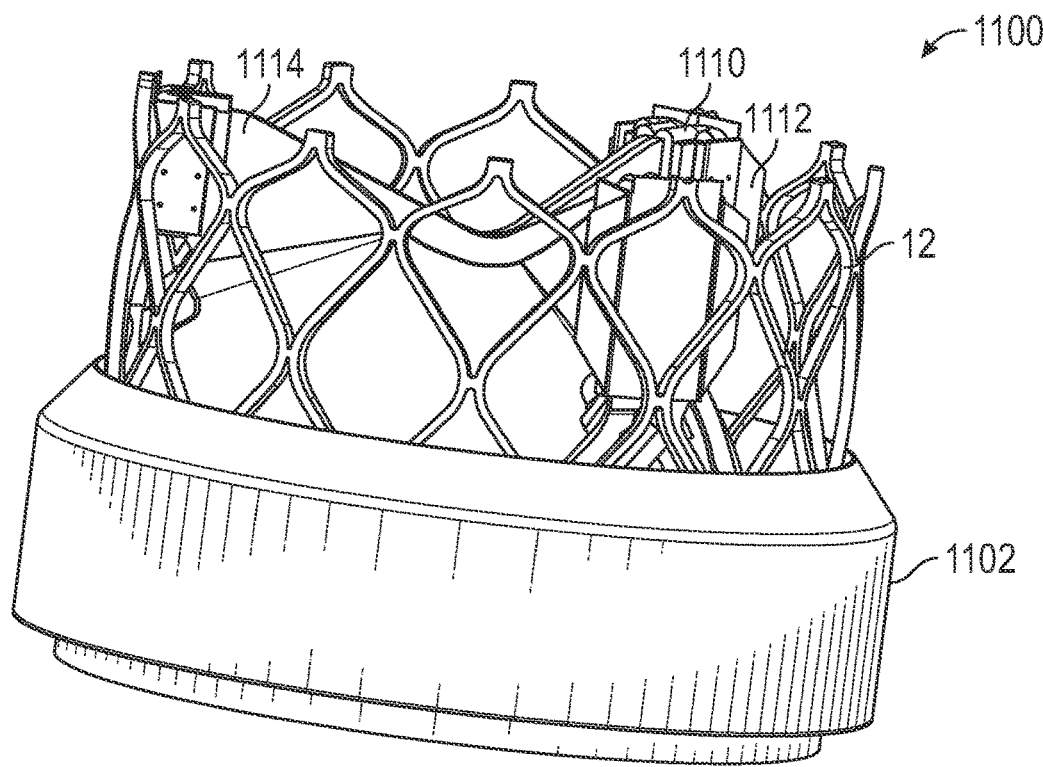
FIGS. 83 and 84 are perspective views of a prosthetic heart valve, according to another embodiment.
Figure 84:
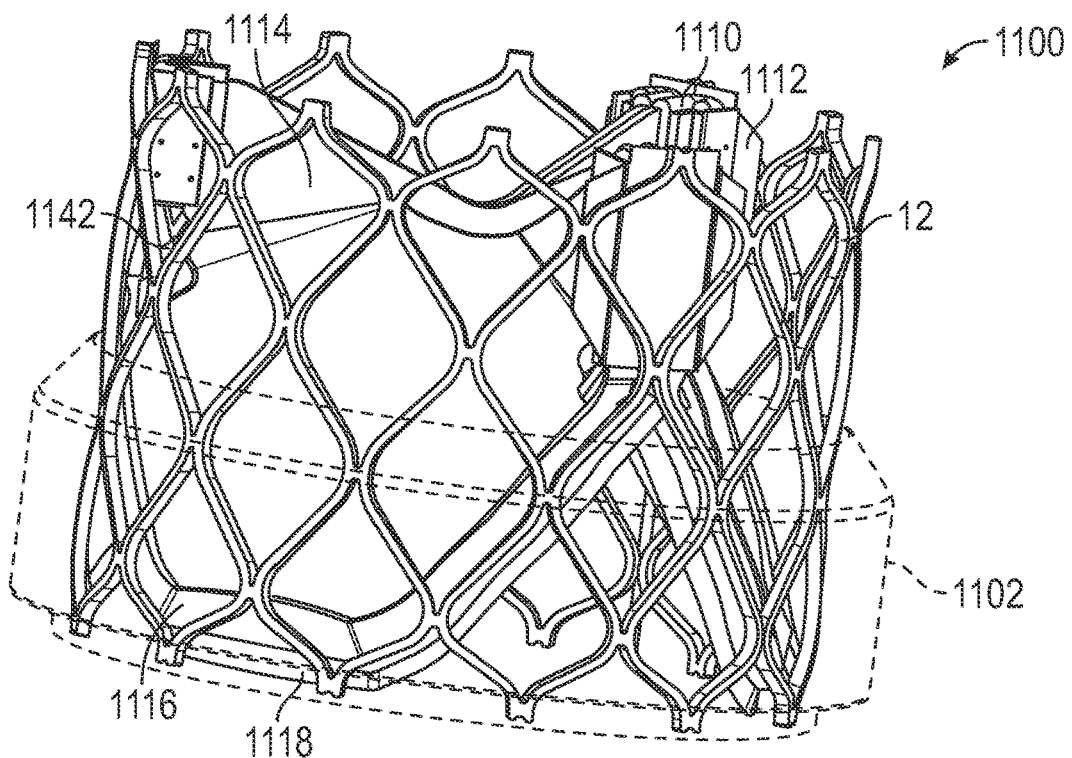

FIGS. 83-84 shows a prosthetic valve 1100, according to another embodiment. The prosthetic valve 1100 can include a sealing member 1102 mounted to the frame 12 as described above in connection with the embodiment of FIGS. 60-63. The prosthetic valve 1100 can include leaflets 1114 connected to each other at their outflow ends to form commissures 1110 that are mounted to the cells at the outflow end of the frame. The commissures 1110 can be formed by folding commissure tabs of the leaflets and securing them to a commissure attachment member 1112, which is then mounted to the frame. Each leaflet 1114 can have a lower or cusp edge portion 1116 that is folded upwardly toward the outflow end of the frame 12 as previously described and secured to the frame with a respective connecting skirt 1118, such as described above in connection with FIGS. 69-73. Any of the other techniques for mounting the cusp edge portions of the leaflets to the frame disclosed herein also can be used.

Figure 85:
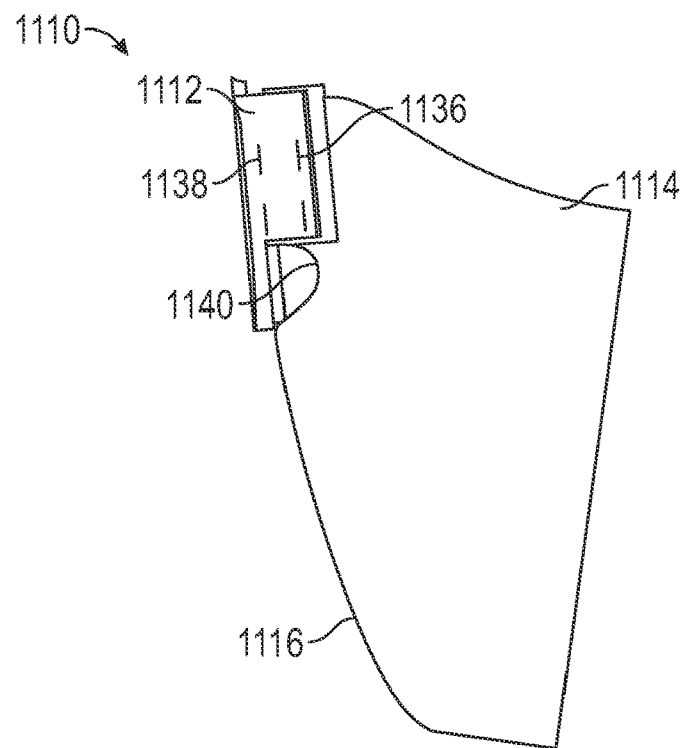
FIGS. 85 and 86 are side and top plan views, respectively, of one of the commissures of the prosthetic valve of FIGS. 83-84.
Figure 86:
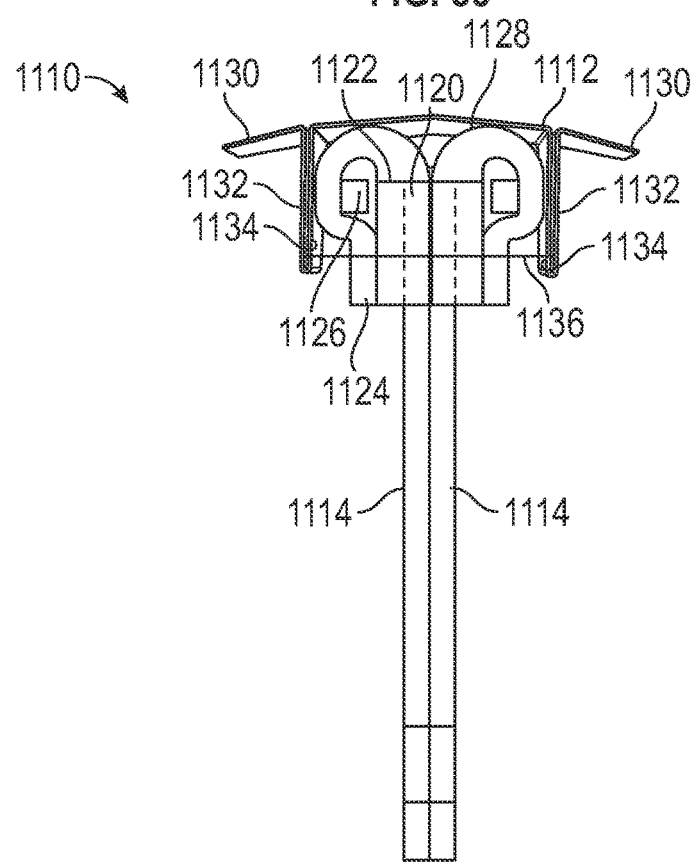

FIGS. 85-86 show a commissure 1110 formed from two leaflets 1114. As shown, each leaflet can have a commissure tab folded to form a first layer 1120, a second layer 1122, and a third layer 1124. Reinforcement members 1126 can be positioned between the second and third layers 1122, 1124. The commissure attachment member 1112 can be folded to form a center portion 1128, two side flaps 1130, and two pairs of fold layers 1132, 1134 that extend radially alongside third layers 1124 of the leaflets. The leaflets layers 1120, 1122, 1124 and the layers 1132, 1134 of the commissure attachment member 1112 can be secured to each other with one or more sutures 1136 and 1138. Each suture 1136, 1138 can form multiple in and out stitches that extend through all of these layers. As shown in FIG. 86, suture 1136 can form a stitch that extends over the upper edges of leaflet layers 1120, 1122, 1124. The side flaps 1130 can be sutured to the struts 22 of the frame, as shown in FIGS. 72 and 77.

As shown in FIG. 85, each leaflet can have opposing recessed side edges 1140 underneath each commissure that can remain unattached to the frame to promote blood flow in the areas underneath the commissures, as previously described. Each leaflet can also have opposing lower tabs 1142 (FIG. 84) similar to lower tabs 818 of prosthetic valve 800. A reinforcing chord, such as reinforcing chord 866 can be secured to the cusp edge portions 1116 of the leaflets as described above in connection with prosthetic valve 800.

Any of various delivery techniques can be used to deliver any of the prosthetic heart valves disclosed herein. In a retrograde approach, a prosthetic valve can be mounted in a radially compressed state along the distal end portion of the delivery catheter, and the delivery catheter and the prosthetic valve can be advanced through the aorta to the native aortic valve. Once the prosthetic valve is positioned within the native aortic valve, the prosthetic valve can be expanded, such as by inflating a balloon or another expansion device.

As noted above, any of the prosthetic valves disclosed herein can be configured to be self-expandable or can be expandable by applying an expansion force with a balloon or another type of expansion mechanism. An example of a delivery catheter that has an inflatable balloon for implanting a plastically-expandable prosthetic heart valve (which can be used for implanting any of the prosthetic valves disclosed herein) is disclosed in U.S. Patent Application Publication No. 2017/0065415, which is incorporated herein by reference. An example of a delivery catheter that can be used to deliver a self-expandable prosthetic heart valve (which can be used for implanting any of the prosthetic valves disclosed herein) is disclosed in U.S. Patent Application Publication No. 2014/0343670, which is incorporated herein by reference.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

A prosthetic heart valve according to the present disclosure can comprise a radially collapsible and expandable annular frame, a valvular structure (e.g., one or more leaflets) mounted within the frame, and one or more of the novel features described above, including, but not limited to, any of the sealing members described above, any of the specific leaflet configurations described above, any of the configurations for commissures described above, any of the configurations for connecting the cusp edge portions of leaflets to the frame, and/or combinations thereof.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending lengthwise of a component, usually in the proximal and distal directions, unless otherwise expressly defined.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic heart valve, comprising:
a radially expandable and compressible frame having an inflow end and an outflow end, the frame comprising a plurality of struts defining openings between them;
a valvular structure comprising a plurality of leaflets, each leaflet comprising a main body having an inflow surface, an outflow surface opposing the inflow surface, an edge surface extending from the inflow surface to the outflow surface and defining a thickness of the leaflet, a coaptation edge portion, and a cusp edge portion, the cusp edge portion of each leaflet being folded toward the outflow end of the frame along a bending axis to form an outer fold layer that extends parallel to a longitudinal axis of the frame such that the edge surface faces the outflow end of the frame;
a reinforcing member separate from the frame extending along the bending axis between the outer fold layer and the outflow surface of the main body of each leaflet of the plurality of leaflets;
a plurality of connecting skirts, wherein each connecting skirt is disposed between the cusp edge portion of an adjacent leaflet and the frame;
first stitching securing the reinforcing member and the connecting skirts to the cusp edge portions of the leaflets; and
second stitching securing the connecting skirts to selected struts of the frame.

2. The prosthetic heart valve of claim 1, wherein along the cusp edge portion of each leaflet, the first stitching extends only through the reinforcing member, the connecting skirt, and the cusp edge portion.

3. The prosthetic heart valve of claim 2, wherein the second stitching includes whip stitches that extend through each of the connecting skirts and around the selected struts of the frame.

4. The prosthetic heart valve of claim 3, wherein the whip stitches do not extend through the reinforcing member, the connecting skirts, and the cusp edge portions.

5. The prosthetic heart valve of claim 1, wherein each connecting skirt comprises a central portion and first and second side portions, and wherein the central portion is partially separated from each of the first and the second side portions by two or more slits.

6. The prosthetic heart valve of claim 1, wherein each leaflet has opposing edge portions between opposing commissure tabs and the cusp edge portion that are unattached to the frame, each unattached edge portion defining a notch in the leaflet.

7. The prosthetic heart valve of claim 1, wherein each leaflet comprises a pair of opposing commissure tabs, wherein each commissure tab is paired with an adjacent commissure tab of an adjacent leaflet to form a plurality of commissures that are fixed relative to the frame, and wherein each commissure is coupled to a commissure attachment member, each commissure attachment member comprising first and second side portions extending laterally from a central portion.

8. The prosthetic heart valve of claim 7, wherein outer peripheral edges of the first and the second side portions of the commissure attachment member are shaped such that each outer peripheral edge corresponds to one half of a diamond shaped cell of the frame.

9. The prosthetic heart valve of claim 1, wherein the reinforcing member comprises a multi-filament suture.

10. A prosthetic heart valve, comprising:
a radially expandable and compressible frame having an inflow end and an outflow end, the frame comprising a plurality of struts defining openings between them;
a valvular structure comprising exactly three leaflets, each leaflet comprising a main body having an inflow surface, an outflow surface opposing the inflow surface, an edge surface extending from the inflow surface to the outflow surface and defining a thickness of the leaflet, a coaptation edge portion, and a cusp edge portion; and
exactly three connecting skirts, wherein each connecting skirt is stitched to the cusp edge portion of an adjacent leaflet and is disposed between the cusp edge portion and the frame, wherein each connecting skirt comprises a central portion and first and second side portions, and wherein the central portion is partially separated from each of the first and the second side portions by one or more linear slits that extend from a side edge of the connecting skirt into a main body of the connecting skirt and through a thickness of the connecting skirt;
wherein the central portion of each connecting skirt extends over a lower central portion of a cusp edge portion on the inflow surface of the leaflet and the first and the second side portions extend over opposing side portions of the cusp edge portion on the inflow surface of the leaflet, and
wherein each leaflet is folded toward the outflow end of the frame along a bending axis to form a respective outer fold layer that extends parallel to a longitudinal axis of the frame such that the respective edge surface of each leaflet faces the outflow end of the frame.

11. The prosthetic heart valve of claim 10, wherein the one or more slits of each connecting skirt comprises a first pair of first and second opposing slits separating the central portion from the first side portion and a second pair of first and second opposing slits separating the central portion from the second side portion.

12. The prosthetic heart valve of claim 10, wherein:
the cusp edge portion of each leaflet is folded toward the outflow end of the frame along a bending axis; and
a reinforcing member separate from the frame that extends along and is secured to an outflow surface of the cusp edge portion of each leaflet along the bending axis.

13. The prosthetic heart valve of claim 12, further comprising a plurality of first stitches securing the cusp edge portion of each leaflet to the reinforcing member and a corresponding connecting skirt of the plurality of connecting skirts.

14. The prosthetic heart valve of claim 13, further comprising a plurality of second stitches securing the plurality of connecting skirts including the corresponding connecting skirt to selected struts of the frame.

15. The prosthetic heart valve of claim 10, further comprising a sealing member disposed on an outer surface of the frame.

16. A prosthetic heart valve, comprising:
- a radially expandable and compressible frame having an inflow end and an outflow end, the frame comprising a plurality of struts defining openings between them;
- a valvular structure comprising a plurality of leaflets, each leaflet comprising a main body having an inflow surface, an outflow surface opposing the inflow surface, an edge surface extending from the inflow surface to the outflow surface and defining a thickness of the leaflet, a coaptation edge portion, and a cusp edge portion, the cusp edge portion of each leaflet being folded toward the outflow end of the frame along a bending axis to form an outer fold layer extending from the main body, the outer fold layer including the edge surface, wherein the edge surface of the outer fold layer faces the outflow end of the frame;
- a reinforcing member extending along the bending axis between the outer fold layer and the outflow surface of the main body of each leaflet of the plurality of leaflets;
- a plurality of connecting skirts, wherein each connecting skirt is disposed between the outer fold layer of each leaflet and the frame;
- a plurality of first stitches extending only through the connecting skirt, the outer fold layer, and the reinforcing member along each leaflet; and
- a plurality of second stitches securing each connecting skirt to selected struts of the frame.

17. The prosthetic valve of claim 16, wherein the second stitches comprise whip stitches that extend around the selected struts of the frame.

18. The prosthetic valve of claim 16, wherein each connecting skirt comprises a central portion and first and second side portions, and wherein the central portion is partially separated from the first and the second side portions by two or more slits.

* * * * *